US009650655B2

(12) United States Patent
Vroom et al.

(10) Patent No.: US 9,650,655 B2
(45) Date of Patent: *May 16, 2017

(54) PRODUCTION OF FATTY ALCOHOLS FROM ENGINEERED MICROORGANISMS

(71) Applicant: Codexis, Inc., Redwood City, CA (US)

(72) Inventors: Jonathan Vroom, South San Francisco, CA (US); Svetlana Balatskaya, Fremont, CA (US); Yoram Barak, Greenwich, CT (US); Louis Clark, San Francisco, CA (US); Trish Choudhary, Foster City, CA (US); Kristian Karlshoej, Naperville, IL (US); Fernando Valle, Burlingame, CA (US); Kaman Chan, San Bruno, CA (US)

(73) Assignee: Codexis, Inc., Redwood City, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/415,665

(22) PCT Filed: Jul. 19, 2013

(86) PCT No.: PCT/US2013/051340
§ 371 (c)(1),
(2) Date: Jan. 19, 2015

(87) PCT Pub. No.: WO2014/015278
PCT Pub. Date: Jan. 23, 2014

(65) Prior Publication Data
US 2015/0176040 A1 Jun. 25, 2015

Related U.S. Application Data

(63) Continuation-in-part of application No. PCT/US2012/069444, filed on Dec. 13, 2012, and a
(Continued)

(51) Int. Cl.
C12P 7/64 (2006.01)
C12N 9/02 (2006.01)
(Continued)

(52) U.S. Cl.
CPC ............... *C12P 7/64* (2013.01); *A61K 8/342* (2013.01); *C11D 3/2013* (2013.01); *C12N 9/001* (2013.01);
(Continued)

(58) Field of Classification Search
CPC ...... C12N 9/93; C12N 9/98; C12Y 203/0118; C12Y 101/01; C12Y 101/01009;
(Continued)

(56) References Cited

U.S. PATENT DOCUMENTS 4,356,196 A  10/1982  Hultquist
4,461,648 A   7/1984  Foody
(Continued)

FOREIGN PATENT DOCUMENTS

WO      2007/136762 A2    11/2007
WO   WO 2007/136762   *  11/2007
(Continued)

OTHER PUBLICATIONS

Abdel-Mawgoud et al., Springer-Verlag Berlin Heidelberg., Biosurfactants, vol. 20 of the series Microbiology Monographs, Date: Sep. 14, 2010, Rhamnolipids: Detection, Analysis, Biosynthesis, Genetic Regulation, and Bioengineering of Production., pp. 13-55.*
(Continued)

*Primary Examiner* — Alexander Kim
(74) *Attorney, Agent, or Firm* — Codexis, Inc.

(57) ABSTRACT

Recombinant microorganisms are provided which have been engineered to produce fatty alcohols. Also provided are recombinant microorganisms which comprise a heterolo-
(Continued)

Pathway for the Production of Fatty Alcohols gous polynucleotide encoding a fatty alcohol reductase enzyme and an introduced polynucleotide encoding a β-ketoacyl acyl carrier protein synthase.

33 Claims, 18 Drawing Sheets

Related U.S. Application Data continuation-in-part of application No. PCT/US2012/069553, filed on Dec. 13, 2012, and a continuation-in-part of application No. PCT/US2013/037472, filed on Apr. 19, 2013.

(60) Provisional application No. 61/674,053, filed on Jul. 20, 2012.

(51) Int. Cl.
| | | |
|---|---|---|
| *C12N 9/10* | (2006.01) | |
| *C12P 7/04* | (2006.01) | |
| *A61K 8/34* | (2006.01) | |
| *C11D 3/20* | (2006.01) | |
| *C12N 9/04* | (2006.01) | |
| *C12N 9/16* | (2006.01) | |
| *C12N 9/88* | (2006.01) | |
| *C12N 9/90* | (2006.01) | |
| *C12N 9/00* | (2006.01) | |

(52) U.S. Cl.
CPC ......... *C12N 9/0006* (2013.01); *C12N 9/0008* (2013.01); *C12N 9/1007* (2013.01); *C12N 9/1029* (2013.01); *C12N 9/16* (2013.01); *C12N 9/88* (2013.01); *C12N 9/93* (2013.01); *C12P 7/04* (2013.01); *C12Y 203/0118* (2013.01); *A61K 2800/85* (2013.01); *C12Y 101/01* (2013.01); *C12Y 101/011* (2013.01); *C12Y 103/01009* (2013.01); *C12Y 103/99* (2013.01); *C12Y 201/01005* (2013.01); *C12Y 203/01029* (2013.01); *C12Y 203/01041* (2013.01); *C12Y 203/01086* (2013.01); *C12Y 301/02* (2013.01); *C12Y 301/02001* (2013.01); *C12Y 301/02027* (2013.01); *C12Y 402/01059* (2013.01); *C12Y 602/01* (2013.01); *C12Y 602/01003* (2013.01)

(58) Field of Classification Search
CPC .......... C12Y 103/01009; C12Y 103/99; C12Y 203/01029; C12Y 203/01041; C12Y 203/01086; C12Y 301/02001; C12Y 301/02027; C12Y 402/01059; C12Y 602/01; C12Y 602/01003; C12P 7/64; C12P 7/04; A61K 8/342; A61K 2800/85
See application file for complete search history.

(56) References Cited

U.S. PATENT DOCUMENTS

| | | |
|---|---|---|
| 4,556,430 A | 12/1985 | Converse et al. |
| 4,600,590 A | 7/1986 | Dale |
| 5,037,663 A | 8/1991 | Dale |
| 5,171,592 A | 12/1992 | Holtzapple et al. |
| 5,344,771 A | 9/1994 | Davies et al. |
| 5,512,482 A | 4/1996 | Voelker et al. |
| 5,723,761 A | 3/1998 | Voelker et al. |
| 5,910,631 A | 6/1999 | Topfer et al. |
| 5,939,544 A | 8/1999 | Karstens et al. |
| 5,955,329 A | 9/1999 | Yuan et al. |
| 6,106,888 A | 8/2000 | Dale et al. |
| 6,117,679 A | 9/2000 | Stemmer |
| 6,143,538 A | 11/2000 | Somerville et al. |
| 6,150,512 A | 11/2000 | Yuan |
| 6,176,176 B1 | 1/2001 | Dale et al. |
| 6,376,246 B1 | 4/2002 | Crameri et al. |
| 6,429,175 B1 | 8/2002 | Stuart, Jr. et al. |
| 6,586,182 B1 | 7/2003 | Patten et al. |
| 7,332,311 B2 | 2/2008 | Lardizabal et al. |
| 7,465,791 B1 | 12/2008 | Hallberg et al. |
| 7,754,457 B2 | 7/2010 | Foody et al. |
| 7,783,428 B2 | 8/2010 | Gustafsson et al. |
| 8,110,670 B2 | 2/2012 | Hu et al. |
| 2006/0195947 A1 | 8/2006 | Davis et al. |
| 2007/0031953 A1 | 2/2007 | Dunson, Jr. et al. |
| 2008/0104724 A1 | 5/2008 | Sticklen et al. |
| 2008/0220990 A1 | 9/2008 | Fox |
| 2009/0312196 A1 | 12/2009 | Colbeck et al. |
| 2010/0105963 A1 | 4/2010 | Hu |
| 2011/0000125 A1* | 1/2011 | McDaniel ............... C10L 1/026 44/388 |
| 2011/0195469 A1* | 8/2011 | Roessler ............... C12N 9/0008 435/155 |
| 2011/0250663 A1 | 10/2011 | Schirmer et al. |
| 2012/0009640 A1* | 1/2012 | Behrouzian ............... C07C 1/22 435/157 |
| 2012/0142979 A1 | 6/2012 | Keasling et al. |
| 2012/0172281 A1 | 7/2012 | Scheibel et al. |
| 2013/0078686 A1 | 3/2013 | Holtzapple et al. |

FOREIGN PATENT DOCUMENTS

| | | |
|---|---|---|
| WO | 2008/119082 A2 | 10/2008 |
| WO | 2009/045651 A2 | 4/2009 |
| WO | 2010/075483 A2 | 7/2010 |
| WO | 2010/112129 A1 | 10/2010 |
| WO | 2011/008535 A1 | 1/2011 |
| WO | 2011/008565 A1 | 1/2011 |
| WO | 2011/019858 A1 | 2/2011 |
| WO | 2011/028554 A1 | 3/2011 |
| WO | 2012/006114 A2 | 1/2012 |
| WO | 2012/042544 A1 | 4/2012 |
| WO | 2012/042545 A1 | 4/2012 |

OTHER PUBLICATIONS

Thioesterase [Umbellularia californica] (last viewed on Oct. 18, 2016).*
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).
Archer, C.T., et al., "The genome sequence of *E. coli* W (ATCC 9637): comparative genome analysis and an improved genome-scale reconstruction of *E. coli*," BMC Genomics, 12:9 [2011].
Black, P.N. et al., "Cloning, sequencing, and expression of the fadD gene of *Escherichia coli* encoding acyl coenzyme A synthetase," J. Biol. Chem., 267:25513-25520 [1992].
Brosius, J., et al., "Spacing of the -10 and -35 Regions in the tac Promoter," J. Biol. Chem., 260(6): 3539-3541 [1985].
Cantu, D.C., et al., "Thioesterases: a new perspective based on their primary and tertiary structures," Protein Science, 19(7):1281-1295 (2010).
Cantu, D.C., et al., "ThYme: a database for thioester-active enzymes," Nucleic Acid Research, 39:D342-D346 (2011).
Carter, P., "Site-directed mutagenesis," Biochem. J., 237:1-7 [1986].
Chen, V., et al., "Genome Sequence of Cronobacter sakazakii E899, a Strain Associated with Human Illness," J. Bacteriol., 193(20):5861 [2011].
Cho, H., et al., "Defective Export of a Periplasmic Enzyme Disrupts Regulation of Fatty Acid Synthesis," J. Biol. Chem., 270:4216-4219 [1995].
Choi, K.H., et al,, "Beta-Ketoacyl-Acyl Carrier Protein Synthase III (FabH) Is a Determining Factor in Branched-Chain Fatty Acid Biosynthesis," J. Bacteriol., 182:365-370 [2000].

(56) References Cited

OTHER PUBLICATIONS

Choi, K.H., et al., "Identification and Substrate Specificity of Beta-Ketoacyl (Acyl Carrier Protein) Synthase III (mtFabH) from *Mycobacterium tuberculosis*," J. Biol. Chem., 275:28201-28207 [2000].
Court, D.L., et al., "Genetic Engineering Using HornologousRecombination," Annual Rev. Genet., 36:361-388 [2002].
Datsenko, K.A., et al., "One-step inactivation of chromosomal genes in *Escherichia coli* K-12 using PCR products," PNAS, 97(12): 6640-6645 [2000].
De Boer, H.A., et al., "The tac promoter: A functional hybrid derived from the trp and lac promoters," Proc. Natl Acad. Sci. USA, 80: 21-25 (1983).
Doan, T.T.P., et al., "Functional expression of five Arabidopsis fatty acyl-CoA reductase genes in *Escherichia coli*," J. Plant Physiol., 166: 787-796 [2009].
Dower, W.J., et al., "High efficiency transformation of *E. coli* by high voltage electroporation," Nucleic Acids Research, 16(13): 6127-6145 [1988].
Eblen. D.P.. et al., "Studies to Select Appropriate Nonpathogenic Surrogate *Escherichia coli* Strains for Potential Use in Place of *Escherichia coli* O157:H7 and *Salmonella* in Pilot Plant Studies," J. of Food Protection, 68(2):282-291 [2005].
Gajiwala, K.S., et al., "Crystal structures of bacterial FabH suggest a molecular basis for the substrate specificity of the enzyme," FEBS Letters, 583:2939-2946 [2009].
Hayashi, K., et al., "Highly accurate genome sequences of *Escherichia coli* K-12 strains MG1655 and W3110," Mol. Syst. Biol., 2(2006.0007):1-5 [2006].
Heath, R.J., et al., "Enoyl-Acyl Carrier Protein Reductase (fabI) Plays a Determinant Role in Completing Cycles of Fatty Acid Elongation in *Escherichia coli*," J. Biol. Chem., 270(44): 26538-26542 [1995].
Heath, R.J., et al., "Roles of the FabA and FabZ Beta-Hydroxyacyl-Acyl Carrier Protein Dehydratases in *Escherichia coli* Fatty Acid Biosynthesis," J. Biol. Chem., 271(44): 27795-27801 [1996].
Henikoff, S., et al., "Amino add substitution matrices from protein blocks," Proc. Natl. Acad. Sci. USA, 89:10915-10919 [1992].
Hofvander, P., et al., "A prokaryotic acyl CoA reductase performing reduction of fatty acyl-CoA to fatty alcohol," FEBS Letters, 585:3538-3543 (2011).
Ishige, T., et al., "Long-Chain Aldehyde Dehydrogenase That Participates in n-Alkane Utilization and Wax Ester Synthesis in *Acinetobacter* sp. Strain M-1," Appl. Environ. Microbiol., 66:3481-3486 (2000).
Jones, A., et al., "Palmitoyl-Acyl Carrier Protein (ACP) Thioesterase and the Evolutidnary-Origin of Plant ACyl-ACP Thioesterases," The Plant Cell, 7:359-371 (1995).
Kalscheuer, R., et al., "Neutral Lipid Biosynthesis in Engineered *Escherichia coli*: Jojoba Oil-Like Wax Esters and Fatty Acid Butyl Esters," Appl. Environ. Microbiol., 72:1373-79 [2006].
Khandekar, S.S., et al., "Identification, Substrate Specificity, and Inhibition of the *Streptococcus pneumoniae* Beta-Ketoacyl-Acyl Carrier Protein Synthase III (FabH)," J. Biol. Chem., 276:30024-30030 [2001].
Kitagawa, M., "Complete set of ORF clones of *Escherichia coli* ASKA library (A Complete Set of *E. coli* K-12 ORF Archive): Unique Resources for Biological Research," DNA Res., 12:291-299 [2005].
Lai, C.Y., et al., "Beta-Ketoacyl-Acyl Carrier Protein Synthase III (FabH) Is Essential for Bacterial Fatty Acid Synthesis," J. Biol. Chem., 278(51):51494-51503 [Dec. 2003].
Lai, C.Y., et al., "Isolation and Characterization of Beta-Ketoacyl-Acyl Carrier Protein Reductase (fabG) Mutants of *Escherichia coli* and *Salmonella enterica* Serovar Typhimurium," J. Bacteriol., 186(6):1869-1878 [2004].
Lathe, R., et al., "Plasmid and bacteriophage vectors for excision of intact inserts," Gene, 57:193-201 [1987].
Lerner, C.G., et al., "Low copy number plasmids for regulated low-level expression of cloned genes in *Escherichia coli* with blue/white insert screening capability," Nucleic Adds Research, 18(15):4631 [1990].
Li, J.J., et al., "Reductions" in Modern Organic Synthesis in the Laboratory, Oxford University Press, Inc., p. 81-83 [2007].
Ling, M.M. et al., "Appoaches to DNA Muagenesis: An Overview," Anal. Biochem., 254(2):157-78 [1997].
Link, A.J., et al., "Methods for generating precise deletions and insertions in the genome of wild-type *Escherichia coli*: application to open reading frame characterization," J. Bact., 179: 6228-6237 [1997].
Magnuson, K., et al., "Cloning and nucleotide sequence of the fabD gene encoding malonyl coenzyme A-acyl carrier protein transacylase of *Escherichia coli*," FEBS Letters, 299(3): 262-266 [1992].
Magnuson, K., et al., "Regulation Fatty Acid Biosynthesis in *Escherichia coli*," Microbiol. Reviews, 57(3):522-542 [1993].
Mendoza, D.D., et al., "Thermal regulation of membrane fluidity in *Escherichia coli*. Effects of overproduction of beta-ketoacyl-acyl carrier protein synthase I," J. Biol Chem, 258(4):2098-2101 [1983].
Metz, J.G., et al., "Purification of a Jojoba Embryo Fatty Acyl-Coenzyme A Reductase and Expression of Its cDNA in High Erucic Acid Rapeseed," Plant Physiol., 122:635-644 [2000].
Minshull, J., et al., "Protein evolution by molecular breeding," Curr. Op. Chem. Biol., 3:284-290 [1999].
Morgan-Kiss, R.M., et al., "The *Escherichia coli* fadK (ydiD) Gene Encodes an Anerobically Regulated Short Chain Acyl-CoA Synthetase," J. Biol. Chem., 279:37324-37333 [2004].
Morgan-Kiss, R.M., et al., "The Lactococcus lactis FabF fatty acid synthetic enzyme can functionally replace both the FabB and FabF proteins of *Escherichia coli* and the FabH protein of Lactococcus lactis," Arch. Microbiol., 190:427-459 [2008].
Moto, K., et al., "Pheromone gland-specific fatty-acyl reductase of the silkmoth, *Bombyx mori*," PNAS, 100(16):9156-9161 [2003].
Needleman, S., et al., "A general method applicable to the search for similarities in the amino acid sequence of two proteins," J. Mol. Biol. 48:443-453 (1970).
Nevoigt, E., et al., "Engineering of Promoter Replacement Cassettes for Fine-Tuning of Gene Expression in *Saccharomyces cerevisiae*," Appl. Environ. Microbiol., 72:5266-5273 (2006).
Nomura, C.T., et al., "Coexpression of Genetically Engineered 3-Ketoacyl-ACP Synthase III (fabH) and Polyhydroxyalkanoate Synthase (phaC) Genes Leads to Short-Chain-Length-Medium-Chain-Length Polyhydroxyalkanoate Copolymer Production from Glucose in *Escherichia coli* JM109 ," Appl. Environ. Microbiol., 70(2):999-1007 [2004].
Notredame, C., et al., "T-COFFEE: A novel method for multiple sequence alignments," JMB, 302:205-217, [2000].
Ong, S.Y., et al., Complete Genome Sequence of *Salmonella enterica* subsp. *enterica* Serovar Typhi P-stx-12, J. Bacteriol., 194:2115-2116 [2012].
Orosz, A., "Analysis of the complex transcription termination region of the *Escherichia coli* rrnB gene," Eur. J. Biochem., 201: 653-659 [1991].
Qui, X., et al., "Crystal structure and substrate specificity of the Beta-ketoacyl-acyl carner protein synthase III (FabH) from *Staphylococcus aureus*," Protein Sci., 14:2087-2094 [2005].
Reiser, S., et al., "Isolation of mutants of Acinetobacter calcoaceticus deficient in wax ester synthesis and complementation of one mutation with a gene encoding a fatty acyl coenzyme A reductase," J. Bacteriol., 179:2969-2975 (1997).
Sadler, J.R., et al., "A perfectly symmetric lac operator binds the lac repressor very tightly," PNAS, 80: 6785-6789 [1983].
Salis, H., et al., "Automated design of synthetic ribosome bindin sites to control protein expression," Nature Biotechnology, 27(10): 946-951 [2009].
Scarsdale, J.N., et al., "Crystal Structure of the *Mycobacterium tuberculosis* Beta-Ketoacyl-Acyl Carrier Protein Synthase III," J. Biol. Chem., 276:20516-20522 [2001].
Shin, S.H., et al., "Complete Genome Sequence of Klebsiella oxytoca KCTC 1686, Used in Production of 2,3-Butanediol ," J. Bacteriol., 194:2371-2372 [2012].

(56) References Cited

OTHER PUBLICATIONS

Smith, M., "In Vitro Mutagenesis," Ann. Rev. Genet., 19:423-462 [1985].

Smits, T.H.M., et al., "Complete Genome Sequence of the Fire Blight Pathogen Erwinia amylovora CFBP 1430 and Comparison to Other *Erwinia* spp.," Mol. Plant Microbe Interact., 23(4):384-393 [2010].

Terpe, K., "Overview of bacterial expression systems for heterologousprotein production: from molecular and biochemicalfundamentals to commercial systems," Appl. Microbiol. Biotechnol., 72:211-222 [2006].

The Uniprot Consortium, "The Universal Protein Resource (UniProt) in 2010," Nucleic Acid Res., 38:D142-D148 [2010].

Tsay, J.T., et al., "Isolation and characterization of the beta-ketoacyl-acyl carrier protein synthase III gene (fabH) from *Escherichia coli* K-12 ," J. Biol. Chem., 267:6807-6814 [1992].

Tsujita, T., et al., "Fatty Acid Alcohol Ester-Synthesizing Activity of Lipoprotein Lipase" J. Biochem. 126:1074-1079 [1999].

Vellanoweth, R.L., et al., "The influence of ribosome-binding-site elements on translational efficiency in Bacillus subtilis and *Escherichia coli* in vivo," M0l. Microbiol., 6: 1105-1114 [1992].

Villa-Komaroff, L., et al., "A bacterial clone synthesizing proinsulin," Proc. Natl Acad. Sci. USA, 75:3727-3731 (1978).

Voelker, T.A., et al., "Alteration of the specificity and regulation of fatty add synthesis of *Escherichia coli* by expression of a plant medium-chain acyl-acyl carrier protein thioesterase," J. Bacteriol., 176:7320-7327[1994].

Wang, H., et al., "Functional Replacement of the FabA and FabB Proteins of *Escherichia coli* Fatty Acid Synthesis by Enterococcus faecalis FabZ and FabF Homologues," J Biol Chem, 279:34489-34495 [2004].

Weil, J., et al. "Pretreatment of Yellow Poplar Sawdust by Pressure Cooking in Water," Appl. Biochem. Biotechnol., 68(1-2): 21-40 [1997].

GenBank Accession No. AAC72881 dated Nov. 11, 1998.
GenBank Accession No. AAA34215 dated Apr. 27, 1993.
GenBank Accession No. AAB71731 dated Oct. 2, 1997.
GenBank Accession No. AAC49151.1 dated Jan. 30, 1996.
GenBank Accession No. AAC49179.1 dated Mar. 6, 1996.
Genbank Accession No. AAC49269 dated Apr. 30, 1996.
GenBank Accession No. AAD38039.1 dated Mar. 30, 2000.
GenBank Accession No. AAMD01000005.1 dated Sep. 28, 2006.
GenBank Accession No. AAQX01001105.1 dated Sep. 1, 2006.
GenBank Accession No. AB236930 dated Nov. 3, 2005.
GenBank Accession No. ABII01000018.1 dated Nov. 30, 2007.
GenBank Accession No. ACC77300 dated Apr. 28, 2008.
GenBank Accession No. ADE86080 dated Jan. 31, 2014.
GenBank Accession No. BAC79425.1 dated Jan. 25, 2012.
GenBank Accession No. CAO22305.1 dated Oct. 8, 2007.
GenBank Accession No. EDD40059.1 dated Apr. 6, 2007.
GenBank Accession No. EU817405.1 dated Mar. 4, 2009.
GenBank Accession No. NM_115529.1 dated Jan. 22, 2014.
NCBI Accession No. NP_215722 dated Dec. 22, 2014.
NCBI Accession No. NP_216703 dated Dec. 22, 2014.
NCBI Accession No. NP_243969 dated Dec. 16, 2014.
NCBI Accession No. NP_388908 dated Mar. 25, 2015.
NCBI Accession No. NP_438551 dated Dec. 16, 2014.
NCBI Accession No. NP_460316 dated Dec. 22, 2014.
NCBI Accession No. YP_045024 dated Dec. 16, 2014.
NCBI Accession No. YP_177983 dated Dec. 22, 2014.
NCBI Accession No. YP_290214 dated Dec. 16, 2014.
NCBI Accession No. YP_350081 dated Dec. 16, 2014.
NCBI Accession No. YP_436183 dated Dec. 16, 2014.
NCBI Accession No.YP_958864 dated Dec. 18, 2014.
NCBI Accession No. ZP_01305629 dated Nov. 26, 2012.
NCBI Accession No. ZP_01892995 dated Nov. 9, 2010.
NCBI Accession No. ZP_07590374 dated Nov. 10, 2010.
UniProtKB Accession No. A6EV17 dated Jul. 24, 2007.
UniProtKB Accession No. P0A6R0 dated May 10, 2005.
UniProtKB Accession No. Q39473 dated Nov. 1, 1996.
UniProtKB Accession No. Q39513 dated Nov. 1, 1996.
UniProtKB Accession No. Q41635 dated Nov. 1, 1996.

\* cited by examiner

Figure 1 – Pathway for the Production of Fatty Alcohols

Figure 2 – Plasmid pCDX11-FAR

Figure 3 – Polynucleotide and Polypeptides sequences

| SEQ ID NO: | DESCRIPTOR | SEQUENCE (5' – 3' – POLYNUCLEOTIDE) |
|---|---|---|
| 1 and 2 | WT-FAR | ATGGCTACTCAACAACAACAGAACGGTGCATCTGCATCCGGCGTCTTGGAACACTTCGTGGAAGCACGTTC<br>TTATCACAGGTACTACCGGGATTTTTGGGCAATAAACGTCATCCAGCCGCTCGTGAACGTTCGTACTGTTCCTGGATATTGG<br>AGGTATTCATCTGCTGATTCGTGTGGCAATAAACGTCATCCAGCCGCTCGTGAACGTTCCTGAACGAAATTGCG<br>TCCTCCCCGTCTTCGAACGTTGCGTCACGATGATAATGAAGCCTTCGAGACCTTCTTGGAAGAACGTGTTC<br>ACTGTATTACCGGTGAGGTTACTGAATCCGTGTTTGGTTTGACACCTGAACGTTTCGTGCTTGGCGGTCA<br>GGTTGACGCTTTTATTAACAGCGCTGAACTTTGCCTGCTCTTGCAGAATTGAAACTCGTCATTGCGGCTATGCGGTGAACTTCGTGAGGAATTGGATAAAGCCCTGAAAATCAAC<br>ACCTTGTGTCTTGAAAATGTTGCCTGCTCTTGCAGAATTGAACTCGTCATTGCCTGGCGGTCATTCAGTTTCCACTTT<br>GTTACGTTAACGGTAAAACTCCGGTACTACGAGATCGAAGAATTGGTCCATCTGTTGATTTGGTTGATTCGGAAGAACAAGATTTCGATGTTAAAGCT<br>TTCCACTGACGGTTACTACGAGATCGAAGAAAAATTGGTCCATCTGTTGATTTGGTTGATCGAAGGCCAATAATTACGGATGGT<br>CGTTACTCCGGCAAAGTTCTGGAGAAATGGTGGGTGAACAACCTTGTCTGGATCGAAAACGTTCGGCATTATTG<br>CCGACACCTACACATTCACCAAATGGTGGGTGAACAACCTTGTCTGGATCGAAAACGTTCGGCATTATTG<br>TATTGTGCGATGCCATTATCTTGGCTTATGCCCTGTTCCCTGGAACTCCATCTCTGTCTGGCTGAGGCGTTGTCTGGTTCTGGTCA<br>GCCGATGCCATTATCTTGGCTTATGCCCTGTTCCCTGGAACTCCATCTCTGTCTGGCTGAGGCGTTGTCTGGTTCTGGTCA<br>ATGTTATTCCTGATTTGGTTGCAGCGGTGGTTCTAATCAACTCAACTGTTTATCGTCGTCCTACTAAACCTTTCGTCGCCG<br>ACGTCGTATTATCAAGACCAACTATGCTGCCTACGATCAACTGTTTATCGTCGTCCTACTAAACCTTTCGTCGCCG<br>GCCGAGGCTAAGACCAACTATGCTGCCTACGATCAACTGTTTATCGTCGTCCTACTAAACCTTTCGTCGCCG<br>TGAACCGTAAATTGTTTGACGTTGTCTGTGGGTATGCGTCTTAAGAACCGTTGATAACGACCCGTCCCTTGCAACCATTTTT<br>TTTTGGCTGGTCAAAATCGTGAGTTGAAAGTGCTTAAGAACCGTTGATAACGACCCGTCCCTTGCAACCATTTTT<br>GGCTTCTCTATACTGCTCCCGACTATATCTTCCGTAACGATAGCTTGATTGGCAGTTGTACTTGTGTAAAATTCATTTGGG<br>TGGATCGTGTTCTTTTCCCAGTTGATGCTCGTCAAATTGATTGGCAGTTGTACTTGTGTAAAATTCATTTGGG<br>TGGTCTGAACCGTTACGCTTTGAAGAACGTAAACTGTATTCTTTGCGTGCTGCTGCTGATACTCGTAAAAAGCT<br>GCCTAA<br><br>MATQQQNGASASGVLEQLRGKHVLITGTFGLGKVVLEKLIRTVPDIGGIHLLIRGNKRHPAAREREFLNEIA<br>SSSVFERLRHDDNEAFETFLEERVHCITGEVTESRFGLTPEREFRALAGQVDAFINSAASVNFREELDKALKIN<br>TLCLENVAALABLNSAMAVIQVSTCYVNGKNSGQITESVIKPAGESIPRSTDGYYEIEELVHLLQDKISDVFKA<br>RYSGKVLEKKLVDLGIREANNYGWSDTYTETKWLGEQLLMKALSGRSLTIVRPSIIESSALEEPSPGWIEGVKV<br>ADAIILAYAREKVSLFPGKRSGIIDVIPVDLVANSILSLAEALSGSGQRRIYQCCSGGSNPISLGKFIDYLM<br>AEAKTNYAAYDQLFYRRPTKPFVAVNRKLFDVVVGGMRVPLSIAGKAMRLAGONRELKVLKNLDTTRSLATIF<br>GFYTAPDIIFRNDSLMALASRMGELDRVLFPVDABQIDWQLYLCKIHLGGLNRVALKERKLYSLRAADTRKKR |

Figure 3 (Cont.)

| SEQ ID NO: | DESCRIPTOR | SEQUENCE (5' - 3' - POLYNUCLEOTIDE) |
|---|---|---|
| 3 and 4 | FAR-V1 | A<br><br>ATGGGCGACTCAACACAGCAGAACGGTGCATCTGCATCCGGCGTCTTGGAACAACTTCGTTGGAAAGCACGTTC<br>TTATCACAGGTACTACCGGATTTTTGGGCAAGTGGTTCTGGCAAAAGTTGATTCGTACTGTTCCGGATATTGG<br>AGGTATTCATCGTCGTGATTCGTTGGCAATAAAACGTCATCCAGCCGCTCGTGAACGTTTCCTGAACGAAATTGCG<br>TCCTCCTCCGTTCGAACGTTGCGTTACTGAATCCCGTTTTGGTTTGACACCTGAGCCGTTTTCGTGCTTTGGCCGGTCA<br>ACTGTATTACCGGTGAGGTTACTACAGCGCTGCAAGCGTGAGTTTTCGTGAGCAATTGGATAAAGCCCTGAAAATCAAC<br>GGTTGACGCGTTTTTATTAACAGGCGGCTGCTCTTCCAGAATTGAACTCCCGTATGGCGGTCATTCAGGTTCCACTT<br>ACCTTGTCGTTCGAAAATGTTCCTCTTCCAGAATTGAACTCCGTCATTAAATCGGCTGGCGAATCCATTCCCCG<br>GTTACGTTAACGGTAAAACTCCGGTCAAATTACCGGAATCCGTCATTAAATCGGCTGGCGAATCCATTCCCCG<br>TTCCACTGACGGTTACTACGAGAATCTGTGATCGAAGAATTGGTCATCTGTGATTTCCGAAGACAAGATTCCGATGTTAAAGCT<br>CGTTACCTGCGCAAAGTTCTGGAGAAATGGTTGGGTGAACAACTGCTGATGAAGAAGGCCTTGTCTGTCGTTCTTTGAC<br>CCGACACCTACAACATTCACCAAATGGTTGGGTGAACAACTGCTGATGAAGAAGGCCTTGTCTGTCGTTCTTTGAC<br>TATTGTCGTCCCTCTATTATTGAGTCCGCTTTGGGAGAACCTTCCCTGTTGGATCGAAGGCGTTAAAGTT<br>GCCGATGCCATTATCTTGGCTTATGCCGGTTGCCGAACTCCATCACTTTGTCCTGGCTGAGGCGTTGTCTGGTTCTGGTCA<br>ATGTTATTCCTGCGATTTGGTTGCCAGCGGTGTGCCTACGACGGTGTTCATCAACGTCTAATCAACTGTTTTATCGTCGTCGTACTAAACCTTTCGTCGGCCG<br>ACGTCGTATTTATCAATGTTGCACGACCAACTATGCGTTCTGCCTACGACTTGTTCGTGCTTGAAAGTTGCTTAAGAACCTGATAGCTTGATGGCCTGGCGTATGCGT<br>GCCGAGCGTAAGACCAACTATGCGTTCTGCCTACGACTTGTTCGTTGAAAGTTGCTTAAGAACCTGATAGCTTGATGGCCTGGCCGTAGGCGTATGGGTAAT<br>TGAACCGGTAAATTGTTTGACGTTGAGTTGTGAAATCGTGAGTTGAAAGTGCTTAAGAACCTGATAGCTTGATGGCCTGGCCGTATGGGTAAT<br>TTTGGCTGGTGTAAATCGTGAGTTGTAAATCTTCCGTAACGATAGCTTGATGGCCTGGCCGTATGGGTAAT<br>GGCTTCTATACTGCTCCCCGACTATATCTTCCGTAACGATAGCTTGATGGCCTGGCCGTATGGGTAAT<br>TGGATCGTGTTCTTTTCCCAGTTGATGCTCGTCAAATTGATTGGCCAGTTGTACTTGTGTAAATTCATTTTGGG<br>TGGCTCTGAACCGTTACGCTTTGAAGGAACGTAAACTGTATTCTTCCGCGTGCTGCTGATACTGACGATAAACC<br>GCCTAA<br><br>MATQQQNGASASGVLEQLRGKHVLITGTTGFLGKVVLEKLIRTVPDIGGIHLLIRGNFKRHPAARERFLN<br>EIASSSVFERLRHDDNEAFETFLEERVHCITGEVTESRFGLTPERFRALAGQVDAFINSAASVSFREQLD<br>KALKINTLCLENVAALAELNSAMAVIQVSTCYVNGRNSGQITESVIKSAGESIPRSTDGYYEIEELVHLL<br>QDKISDVKARYSGKVLEKKLVDLGIREANNYGWSDTYTFTKWLGEQLLMKALSGRSLTIVRPSIIESALE |

Figure 3 (Cont.)

| SEQ ID NO: | DESCRIPTOR | SEQUENCE (5' – 3' – POLYNUCLEOTIDE) |
|---|---|---|
| 5 and 6 | FAR-V2 | EPSPGWIEGVKVADAIILAYAREKVSLFPGKRSGIIDVIPVDLVANSIILSLAEALSGSGQRRIYQCCSG GSNPISLGKFIDYLMAEAKTNYAAYDQLFYRRPTKPFVAVNRKLFDVVVGGMRVVLSIAGKAMRLAGVNR ELKVLKNLDTTRKLATIFGFYTAPDIIFRNDSLMALAQRMGELDRVLFPVDARQIDWQLYLCKIHLGGLN RYALKERKLYSSRAADTDDKTA<br><br>ATGGCGACTCAACAACAGAACAGAACAACGGTGCATCCGGCGTCTTGGAAATTCTTCGTGGAAAGCACGTTC TTATCACAGGTACTACCGGATTTTGGCAAAGTGGTTCTGGAAAAGTTGATTCGTACTGTTCCGGATATTGG AGGTATTCATCTGCTGATTCGTGGCAATAACCTGCCAGCCGCGCTTGCCGAACGTTTCCTGAACGAAATTGCG TCCTCCTCCGTCTGAACGTTTGCGTCACGATGATAATGAAGCCCTTCTTGGAAGAACGTGTTC ACTGTATTACCGGTGAGGTTACTAGCGCTGAACTGAATTCGTGAACAATTCGTGAGCAATTGGATAAAGCCCTCAGTTCCACTT ACCTTGTGTCTCTGAAAATGTTGCTGCCGGATCAAATTACCGAACTCCGTCATTAAATCGGCTGGCGAATCATTCCCG GTTACGTTACGGTTATTACCCGGTCAAATTACCGAATCCGTCATTAAATCGGCTGGCGAATCATTCCCG TTCCACTGACGGTTACTACGAGATCGAAGAAAAAATGGTTGGTTGAACAACTGCTGATGAAGGCCAATAATTACGGATGGT CGTTACTCCGGCGTACACAATTCACCCAAATGGTTGGTTGAACAACTGCTGATGAAGGCCAATAATTACGGATGGT CCGACACCTACACAATTCACCCAAATGGTTGGTTGAACAACTGCTGATGAAGGCCAATAATTACGGATGGT TATTGTGCCTCCCTCTATTATTCGGCTTATGAGTCCCGTTGAACTTCCCCTGCCTGAAAGTCGTTAAAGTT GCCGATGCCATTATCCGTCGATTGGTTGCAGCGGTGGTTCTACGTTGTTGGTCTACGGTTGGTCTGGTCA ATGTTATTCCGTCTATTTATCAATGTCGACTACTGCGCCTAGTTGTTGGTCGTCCCTACTAAACCTTCGTCGCCG ACGTCGTATTTATCAATGTCGACTACTGCGCCTAGTTGTTGGTCGTCTTCTATTGCCGTAAGCTATGCG GCCGAGCGTAAGACTATGCGCGACGTTGTTGGTCGAGTTGCACGTAGAACGTTCGTGCCCCGTAAACCATTTTT TGAACCGTAGTTGTTGACGTTGTTGACGCCTGTTCTGTCCATGCGTGTGTTGTCCTTTCTATTGCCGTAAACCCG TTTGGCTGGTGGTAAATCGGTGACGTTGAGTTGAAAGTGCTTAAGAACCTTGATGACGATAGCTTTGATGGCCCTGGCCTTGTACTTGTGTAAAATTCATTTGCG GGCTTCTATACTGCTCCCGACTATATCTTCCGTAACGATAGCTTTGATTGGCAGTTGTACTTGTGTAAAATTCATTTGCG TGGATCGTGTTCTTTTTCCCAGTTGCATGATGCTCGTCAAATTGAAGCTAAACTGTATTCTTCGCGTGCTGCTGATACTGACGATAAAACC GCCTAA<br><br>MATQQNNGASASGVLEILRGKHVLITGFTGFLGKVVLEKLIRTYPDIGGIHLLIRGNKRHPAAGEREFLNEIA SSSVFERLRHDDNEAFETFLEERVHCIITGEVTESRFGLTPERFRALAGQVDAFIHSAASVNFREQLDKALKIN TLCLENVAALAELNSAMAVIQVSTCIVNGKTSGQITESVIKSAGESIPRSTDGYYEIEELVHLLQDKISDVFKA RYSGRVMGKKLVDLGIREANNYGWSDTYTFTKWLGEQLLMKALSGRSLTIVRPSLIIESALEEPSGWIEGVKV |

Figure 3 (Cont.)

| SEQ ID NO: | DESCRIPTOR | SEQUENCE (5' - 3' - POLYNUCLEOTIDE) |
|---|---|---|
| 7 and 8 | FAR-V3 | ADAIILAYAREKVSLFPGKRSGIIDVIPVDLVANSIILSLAEALSGSGQRRIYQCCSGGSNPISLGKFIDYLN AEAKTNYAAYDQLFVRRFTKPFVAVNRKLFDVVVGVMRVVLSLAGKAMRLAGVNRELKVLKNLDTTRKLATIF GFYTAPDYIFRNDSLMALAQRMGELDRVLFPVDARQIDWQLYLCKIHLRGLNRYALKERKLYSSRAADTDDKT A<br><br>ATGGGACTCAACAACAACAACGGTCACTGCATCCGGCGTCTCTTGGAAATTCTTCGTGGAAAGCACGTTC TTATCACAGGTACTACCGGGATTTTGGCAAAGTGGTTCTGGAAAAAGTTGATTCGTACTGTTCCGGATATTGG AGGTATTCATCTGCTGATTCGTGGCAATAAACGTCATCCAGCCGCTCGCGAACGTTCCTGAACGAAATTGCG TCCTCCTCCGTCCGTCTTCGAACGTTTGCGTCACGATGATAATGAACTTTGTTGACACCTGAGCCGTTTTCGTGCTTTTGGCCGGTCA ACTGTATTACCGGTGAGATTACTGAAATCCCGTTTTGGTTTGACACCTGAGCCGTTTTCGTGCTTTTGGCCGGTCA GGTTGACGCTTTTATTCATAGCCGCTGCTCGTTGCAAGCGTGAGTTCGTGAGCAATTGGATAAAGCCCTGAAAATCAAC ACCTTTGTGTCTTGAAAATGTTGCTCCCGGTAAAACTCCCGGTCATAACTCCGTCATTAAATCGGCTGGCGAATCCATTCCCG GTTACGTTAACGGTTACTACCGAGATCGAAGAATTGGTCCATCTGTTGCAAGACAAGATTTCCGATGTTAAAGCT CGTTACTCCGGCCGTGTTATGGGGAAAATGGTTGGGCTTTGGGTCTTTGGTGGATTCGTGAGGCCAATAATTACGATGGT CCGACACCTACACATTCACCAAATGGTTGGGCTTTGGGTGAACAACTGCTGTTCCCTGTTCCCTGGCTGAGGCGTTCGGCATTATTG TATTGTGCGTCCCCCTCTATTATTGGCTTTAGCGATTTGGTTGAAAAAGTTAGCCTGTTCCTGGAAAAACCTTCCGGCATTATTG ATGTTATTCGTGATTCGGTTCGGATGTTGCAGCGGGTTTGGTTCTAATCCATCATCTTGTCCCTGGGCAAGTTCATTATTTGAAC ACGTCGTATTTATCATGTTGCAGCGGGTGGTTCTAATCCATCATCTTGTCCCTGGGCAAGTTCATTGATTATTTTGAAC GCCGAGCGTAAAGACCAACTATGCTGCTAACTATGCTGGGTCTACGACTCGTCGACATGCGACATGCGACATGCG TGAACGGTAAATTGTTTGACCTGCGTTGTTGGTGTCATCTGTTGACCGTGTTGTTCCTTTCATTGACCCCGAAAACGTATGCG TTTGGCTGGTGTAAATCGTGAGTTGAAGTGCTTAAGAACCTTGATAACCCGTAACTTCTCTAACCTTGCAACCATTTTT GGCTTCTATACTGCTCCCGACTATATCTTCCGTAACGATAGCTTGATGGCCCTGGCTGTACTTGTGTAAAATTCATTGCG TGGATCGTGTTCTTTCCCAGTTGATGGCGTGAGTTGATAGCTTGATGGCAGTTGATGTACTTGTGTAAAATTCATTGCG TGGGTGCTGAACCGTTACGCTTTGAACGTAGAACGTAAACCTGTATTCTTCCGCTGCTGCTGATACTGACGATAAAACC GCCTAA<br><br>MATQQNNGASASGVLEIIRGKHVLITGFTLGFTLGKVVLEKLIRTVPDIGGIHLLIRGNKRHPAARERFLNEIA SSSVFFERLRHDDNEAFETFLEERVHCITGEITESRFGLTPERFRALAGQVDAFIHSAASVNFREQLDKALKIN TLCLENVAALAELNSAMAVIQVSTCTVNGKTSGQITESVIKSAGESIPRSTDGYYEIEELVHLLQDKISDVKA RYSGRVMGKKLVDLGIREANNYGWSDIYFTKWLGEQLLMKALSGRSLTIVRPSIIESALEEPSPGWIEGVKV |

Figure 3 (Cont.)

| SEQ ID NO: | DESCRIPTOR | SEQUENCE (5' – 3' – POLYNUCLEOTIDE) |
|---|---|---|
| | | ADAIILAYAREKVSLFPGKRSGIIDVIFVDLVANSIILSLAEALSGSGQRRIYQCCSGGSNPISIGKFIDYLN AEAKTNIAAYIDQLFYRRPTKFFVAVNRKLFDVVYGVMRVVLSIARKAMRLAGVNRELKVLKNLDTTRKLATIF GFYTAPDYIFFRNDSLMALAQRMGELDRVLFPVDARQIDWQLYLCKIHLRGLNRYALKERKLYSSRAADTDDKT A |
| 9 and 10 | FABH | ATGTATACGAAGATTATTGGTACTGGCAGCTATCTGCCCGAACAAGTGCGGACAAACGCCGATTTGAAAAAA TGGTGGACACCTCGACGAGTGGATTGTCACTCGTACCGGTGCCGAACGCCACATTGCCGGCCAAACGA AACCGTTTCAACCATGGGCTTTGAAGCGGCGACACGCGACACGCGGCATTGAGATGGCGGGCATTGAGAAAGACCAGATT GGCCTGATCGTTGTGGCAACGACTTCTGCTACGCACGTTCCCGAGCGCAGCTTGTCAGATTCAAAGACATGT TGGGCATTAAAGGTTGCCCGGCATTTGACGTTGCCAGCAGCCTGCACGCTCGGTCGTCGATTCATTATGCATTAAGCGTAGC CGATCAATACGGTGAAATCTGGGCCGGTATTATTATTTTTGGCGACGTATGCCTCCGATGTACTGGCGCGACCTGC GATCCAACCGATCGTGGGACTATTACCCCATCTGCAFGCCCGACGGTAGTTATGGCGACGGCTGCCAAACGCCGA AGCCGGGAATCATTTCCAGACGCCATCTCATGCCGCAGGATGGCGCGGGCAACGAAGTCTTCAACTGGACTGGTTCCGC CTGGCCCACATCGTTGATGAGACGCCTGTATTATCAGTGCAACGGCGAATAATCTCGGTACTGTCTATGGATAATGTCGTGGTGAC ATCAGGCTAACCTGCGTATTACTTGATACCTCCTCTGCGCAGGGTAGTTCCCTTGCTTGAAGCCTTTGGCGGTGGATTCACCTGGGCGCTCCGCGCTGGTTCGTT ATTAAGCCGGGGCAGTGGTTCTGCCTTGAAGCCTTTGGCGGTGGATTCACCTGGGCGCTCCGCGCTGGTTCGTT TCTAA |
| 11 and 12 | TE | MYTKIIGTGSYLPEQVRTNADLEKMVDTSDEWIVTRTGIRERHIAAPNETVSTMGFTRATRAIEMAGIEKDQI GLIVVATTSATHAFPSAACQIQSMLGIKGCPAFDVAAACAGFTYIALSVADQYVKSGAVKIALVVGSDVLARTC DPTDRGTIIIFGDGAGAAVLAASEEPGIISTHLMADGSYGELILTLPNADRVNPENSIHLTMAGNEVFKVAVTE LAHIVDETILAANNLLDRSQLDWLVPHQANLRIISATAKKLGMSMDNVVTLDRHGNTSAASVPCALDEAVRDGR IKPGQIMVLLFRAFGGGFTWGSALVRF |
| | | ATGACAATCATTACGCCCGAGCTCTGAACTCACCCTTACGAAAGGGAATAAAGCTGGTCATCGACAGCTGTAG CTGCCCGCTTTAGAGTGGAGAACCAAAACCGAAATTACCTCAGCTTCTTGACGACCACTTCGGCCTGCATGGTTT AGTATTCCGCAGAACGTTTGCCATAAGAAGCTACGAAGTAGGACCAGATCGTTCTACCTCTATACTTGCTGTG ATGAATCATTATGCCAGGAAGCCACCGTTAAATCACGCAAAGAGCGTCGGGACTCCTGGGACGGATTCGGCACCA CATTGGAAATGAGTAAGCGGGACCTGATGTGGGTTGTTCGTCGTACCCACCGTAGCCGTCGAACGTATCCAAC |

Figure 3 (Cont.)

| SEQ ID NO: | DESCRIPTOR | SEQUENCE (5' – 3' – POLYNUCLEOTIDE) |
|---|---|---|
| 13 and 14 | FADE | ATGGGCGATACTGTTGAAGTGGAAGTGCTGGAGTTGGGCCTTCCGGAAACAACGGAATGCGCAGAGATTTTCTG GTGCGGGACTGTAAAACTGGGGAAAACTTAACGCGCGTTGGATCGCCCCTGTACCCTCCGTTCTGATGAACACGCGTACCC GGAGATTAAGTACGATTCCGGACGAAGTCCGTGGTGAAATCGGTCCCGCTTTTATTGACAACGTGGCGGTAAA AGACGACGAAGCGAGATCAAAAAGTTGCAGAAATTGAACGATTCCACAGCAGATTACATACAGGGCGGTCTTACGCCC CGTTGAACGACGACTTGGATGTGAATCAGCACGCACATTCCAGCTTTACGCTGGAGTACAGACGCGAGTGTACGCGCGATTC CCGACTCTATTTTTGAAAGTCACCACGGTGTCTGGCGGATCTTCCGAAGCTGGGTTAGTGTGTGATCACTTGCTGCAA CGTTTTACGTTCCCTCACCACGGTGTTCTCGGGCCCGACGGAAATGCCGTCCCAAACTGACCCTTCCTTCCGCGGAA CTTGAAGGCGGAAGTGAAGTTCTTCGGGCCCACGGAAATGCCGTCCCAAACTGACCCTTCCTTCCGCGGAA TATCAGTAATTCCGGCCGAGCCCGCGGGTATAA MTMITPSSELTLTKGNKSWSSTAVAAALEWKPKPKLPQLIDDHFGLHGLVFRRTFAIRSYEVGPDRSTSILAV MRNRMQEATINHAKSVGILGDGFGTTLEMSKRDLMRVVRTHVAVERYPTWGDTVEVECWIGASGNNGMRDFL VRDCKTGEILTRCTSLSVLMNTRRTRRLSTIPDEVRGEIGPAFIDNYAVKDDEIKKLQKLNDSTADYIQGGLTP RWNDLDVNQHVNNLKYVAWVFETVPDSIFESHHISSFTLEYRRECTRDSVLRSLTTVSGGSSEAGLVCDHLLQ LEGGSEVLRARTEWRPKLTDSFRGISVIPAEPRV |
|  |  | ATGATGATTTTTGAGTATTCTCGCTACGGTTGTCCTGCTCGGCGCGTTGTTCTATCACCGCGTGAGCTTATTTA TCAGCAGTCTGATTTTGCTCGCCTGGACAGCCGCCTCGGCGTTGCTGGTCTGTGGTCGGCGTGGGCGTGGGTACTGGT GCCTCTGGCCATTATCCTGCGTGCCATTTAACTTTGCGCGCCTATGCGGTAAGTCGATGATGATTTCCGCGCCGGTATTT CGGGCGGTTCCCGTAAGGGTGATGCCGGAAGCCGGACTGTCGCGACTGAGAAAGAAGCGATTGATGCGGGCCACCACCTGGT GGGAGGGCCGACTTGTCAGGGCGAAGCCGGACTGTCGCCGGTGTGGGTGGCCAGCCGCCCGCCCCTGACCGC CGAAGAGCAAGCGTTTCTGCCCCGGCTGGAGTTCTCGGCTGTGGGCGTACCCTAAAGAGGCATCGCGTTCTTCCGCGATGATCATCAAAA GAGCTGGCGGATCCTGCGGGGCTGGGGAAGAGGCATCGTGCCGGATGGCGTACCTAAAGAGGCATCGCGCTGCCGTGCGCCGGGTACCTGAAC AAGAGTACGGCGGATTACCGTGCCGGGCTGGAGTTCTCCGGCCTGCCGTGCCCAGTCGCGTGCCGTGCCCAGTGTTGCAACATTACGGCACTGAC GATCCTGGCGATTACCGTGCTATCTGCCGGGCTGGAGTCCCGGGATTGTCTGCACCGATTGCCGACCGTTGCAACATTACCGCACCGGCACTGAC GAGCAGAAAGATCACTATCTGCCGGGCTGGAGATCCCGGGGATTGTCTGCACCGATTGCCGACCGTTGCTGCCGTGCCAGCCAGCCGCGG AAGCGGGTTCCGATGCCGTCTGACCCTGGAACCAAACGCTACATTCGGCCGATTGCCGACCGTTGCTGCCGTGCCAGCCAGCCAGGT GCTGGGGATGCGTCTGACCCCGGTGCAAAATTGGTCGTCGCCGATTACATCATCCGGGCGGCCGAGGGCCCGATCCCCAA TTTAAACTCCGCGGGCGTGGAAAAATTGGTCGTCGCCGATTACATCATCCGGGCGGGCCTCCAGAACCGACCGACGCG CCACCACGCGCGGGGCGTGGAAAAATGGTCGTCGCCGATTACATCATCCGGGCGGGCCTCCAGAACCGACCGACGCG CGGTAAAGATGTCTTCGTGCCGATTACCGATTACATCATCCGGGCGGGCCTCCAGAAATGGCCGGGCAAGGCTGGCGGATG CGGTGGAGTGCCTCTCGGTAGGCCGCGCCATGACCGCCTTCAACCTCACCACCGTCAGTTCCAAAATCGCGGCTGTGAAATCGGTAG CGCTGGCAACCCGGCCGTATGCCGTCACATTCGCCGTCAGTCAGTTCAAAATCTCTATTGGTAAGATGGAAGGGATTGA |

Figure 3 (Cont.)

| SEQ ID NO: | DESCRIPTOR | SEQUENCE (5' – 3' – POLYNUCLEOTIDE) |
|---|---|---|
| | | AGAGCCCTGGCCGGTATTGCCGGTAATGCCTACGTGATGGATGCTGCGGCATCGCTGATTACCTACGGCATT<br>ATGCTCGGCGCAAAACCTGCCGCCGTCGTGTCGGCTATCGTTAAGTACTGTACCACCGGGCAGCAGTCGA<br>TTATTGATGCGATGGATATTACCGGCGATTGCCATCACCGGTAAAGCATTATGCTCGGGCAAAGCACTTCCTGGCGCGTCTTA<br>CCAGGCGCCATTGTTGCCATCCGTACCGTGCTGCTGGAAGAGATGGAAGCGGCAGCATGATGACAATGACGTCAACGCGTTCG<br>GGAGCGATTCGTTGTTCAAAACATATCGGTCACGTCGGTAGCAACAAAGCTACTATCAGCACCTGAAACCGCCTGAGCGCC<br>CGGTTTAACCAGCAGCACGCCAACCGGCGATGCCACTAAACGCTACTATCAGCACCTGAAACCGCCTGAGCGCC<br>AACCTCGCCCTGCTTTCGATGTCTCGATGGCAGTGCTGGGCGGCAGCCTGCTGAAAACGTCGCGACGAAGGCCG<br>CCCGTCTGGGGGATATTTTAAGCCAGCTCCACTGGGGCGTACAAGATGCGCTGTATCAGGCTGAACAGGCGATGGAT<br>TAATGAAGCCGACCTGCCGCTGGTGCCACTGGGGCGTTGCCGGGCGTACAAGATGCGCTGTATCAGGCTGAACAGGCGATGGAT<br>GATTACTGCAAAACTTCCCGAAACCGCTGGTTGCCGGGCGTGCTGAATGTGGTGATCTTCCCGACCGGACGTC<br>ATTATCTGGCACCTTCTGCGGTCAGTACCTGACGCCAGCCAGGTGATCATAAGGTGGCGAGCAGATAATCCGGTTGGCTTGGCTAAAACCTGCCGTTTACCGTG<br>CCGCATTGGTCCGCGCCAGTACCCAATTCATCAGCGACCTCGTAAGAGCTGAAAGATGAAGCCGCTATTCTGGTGAAAGC<br>GATGTGATTGCCGCCGACCCAATTCATCAGCGACCTCGTAAGAGCTGAAAGATGAAGCCGCTATTCTGGTGAAAGC<br>TGGATGAACTGGCCGCACAACGCGCTGGTGAAGGGCTGATTGATAAACGTTGATGACTTTGATCCGGAAGAGCTGGCGACGAAGCCGGTAAAG<br>TGAAGAAAGCCGTCTCGCCAGTATAACGTTGATGACTTTGATCCGGAAGAGCTGGCGACGAAGCCGGTAAAG<br>TTGCCGGAGAAAGTGCCGGAAAAGTTGAAGCCGCGTAA<br><br>MMILSILATVTLLGALFTHRVSLFTSSLIILAWTAALGVAGLWSAWVLVPLAIILVFFNFAPMRKSMISAPVF<br>RGFRKVMPPMSRTEKEAIDAGTTWWEGDLFQGKPDWKKLLHNYPQPRLTAEEQAFLDGPVEEACRMANDFQITH<br>ELADLPEELMAYLKEHRFFAMIIKKEYGGLEFSAYAQSRVLQKLSGVSGILAITVGVPNSLGPELLQHYSTD<br>EQKDHYLPFRLARGQEIPCFALTSPEARGSDAGAIPDTGIVCMGEWGQQVLGMRLTWNKRYITTLAPIATVLGLA<br>FKLSDPEKLLGGAEDLGINCALIPTTTPGVEIGRRHFPLNVFFQNGPTRGKDVFVPIDYIIGGPKMAGQGWRM<br>LVECLSVGRGITLPSNSTGGVKSVALATGAYAHIRRQFKISIGKMEGIEEPLARIAGNAYVMDAAASLITYGI<br>MLGEKPAVLSAIVKIHCTHRGQQSIIDAMDITGGKGIMLGQSNEFLARAYQGAPIAITVEGANILTRSMMIFGQ<br>GAIRCHPYYVLEEMEAAKNNDVNAFDKLLFKHIGHVGSNKVRSFWLGLTRGLTSSTPTGDATKRYIQHLMRLSA<br>NLALLSDYSMAVLGGSLKRRERISARLGDILSQLYILASAVLKRYDEGRNEADLPLVHWGVQDALYQAEQAMD<br>DLLQNFPNRVVAGLLNVVIFPTGRHYLAPSDKLIDHKVAKILQVPNATRSRIGRGQYLTPSERHFPVGLLEEALV<br>DVIAADPIHQRICKELGKNLFFTRLDELAAHNALVKGLIDKDEAAILVKAEESRLRSINVDDFDPEELATKPVK<br>LPEKVRKVEAA |

Figure 3 (Cont.)

| SEQ ID NO: | DESCRIPTOR | SEQUENCE (5' - 3' - POLYNUCLEOTIDE) |
|---|---|---|
| 15 and 16 | FADD | ATGAAGAAGGTTTGGCTTAACCGTTATCCCGCGGACGTTCCGACCGGAGATCAACCCTGACCGTTATCAATCTC<br>TGGTAGATATGTTTGAGCAGTGAGTTCCGCGCGCTACGCCGGATCAACCGCGTTTGTGAATATGGGGAGGTAAT<br>GACCTTCCGCAAGCTGGAAGAACGCAGTGCCGCGTTGCCGCTTATTTGCAACAAGGGTTGGGGCTGAAGAAA<br>GGCGATCGCGTTGCGTTGATGATGCCTAATTTATTGCAATATCCGGTGGCGCTGTTTGGCATTTGCGTGCCG<br>GGATGATCGTCGTAAACGTTAACCGTTGTATACCCCGCGTGAGCTTGACGCATCAGCTTAACGATAGCGGCGC<br>ATCGGCGATTGTTATCGTGTCTAACTTTGCTCTAACACACTGGGGAAAAAGTGGTTGATAAAACCCGCTCAGCAC<br>GTAATTCTGACCCGTATGGGCGATCAGCTATCTGCCAGATGCCATTTCATTTCGTAGCGCACTGCAATTTCGTTGTTAAATACA<br>TCAAGCGTTTGGTGCCGAAATACCGAACTGGTGCCGGAAGATTTAGCTTTCTCGAACACAGGTTAACGCGACCACTGGTC<br>GATGCAGTACGTCAAAACCGCGATGCTGACTTCACCGGACAATATGCTGGCGACCTGGAAACACAGGTTAACGCGACCACTATGGTC<br>GTGGCGAAAGGCGCGATGCTGACTTCACCGGACAATATGCTGGCGACCTGGAAACAGGTTAACGCGACCACTATGGTC<br>CGCTGTTGCATCCGGGCAAAGACTGGTGGTACGCAGAACCTGCTTATCACAACCCGCGCGATATTCCAGGGTTGGTA<br>AAAGAGTTAGCGAAATATCCGGATTTCTCCAGTCTGCATCTTCCGCAGGCCGGTGGGATGGCCTTACCGAGTGCGCGCTG<br>AAGAGTTCCAGCAGCCGTTGGGTGAAACTGAACCGGACAGTATCTGCTGGAAGGCTATGGCCTTACCGAGTGTGCCGCTG<br>GGCAGAGCGTTGGGTGAAACTGAACCGGACAGTATCTGCTGGAAGGCTATGGCCTTACCGAGTGTGCCGCTG<br>GTCAGCGTTAACCCATATGATGATTATTGATTAATCATAGTGGTAGCATCGGTTTGCGGTGCCGTGCGACGGAAGCCA<br>AACTGGTGGATGATGATGATAATGAAGTACCACCAGGTCACACCGGGCTTTGTGTCAAAGGACCGCAGGT<br>GATGCTGGGTTACTGCCAGCGTCCGATTGTTGATGGATCGTTGATGTGTGATCGTAAAAAAGACATCATCAAAATGGCTGGTTACACACCGGCGAC<br>ATCCGCGTAATGGATGAAGAAGGATTCCTGCGCAGTCTGATCGATCGTAAAAAAGACATGATTCTGGTTTCCGGTT<br>TTAACGTCTATCCGGCTCCAACGAGATTGAAGATGTGTCATGCAGCATCCTGGCGTACAGGAAGATCCATCGCTTACCGAAGAG<br>CGTACCTTCCGGCTGACTTTTTGCCGCCGTCAGCTGACAAAGTACCCAAGCTGGTGGAGTTTCGTGATGAGT<br>TCACTGGTGACTTTTTGCCGCCGTCAGCTGACAAAGTACCCAAGCTGGTGGAGTTTCGTGATGAGT<br>TACCCGAAATCTAACGTCGGAAAATTTTGCGACGAGAATTACGTGACGAAGCCGCGGCAAAGTGGACAATAA<br>AGCCTAA<br><br>MKKVWLNRYPADVPTEINPDRYQSLVDMFEQSVARYADQPAFVNMGEVMTFRKLEERSRAFAAYLQQGLGLNK<br>GDRVALAMPNLLQYFVALFGILRAGMIVVNVNPLYTPRELEHQLNDSGASAIVIVSNFAHTLEKVVDKTAVQH<br>VILTRMGDQLSTAKGTVVNFVVKIKRLVPKYHLPDAISFRSALHNGTRMQYVKPELVPEDIAFLQYTGGTTG<br>VAKGAMLTHRNMLANLEQVNATVGPLLHPGKELVVTALPLYHIFALTINCLLFIELGGQNLLITNPRDIPGLV<br>KELAKYFFTAITGVNTLFNALLNNKEFQQLDFSSLHLSAGGEMPVQQVVAERWVKLTGQVLLEGYGLTECAPL<br>VSVNPYIDIDYHSGSIGLFVPSTEAKLVDDDDNEVPPGQPGELCVKGPQVMLGYWQRPDATDEIIKNGWLHTGD |

Figure 3 (Cont.)

| SEQ ID NO: | DESCRIPTOR | SEQUENCE (5' - 3' - POLYNUCLEOTIDE) |
|---|---|---|
| 17 and 18 | FABG | IAVMDEEGFLRIVDRKKDMILVSGFNVYPNEIEDVVMQHPGVQEVAAVGVPSGSSGEAVKIFVVKKDPSLTEE SLVTFCRRQLTGYKVPKLVEFRDELPKSNVGKILRRELRDEARGKVDNKA<br><br>ATGAATTTGAAGGAAAAAATCGCACTGGTAACCGGTGCGAAGCCGGTGCCGCGGAATTGGCCGCGGCAATTGCTGAAACGC TCGCAGCCCGTGGCGCGAAAGGTTATTGGCACCAGTGAAAATGGCGCTCAGGCGATCAGTGATTATTT AGGTGCCAACGGCAAAGGTCTGATGTTGAATGTGACCGACCGGCATCTATGAAATCTGTTCTGGAAAAAATT CGCGCAGAATTTGGTGAAGTGGAACGATATTATCGAAAACGAACCTTTCATCTGTTTTCCGTCTGTAATGCGAA TGAAAGATGAAGAGTGGAAACGATATTATCGAAAACGAACCTTTCATCTGTTTTCCGTCTGTAAAGCGGTAAT GCGCGCTATGATGAAACTACGCTGCGGCGAAAGCGGGCTTGATCGGCTTCAGTAAATCACTGGCGCGCGAAGTTGCGT GGTCAGGCCAACTACGCTGCGGCGAAAGCGGGCTTGATCGGCTTCAGTAAATCACTGGCGCGCGAAGTTGCGT CACGCGGTATTACTGTAAACGTTGTGCTCCGGGCTTTATTGAAACGGACATGACACGTGCGCAACGCGGTT CCAGCGTGCGGGTATCTGCCGCAGGTTCCTGCCTGGGCGCCTGGCGGTGCACAGAGAAATCGCCAACGCGGTT GCATTCCTGGCATCCGACGAAGCAGCTTACATCACGGGTGAAACTTTGCATGTGAACGCGGGATGTACATGG TCTTAA |
| 19 and 20 | FABI | MNFEGKIALVTGASRGIGRAIAETLAARGAKVIGTATSENGAQAISDYLGANGKGLMLNVTDPASIESVLEKI RAEFGEVDILVNNAGITRDNLLMRMKDEEWNDIIETNLSSVFRLSKAVMRAMMKKRHGRIITIGSVVGTMGNG QQANYAAAKAGLIGFSKSLAREVASRGITVNVVAPGFIETDMTRALSDDQRAGILAQVPAGRLGGAQEIANAV AFLASDEAAYITGETLHVNGGMTMV<br><br>ATGACCCGCAGGACTGATGGCTGGCAAACGTGGACTGATTATGGGCCTGGCCAATGATAAATCGCGTGGG GCATTGCTAAAGCACTGGCTGATGCAGGTGGCGGAACTGGCGTTTTCTTACCAGGGTGAAGCACTGAAGAAGCG TGTTGAACCACTGGCTGCAAGCCTGGGGGACTGCACCCGCTGTTATTCGAATGTGATGTGGCAAACGAAGACTCAATG GACGCCCTGTTTGCGGGACTGCAAGCCTGGGGGACTGCACCGCATGGGGCGGTAATTTCACGATGACGATGACATTTCAGT ATAAAACGAACTGCGCGGTCGTTTCGCACCCGCGCATTATAACGTTATGGGTGTGCGAAAGCTGCCGTTGAAGCAAGCG GTATAGCTTACTGCGCGTGTTCGCACCCGCGCATTATAACGTTATGGGTGTGCGAAAGCTGCCGTTGAAGCAAGCG TACTATGGAGCCGAACAGTAATGCCCAAACTGGGCAAACTGGGCATTCGTTGTAATGCTATCTCGGCTGCCGATTAAAAC CCTGGCTGCCAAGGACGCGGCATTGGCGACTTTCGCTAATATCATGAAGTGGAACGAGCTGAACAGCCGCTGAACAGC AACGTTACCCAGGAAGAAGTTGGCAAAGCCGGTTACCACCTGTCGTGCCATGAAAGCGGTTGATGCGCCGGAT CAGCCACCACCGGTG AAAACCTGCCATGTGGATGCGGTTACCACCTGTCGTCGCCATGAAAGCGGTTGATGCGCCGGATATTGACGTAGT CACGGGTCGTAAAGACTAA |

Figure 3 (Cont.)

| SEQ ID NO: | DESCRIPTOR | SEQUENCE (5' - 3' - POLYNUCLEOTIDE) |
|---|---|---|
| | | MTAGLMAGKRGLIMGLANDKSIAWGIAKALGDAGAELAFSVQGEALKKRVEPLAASLGTPLLFECDVANEDSM DALFAGLKDAWGTLDFVVHAIGFSDKNELRGRYVDTSRGNFTMTMDISVISFTAVCARAAAMPNGGSLLTLI YYGAEQVMPHYNVMGVAKAALEASVKYIAEDLGKLGIRCNAISAGPIKTLAASGIGDFRYIMKWNELNSPLRR NVTQEBVGKAALYLLSDLGSGTTGENLHVDAGYHVVGMKAVDAPDIDVVTGRRD |
| 21 and 22 | FABZ | ATGACTACTAACACTCTGCAGATTGAAGAGATTTAGAACTTCTGCCGCACCGTTTCCGTTCTTAC TGGTGGATCGCGTGCTGGATTTTGAAGAAGGTCGTTTTCTGCGCCAGTAAAAAATGTCTCTGTCAATGAGCC AFTCTTCCAGGGCCATTTCCCTGGAACACCGATTTCCCGGGTGTGCGATTCTGAAGCAATGGCACAGGCA ACAGGTATTCTGGCGTTTAAAAGCGTAGGAAAAACTGGAACCGGGTGAGCTGTACTACTTCGCTGTATTGACG AAGCGCGCTTCAAGCGCCCGTCGTGCCTGCGATCAAATGATCATGGAAGTCACTTTGCGAAAAAACGCCG CGGCCTGACCCGTTTTAAAGGGGTTGCTCTCTGGTCGATGGTAAAGTAGTTTGCGAAGCAACGATGATGTGCT CGTAGCCGGAGGCCTAA |
| | | MTTNTHTLQIEEILELLPHRFPFLLVDRVLDFEEGRFLRAVKNVSVNEPFFQGHFPGKPIFPGVLIEAMAQA TGILAFKSVGKLEPGELYYPAGIDEARFKRPVVPGDQMIMEVTFEKTRGLTRFRGVALVDGKVVCEATMMCA RSREA |
| 23 and 24 | FADR | ATGGTCATTAAGGCGCAAAGCCCCGGCCAAAGTATTCTGGAATAACCGCT TCCCTCCCGGGACTATTTGCCCCGCAGAGACGTGAACTTTCAGAATTAATTGGCGTAACGCGTAACTACGTTACG TGAAGTGTTACAGCCGTCTGGCACGATGGCCTGGTTGACCATTCAACATGGCAAGCCGACGAAGGTGAATAAT TTCTGGGATTTCCGGTTGTATCCTTGAAACATCCTTGACTACTATTTTATTCCACTATTTTATTCCGAAGGGTCGCCAGCTTA TTGATAATTTGCTGTCGGTGCGTACCACATATTTCCACTATTTTTATTCCGACCGCCGTTTCGTCGCCATCCCGA TAAAGCGCAGGAAGTGCTGGCTGGCCGTTTGCTTCCGCCGATCAGTGGCCAACCCGATTTACGCCGAGCTGGATAC AACATATTCCGCGGCCGTGCTGGCCGTTTGCTTCCGCCAATCCGAAGCGCCGAATCCGGAAGCGCGCAATCCTGGGCGTGCTGCTATGGGCATGAGAGT ACTGTCGCCGTTGTGCAGTGAAGGCGCGCACGATCAGTGTGACGAAACAGTGCGTCGCTATGGGCATGAGAGT GGCGAGATTTGGCCACCGGATGCAGAAAAATCTGCCGGGTGATTTAGCCATTCAGGGGCGATAA |
| | | MVIKAQSPAGFAEEYIIESIWNNRFPPGTILPAERELSELIGVTRTTLREVLQRLARDGWLTIQHGKPTKVNN FWETSGLNILETLARLDHESVPQLIDNLLSVRTNISTIFIRTAFRQHPDKAQEVLATANEVADHADAFAELDY NIFRGLAFASGNPIYGLIINGMKGLYTRIGRHYFANPEARSLALGFYHKLSALCSEGAHDQVYETVRIGHES |

Figure 3 (Cont.)

| SEQ ID NO: | DESCRIPTOR | SEQUENCE (5' - 3' - POLYNUCLEOTIDE) |
|---|---|---|
| 25 AND 26 | FABD | GEIWHRMQKNLPGDLAIQGR<br><br>ATGACGCAATTTGCATTTGTGTTCCCTGGACAGGGTTCTCAAACCGTTGGAATGCTGGCTGATATGGCGGCGA<br>GCTATCCAATTGTCGAAGAAACGTTTGCTGAAGCTTCTGCGGCGTCTGGGCTACGACCTGTGGGCGCTGACCCA<br>GCAGGGGCCAGCTGAAGACGTGAATTAAAACCTGGCAAACTCAGCCTGCGCTGTTGACTGCATCTGTTGCGCTG<br>TATCGGTATGGCAGCAGCGGGCGTGATTGAATTCGCTGAATGATGGCCGGTCACAGACCTGGTGGGGAATACTCCG<br>CGCTGGTTTGCGCTGGTGTGATTGCGCTGATGCGTCGGTCTGGTTGAGATGCGCGGCAAGTTCATGCA<br>AGAAGCCGTACCGGAAGGCACGGGCGTATGGCGGCAATCATCGGTTCGGATGATGCGTCTATTGCGAAAGCG<br>TGTGAAGAAGCTGCAGAAGGTCAGGTCGTTCTGCCTGTCTAACCGTTGTGAATAACCGTTGATGTGACAGCGAAGTAGATCATGGCAGCGCAAGG<br>GTCATAAAGAAGCGGTTGAGCGTTGAACGTGCCTGCCTGTAAAGCGGGCAGCCGACAAACTGGCAGTAGATGGCAGCGCAAGG<br>AGTGAGCGTACCGTCTCACTGTCGCGCTGATGAAACCAGCCAGCCGGCAAGCTGCGACAAGCCAATGGCAGCGCAAGG<br>ACCTTTAACGCACCAAACTCTCGTTGTATAACCCGTTCAGTGCTTAGATGGACAATGGCAGCGCAAGG<br>GTGACGCACTGGTACGTCAGTTGGAGTACGCGGCCGCAAAGGTGCTTACTGGCCTGACGAAACGCATTGTCGACACCCTG<br>CGTAGAACAATCTCTATGAGAACGAACCTTCAGCGATGGCAGCGGCGGCAGCGCTCGAGCTTTAA<br>ACCGCCTCGGCGCTGAACGAACCTTCAGCGATGGCAGCGGCGGCAGCGCTCGAGCTTTAA |
| 27 AND 28 | FABB | MTQFAFVFPGQGSQTVGMLADMAASYPTIVEETFAEASRALGYDIWALTQQGPAEELNKTWQTQPALLTASVAL<br>IRVWQQGQGKAPAMWAGHSLGEYSALVCAGVIDFADAVRLVEMRGKFMQEAVPEGTGAMAAIIGLDDASIAKA<br>CEEARAGQVVSPVNFNSPGQVVIAGHKEAVERAGAACKRAGAKRALPLPVSVPSHCALMKPAADKLAVELAKI<br>TFNAPTVPVVNNVDVKCETNGDAIRDALVRQLYNFVQWTKSVEYMAAQGVEHLYEVGPGKVLTGLTKRIVDTL<br>TASALNEPSAMRAALEL<br><br>ATGAAACGTGCAGTGATTACTGGCCCTGATTGATTCAGCATCCGGGTAATAACCAGCAGGAAGTCCTGGCAT<br>CTCTGCCGTGAAGGACGTTCAGGGATCACTTTCTCAGGAGCTCATGCTGAAGGATTCCGGCATGCGTAGCCACGTCTG<br>GGGCAACGTAAAACTGGATGATACCAGCAGGCAATCGCTGACCCGAAAGTTGTGCGCTTTATGAGCGACGCATCCATT<br>TATGCATTCCTTTCTGATTGCAGGTTCCGGCGACGGCAATCGCTGATGCGGCTCTCGCGGCGGATAACCGGC<br>GCGTTGGCCTGATTGCAGGTTCCGGCGGTTGGCCGATGCGCCCGTATGTGGTCACCAAAGCGATGCATCCGGCGTTCTGCCCTC<br>CCCGCGCGGCCGTTTAAATTCATGGCCGTTAAGTCATGGCCGATGCGCCCGTATGTGGTCACCAAAGCGATGCATCCGGCGTTCTGCCCTC<br>GCCACCCCGTTTAAATTCATGGCCGTTAAGTCATGGCCGTTTACTGCCGGCCTGGCGCCGTATGTAGTGGTTGGGTTCACCAAAGCGATGCATCCGGCGTTCTGCCCTC<br>GGAAAATGGCTTGCGAATTCGACGCAATTGGGTTCGTGCGCTGTTCTAACAACGACACCCCGGAAAAAGCCTCC<br>CGTACTTACGACGCTCACCGTCGACGGTGCTCACATCGCGGCGCTACGGCGCTACGGCAACCTCCGGAAAAGCCTCC<br>AACACGCGCTGGCGCCGTGGTGCTCACATCGCGAAATCGTGAAATCTATGCTGAAATCGTTTGGGCGCGGCAACCTCGTTGATGGTCAGA |

Figure 3 (Cont.)

| SEQ ID NO: | DESCRIPTOR | SEQUENCE (5' – 3' – POLYNUCLEOTIDE) |
|---|---|---|
|  |  | CATGGTTGCTCCGTCTGGCGAAGGCGAGTACGCTGCATGAAGATGGCGATGCATGGCGTTGATACCCCAATC<br>GATTACCTGAACTGCCACCGTACTTCGCACTCCGGTTGGCGACGTGAAAGAGCTGGCCAGCTATCCGTGAAGTGT<br>TCGGCGATAAAGAGCCCGGCGATTTCTGCAACCAAAGCCATGACCGGTCACTCTCTCGGGCGCTGCTGGCGTACA<br>GGAAGCTATCTACTCCTGCTGATGCTGGAACACGGCTTTATCGCCCCGAGCATCAACATTCAACATTGAAGAGCTGGAC<br>GAGCAGGCTGCGGGTCTGAACATCGTGACCGAAACGACCGATCGCGAACGATCGCGACCGATCGACCACCGTTATGTCTAACAGCT<br>TCGGCTTCGGCGGCCACCAACGCCACGCTGGTAATGCGCAAGCTGAAAGATTAA<br><br>MKRAVITGLGIVSSIGNNQQEVLASLREGRSGITFSQELKDSGMRSHVWGNVRLDTTGLIDRKVVREMSDASI<br>YAFLSMEQAIADAGLSPEAYQNNPRVGLIAGSGGGSPRFQVFGADAMRGPRGLKAVGPYVVTKAMASGVSACL<br>ATPFKIHGVNYSISSACATSAHCIGNAVEQIQLGKQDIVFAGGGEELCWEMACEFDAMGALSTKYNDTPEKAS<br>RTYDAHRDGFVIAGGGMVVEELEHALARGAHIYAEIVGYGATSDGADMVAPSGEGAVRCMKMAMHGVDTPI<br>DYLNSHGTSTPVGDVKELAAIREVFGDKSPAISATKAMTGHSLGAAGVQEAIYSLLMLEHGFIAPSINIEELD<br>EQAAGLNIVTETTDRELTTVMSNSFGFGGTNATLVMRKLKD |
| 29 AND 30 | FABF | GTGTCTAAGCGTCGTCGTAGTTGTGACCGGACTGGGCATGTTGTCTCCGTCGGCAATACCGTAGAGTCTACCT<br>GGAAAGCTCTGCTTGCCGGTCAGAGTGGCATCAGCCTAATGCGACCATTTCGACCTATGCGCCTATGCCTATGCAACGAA<br>ATTTGCTGGCTTAGTAAAGGATTTTAACTGTGAGGACATTACGCGCAGGACAGACAGCCAAGATGGCGCAAGATGGATGCC<br>TTCATTCAATATGGAATTGTCCCTGGCCGTTCAGGCCATGGCGGCCCTTGGCCTTGAAATAACGGAAGAGAACG<br>CAACCCGCATTGGTGCCGCAATTGGCCTCCGGGATTGGCGGCCTCGACCTGATCAACGATTGTGAACATAACCACATCTCT<br>GATGAACGGTGGCCTGCGGTAAGATCAGCCGTGGCCCCCGAGCATCTCTTCGTTCCATCGCGACTGCCTGTACTTCCGGCTGGCAGGTCAT<br>CTGACTATCATGTATGGCGCGTATTATCGCGTATTGGCGGTATGCCGATGCTGACCTGATGGTTGCAGGTGCAGGTTGCAGGATAACCGCAAGCCCAG<br>TTGGCCATGCTGGGCGTGGCCGTTGGTGGTTTTGGCGCGGTGCCGCAATGATAACCGCAAGCCCAG<br>TACGCCGCTGGGCCCCGTTGGGCCGTTGGTGGTTTTGGCGCGGTGCCGCAATGATAACCGCAAGCCCAG<br>AGCCGCTTAGCGGAGAGGCGAAAAAACGCGGTGCGAAAAATTGGCGCAGGCGCACCGTCGCCAAGCGCGATGCCGTGAACTCGTCGGCGATGGCAAATGCTCTGCCGTGATGGCAGGCAGGC<br>ACGAACACGCCGAAAAAACGCGGTGCGAAAAATTGGCGCAGGCGCACCGTCGTCGGCGATGGCAAATGCTCTGCCGTGATGGCAGGC<br>TCATATGACGTCACCCGCCAGATTGGCTACCGTTGAAGCTGCACGCCGTACTTCTGAAGCTGCACGCCGTACTTCGTGTTGGTAAGCTGCCACGAAAGCTGAAGCGC<br>ATTGAAGCGAGTCAGATTGGCTACCGTTGAAGCTGCACGCCGTACTTCTGTGTTGGTAAGCTGCCACGAAAATCTATGACCGGTCA<br>AGGCGGTGAAAACCATCTTCGGTGCAGTAGAATCTATCGCGATCTATCTGCGATCTGCGATCTGGATTTCGTACCGCGATCTGGATCAGCGATCTGGTCCGCCA<br>CCTGTTAGGTGCGGGGGTGCAGTAGAACCCGGATGAAGTTGCGATCGGATTTCGTACCGCGATCGAAGCGCGTCAGGTTAGCG<br>ACCATCAACCTGGATAACCCGGATGAAGTTGCGATCTGGATTTCGTACCGCGATCGAAGCGCGTCAGGTTAGCG<br>GAATGGAATACACTCTGTGTAACTCCTTCGGCTTCGGTGGCACTAATGGTTCTTTGATCTTTAAAAAGATCTA<br>A |

Figure 3 (Cont.)

| SEQ ID NO: | DESCRIPTOR | SEQUENCE (5' → 3' - POLYNUCLEOTIDE) |
|---|---|---|
| | | MSKRVVYTGLGKMLSPVGNTYESTWKALLAGQSGISLIDHFDTSAYATKFAGLVKDFNCEDIISRKEQRRMDA FIQIGIVAGVQAMQDSGLEITEENATRIGAAIGSIGIGLIEENHTSLMNGGPRKISPFFVPSTIVNMVAGH LTIMYGLRGPSISIATACTSGVHNIGHAARIIAYGDADVMVAGGAEKASTPLGVGGFGAARALSTRMDNFQAA SRPWDKERDGFVLGDGAGMLVLEEYEHAKKRGAKIYAELVGFGMSSDAYHMTSPPENGAGAALAMANALRDAG IEASQIGYVNAHGTSTPAGDKAEAQAVKTIFGEAASRVIVSSTKSMTGHLLGAAGAVESIYSILALRDQAVPP TINLDNPDEGCDLDFVPHEARQVSGMEYTLCNSFGFGGTNGSLIEKKI |
| 59 | PLS8379 | GGCATCCGCTTACAGACAAGCTGTGACCGTCTCCGGGAGCTGTCATGTGTCAGAGGTTTCACCGTCATCACCG AAACGCGAAGGCAGCAGATCAATTCGCGCGCAGCATGCGAAGCGCATGTTACGTTGACACCATCGAATG GTGCAAAACCTTTCCGGTATGCGCAGAGTATGCCGGTGTCTCTTATCAGACCGTTTCCCGTGGTGAACCAGGCCA GTAACGTTATACGATGTCGCAGAGTATGCCGGAAAACGGCGGAAAACGTCGTTGCTGAATTGCCCTCCAACCGCGT GCCACGTTCTCGCGCGGCCAAACAGTCGTTGCTGATTGGCCGTTGCCACCTCCAGTCTGGCCCTGCACGGCCG GGCCAACAACTCGGCGGCGATTAAATCTCGCGGCGGTGCCACTGGGGGCCAGCGTGGTGTCCAGTGGGCGATTCATTAA GAAGCGGCTCGAAGCCTGTAAGCGGATGCCATTGCTGTGGAAGCTGCCACTAAATGTTCCGGCGTTATTCTTGAT CTATCCGCTGGATGGACCACCCATCACAGTATTATTTTCTCCCATGAAGACGGTACGCGAGACTCCGCCGCGTCTCTGCGTCT TGGTCGCATTGGGGTCCACCGGCCAAATCCGGGCCACTTAGCCGGCCACTTAAATCAGCCTGCCATAAATCCGTGCATAAAT GGCTGGCTGGCCATAAATATCCACTCGCCAAATCAAATTCAGCCGATAGCCGAAATGAACCGCGACTGGGAGTGCC ATGTCCGGTTTTCAACAAACCATGCCAAATGCGCCATTACGGAATGCAAATGCGAGTCCGGAGTGTGCCAACG ATCAGATGCGCTGGCGCTGGCCGCAAATGCGCAAGCTCAATGTTATATCCGAGTCCGGTTGGTGCGGATAATCTCGGTAGT GGGATACCGACGATACCGAAGACAGCAGCTCAATGTTCTGCTGCAACTCTCTCAGGGCCGGTTAACCACCATCAAACAGGATTTCGCCTG CTGGGGCAAACCAGCCTGGCCAATCCGTGGCAATCCAGGGCCGGCACCACCATAAAGGCAATGCAGCTGTGC CCGTCTCACTGGTGAAAGAAAAAACCACCCCTGGCGCGACTGGAAGCGGCGAGTGCAGTGCACCGGTGCACCGGTGCAACTGCAAATCACTGCAATCGCAACTGCAATCACTGCCACCACTGAACGCAATTAATGTAAG TTCATTAAATGCAGCTGATGCTGGTTTGACAGCTTATCATCGACTGCACGGTGCACGGTGCATCACTGCATAATCACTGCAATAATCACTGTCCGAATCACTGCAATCCGGGCGACTCCC CCATCGGAAGCCTGTGGTATCGGCTCGTCTGTGCCGACATCATAACGGTTCTGGCATCATAACGGTTCTGGCAATCATAACGTTCAGGGCGACTGAAATGAGCCTGTTGACAATT GTTCTGGATATAATGGTTTTCGCGTATAATGTGTGAGGCGGAATGCGAATTGTGAGCGGATAACAATTTCACAGGAAACACAGCGCCGCGCTGAGA AAAAGCCAAGCGGCACTGCTCTTTAACAATTTATCAGACAATCTGTGTGGGCACTCGACCGGAATTATCGATT |

| SEQ ID NO: | DESCRIPTOR | SEQUENCE (5' – 3' – POLYNUCLEOTIDE) |
|---|---|---|
| | | CCCGCAAACGGGCTGTTCTGGTGTTGCTAGTTTGTTGTTATCAGAATCGCAGATCCGGCTTCAGCCGGTTTGCCGG<br>CTGAAAGCGCTATTCTCCAGAATGCCATGAGATTTTTCCCAGGGAGGCGTCACTGGCTCCCGTGTTGTC<br>GGCAGCTTTGATTCGATAAGCAGCATCGCCTGTTCAGGCTGTCTATGTGTGACTGTTGAGCTGTAACAAGTT<br>GTCTCAGGTGTTCAATTTCATGTTCGATCTGTTCTAGTTGCTTTCATGGTGAACAGCTTTGAATGCACCARAAACTCGTAAAGCTCT<br>CTGTTCATCTGTTACATTGTCGATCTGTTCTAGTTGCTTTCATGGTGAACAGCTTTGAATGCACCARAAACTCGTAAAGCTCT<br>GATGTATCTATCTTTTTACACCGTTTTGTTTGTTAGTCTTGAGCTTCATCTGTGCATATGGACAGTTTTCCCTTTGATGTTAACGGTGAA<br>CAGTTGTTCTACTTTTGTTTGTTAGTCTTGAGCTTCACTGATAGATACAAGAGCCATAAGAACCTCAGATCC<br>TTCCGTATTAGCCAGTATGTTCTCTAGTGTGGTTCGTTGTTTTTGCGTGAGCCATGAGAGAACGRACCATTGAG<br>ATCATACTTACTTGCATGTCATGTCCGTTATGTAGGTAGGAATCCTGATGTAATGGTGAGCTGAATTTTTGCAGTTTGTCACCAT<br>TCGTGTAGTGTTTTTCTGGTTGTTCTCAAGTTCGGTTACGAGATCCATTTGTCTATCTAGTTCAACTTGGAAAAATCAA<br>CGTATCAGTCGGGGGCGGCCCTCGCTTATCARCCACCAATTTCATATGCCTGTAAGTGTTAAATCTTTACTTATT<br>GGTTCAAAAACCCATTGGTTAAGCCTTATATTTGCCTTGTGAGTTTCTTTTGTTAGTTCTTTTCAAGCATTAACATGAACATTAAATT<br>CATCAAGGCTAATCTCTATATTTGTTTTTCAAARGACTTAACATGTTCCAGATTATATTTTATGAACTGGCATAGTTGTCCACT<br>CCTCATAGAGTATTTGTTTTCAAARGACTTAACATGTTCCAGATTATATTTTATGAACTGGCATAGTTGTCCACT<br>AGATAAGGCAATATCTCTCACTAAACCAARAAGGATTCCTGATTCTCCGTCATCAGCTCTCTGGTTGCTTT<br>GGAARAATCTCAAAAGCCTTTAACCAARAAGGATTCCTGATGTTCATCATCTGAGCGTATTGGTTATAAGTGAACGATACC<br>AGCTAATACACCATAAGCATTTTCCCTACTGATGTTCATCATCTGAGCGTATTGGTTATAAGTGAACGATACC<br>GTCCGTTCTTTCCTTGTAGGGTTTTCAATCGTGGGGTTGAGTAGTGCCACACAGCATAAAATTAGCTTGGTTT<br>CAATGCTCCGTTAAGTCATTAGCGACTAAGTCAATTGCTTTGAAACAACTAATTCAGACATACATCT<br>CTTTGAGTTGTGGGTATCTGTAAATTCTGCTGTAAATTCTGCGAARAACTTGTAAATTCTGCTAGAAATAAATTCAGAATTAAAGAAAGA<br>TAAATTCCGCTAAGACCTTTGTGTGTTTTTTGTTATATTCAAGTGGTTATAAATTTATAGAATAAAGAAAGA<br>ATAAAAAAGATAAAAAGAATAGATCCCAGCCCTGTATAACTCACTTAGTCAGTTCCGACAGTATTAC<br>AAAAGGATGCGAAACGCTGTTTGCCTCCCTCTACAAAACAGACCTTAAAACCCTAAAGGCTTAAG |
| 62 and 63 | TE | ATGACCTTAGAGTGGAAACCAAAACCGAAATTTACCCCTCAGCTTCTGACGACCACTTCGGCCTGCAGGTTTAAG<br>TATTCCGCAGAACGTTTGCCATAAGAAGCTACGAAGTAGGACCAGATCGTTCTACCTCTATACTTGCTGTGAT<br>GAATCATATGCAGGAAGCCACGTTAAATCACGCAAAGAGCGTCGGATCCTTGGGAGCAGGAATCGGCACCACA<br>TTGGAAATGAGTAAGCGGGACCTGATGTGGGTTGTTCGTCGTCGATGTGGGTCTGAAACGGTATCAACAT<br>GGGGCGATACTGTTGAAGTGGAGTGCTGGATTGGCGCGCTTCCGGAAACAACGGAATGCGCAGAGATTTCTGGT<br>GCGGGACTGTAAAACTGGGGAAACTTAACGCGCTGTACCTCCCTGCCGTTCTGATGAACACGCGTACCCGG |

Figure 3 (Cont.)

| SEQ ID NO: | DESCRIPTOR | SEQUENCE (5' – 3' – POLYNUCLEOTIDE) |
|---|---|---|
| | | AGATTAAGTACGATTCCGACGAAGTCCGTGGTGAAATCGGTCCCGCTTTTATTGACAACGTGGCGGGTAAAAG ACGACGAGATCAAAAAGTTGCAGAAATTGAACGATTCCACAGCAGATTACATACAGGGCGGTCTTACGCCCCG TTGGAACGACTTGGATGTGAATCAGCACGTAAATAACCTTAAATAATGTGGCGTGGGTGTTCGAGACCGTTCCC GACTCTATTTTTGAAAGTCACCACGGTGTCTGGCGGATCTTCCGAAGCTGGAGTACAGACGCGAGTGTACGCCGATTCCG TTTTACGTTCCCTCACCACGGTGTCTGGCGGATCTTCCGAAGCTGGGTTAGTGTGTGATCACTTGCTGCAACT TGAAGGCGAAGTGAAGTTCTTCGGCCCGCACGGAATGGCGTCCCAAACTGACCGATTCCTTCCGCGGAATA TCAGTAAATTCCGGCCGAGCCGCGGGTATAA |
| | | MTLEWKPKPKLPQLLDDHFGLHGLVFRRTFAIRSYEVGPDRSTSILAVMNHMQEATLNHAKSVGILGDGFGTT LEMSKRDLMWVVRRTHVAVERYPTWGDTVEVECWIGASGNNGMRRDFLVRDCKTGEILTRCTSLSVLMNTRTR RLSTIPDEVRGEIGPAFIDNVAVKDDEIKKLQKLNDSTADYIQGGLTPRWNDLDVNQHVNNLKYVAWVEETVP DSIFESHHISSFTLEVRRECTRDSVLRSLTTVSGGSSEAGLVCDHLLQLEGGSEVLRARTEWRPKLTDSFRGI SVIPPAEPRV |

```
                        SEQUENCE LISTING

<160> NUMBER OF SEQ ID NOS: 64

<210> SEQ ID NO 1
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 1
atggctactc aacaacaaca gaacggtgca tctgcatccg gcgtcttgga acaacttcgt      60
ggaaagcacg ttcttatcac aggtactacc ggattttttgg gcaaagtggt tctggaaaag     120
ttgattcgta ctgttccgga tattggaggt attcatctgc tgattcgtgg caataaacgt     180
catccagccg ctcgtgaacg tttcctgaac gaaattgcgt cctcctccgt cttcgaacgt     240
ttgcgtcacg atgataatga agccttcgag accttcttgg aagaacgtgt tcactgtatt     300
accggtgagg ttactgaatc ccgttttggt ttgacacctg aacgttttcg tgctttggcc     360
ggtcaggttt acgcttttat taacagcgct gcaagcgtga actttcgtga ggaattggat     420
aaagccctga aaatcaacac cttgtgtctt gaaaatgttg ctgctcttgc agaattgaac     480
tccgctatgg cggtcattca ggtttccact tgttacgtta acggtaaaaa ctccggtcaa     540
attaccgaat ccgtcattaa acctgctggc gaatccattc cccgttccac tgacggttac     600
tacgagatcg aagaattggt ccatctgttg caagacaaga tttccgatgt aaagctcgt      660 tactccggca aagttctgga gaaaaaattg gttgatttgg gtattcgtga ggccaataat     720
tacggatggt ccgacaccta cacattcacc aaatggttgg gtgaacaact gctgatgaag     780
gccttgtctg gtcgttcttt gactattgtg cgtccctcta ttattgagtc cgctttggaa     840
gaaccttccc ctggttggat cgaaggcgtt aaagttgccg atgccattat cttggcttat     900
gcccgtgaaa aagttagcct gttccctgga aaacgttccg cattattga tgttattcct      960 gtcgatttgg ttgcgaactc catcatcttg tctctggctg aggcgttgtc tggttctggt    1020
caacgtcgta tttatcaatg ttgcagcggt ggttctaatc caatctccct gggtaagttc    1080
attgattatt tgatggccga ggctaagacc aactatgctg cctacgatca actgtttat     1140 cgtcgtccta ctaaacttt cgtcgccgtg aaccgtaaat tgtttgacgt tgttgttggt    1200
ggtatgcgtg ttcctcttttc tattgccggt aaagctatgc gtttggctgg tcaaaatcgt    1260
gagttgaaag tgcttaagaa ccttgatacg acccgttccc ttgcaaccat ttttggcttc    1320
tatactgctc ccgactatat cttccgtaac gatagcttga tggccctggc ttctcgtatg    1380
```

```
ggtgaattgg atcgtgttct tttcccagtt gatgctcgtc aaattgattg gcagttgtac    1440
ttgtgtaaaa ttcatttggg tggtctgaac cgttacgctt tgaaggaacg taaactgtat    1500
tctttgcgtg ctgctgatac tcgtaaaaaa gctgcctaa                           1539
```

<210> SEQ ID NO 2
<211> LENGTH: 512
<212> TYPE: PRT
<213> ORGANISM: Marinobacter algicola

<400> SEQUENCE: 2

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
                35                  40                  45

Gly Gly Ile His Leu Leu Ile Arg Gly Asn Lys Arg His Pro Ala Ala
            50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
            115                 120                 125

Ser Ala Ala Ser Val Asn Phe Arg Glu Glu Leu Asp Lys Ala Leu Lys
        130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
                180                 185                 190

Ile Pro Arg Ser Thr Asp Gly Tyr Tyr Glu Ile Glu Glu Leu Val His
            195                 200                 205

Leu Leu Gln Asp Lys Ile Ser Asp Val Lys Ala Arg Tyr Ser Gly Lys
        210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
                260                 265                 270

Ser Ile Ile Glu Ser Ala Leu Glu Glu Pro Ser Pro Gly Trp Ile Glu
            275                 280                 285

Gly Val Lys Val Ala Asp Ala Ile Ile Leu Ala Tyr Ala Arg Glu Lys
        290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
                340                 345                 350
```

```
Asn Pro Ile Ser Leu Gly Lys Phe Ile Asp Tyr Leu Met Ala Glu Ala
            355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 3
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 3
atggcgactc aacaacagca gaacggtgca tctgcatccg gcgtcttgga caaacttcgt      60
ggaaagcacg ttcttatcac aggtactacc ggattttggg caaagtggt tctggaaaag     120 ttgattcgta ctgttccgga tattggaggt attcatctgc tgattcgtgg caataaacgt     180
catccagccg ctcgtgaacg tttcctgaac gaaattgcgt cctcctccgt cttcgaacgt     240
ttgcgtcacg atgataatga agccttcgag accttcttgg aagaacgtgt tcactgtatt     300
accggtgagg ttactgaatc ccgttttggt ttgacacctg agcgttttcg tgctttggcc     360
ggtcaggttg acgcttttat taacagcgct gcaagcgtga gttttcgtga gcaattggat     420
aaagccctga aaatcaacac cttgtgtctt gaaaatgttg ctgctcttgc agaattgaac     480
tccgctatgg cggtcattca ggtttccact tgttacgtta acggtaaaaa ctccggtcaa     540
attaccgaat ccgtcattaa atcggctggc gaatccattc cccgttccac tgacggttac     600
tacgagatca agaattggt ccatctgttg caagacaaga tttccgatgt aaagctcgt      660 tactccggca agttctgga gaaaaaattg gttgatttgg gtattcgtga ggccaataat     720
tacggatggt ccgacaccta cacattcacc aaatggttgg gtgaacaact gctgatgaag     780
gccttgtctg gtcgttcttt gactattgtg cgtccctcta ttattgagtc cgctttggaa     840
gaaccttccc ctggttggat cgaaggcgtt aaagttgccg atgccattat cttggcttat     900
gcccgtgaaa agttagcct gttccctgga aaacgttccg gcattattga tgttattcct     960
gtcgatttgg ttgcgaactc catcatcttg tctctggctg aggcgttgtc tggttctggt    1020
caacgtcgta tttatcaatg ttgcagcggt ggttctaatc caatctccct gggtaagttc    1080
attgattatt tgatggccga ggctaagacc aactatgctg cctacgatca actgttttat    1140
```

```
cgtcgtccta ctaaaccttt cgtcgccgtg aaccgtaaat tgtttgacgt tgttgttggt    1200
ggtatgcgtg ttgtcctttc tattgccggt aaagctatgc gtttggctgg tgtaaatcgt    1260
gagttgaaag tgcttaagaa ccttgatacg acccgtaaac ttgcaaccat ttttggcttc    1320
tatactgctc ccgactatat cttccgtaac gatagcttga tggccctggc tcagcgtatg    1380
ggtgaattgg atcgtgttct tttcccagtt gatgctcgtc aaattgattg gcagttgtac    1440
ttgtgtaaaa ttcatttggg tggtctgaac cgttacgctt tgaaggaacg taaactgtat    1500
tcttcgcgtg ctgctgatac tgacgataaa accgcctaa                          1539
```

<210> SEQ ID NO 4
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 4

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Ser Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
```

```
              290              295              300
Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Ser
            340                 345                 350

Asn Pro Ile Ser Leu Gly Lys Phe Ile Asp Tyr Leu Met Ala Glu Ala
            355                 360                 365

Lys Thr Asn Tyr Ala Ala Tyr Asp Gln Leu Phe Tyr Arg Arg Pro Thr
        370                 375                 380

Lys Pro Phe Val Ala Val Asn Arg Lys Leu Phe Asp Val Val Gly
385                 390                 395                 400

Gly Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510

<210> SEQ ID NO 5
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 5
atggcgactc aacaacagaa caacggtgca tctgcatccg gcgtcttgga aattcttcgt      60
ggaaagcacg ttcttatcac aggtactacc ggattttttgg gcaaagtggt tctggaaaag     120
ttgattcgta ctgttccgga tattggaggt attcatctgc tgattcgtgg caataaacgt     180
catccagccc tggcgaacg tttcctgaac gaaattgcgt cctcctccgt cttcgaacgt     240
ttgcgtcacg atgataatga agccttcgag accttcttgg aagaacgtgt tcactgtatt     300
accggtgagt tactgaatcc cgttttggt ttgacacctg agcgttttcg tgctttggcc      360
ggtcaggttg acgcttttat tcatagcgct gcaagcgtga actttcgtga gcaattggat     420
aaagccctga aaatcaacac cttgtgtctt gaaatgttg ctgctcttgc agaattgaac      480
tccgctatgg cggtcattca ggtttccact tgttacgtta acggtaaaac ctccggtcaa     540
attaccgaat ccgtcattaa atcggctggc gaatccattc cccgttccac tgacggttac     600
tacgagatcg aagaattggt ccatctgttg caagacaaga tttccgatgt aaagctcgt     660 tactccggcc gtgttatggg gaaaaaattg gttgatttgg gtattcgtga ggccaataat     720 tacgatggt ccgacaccta cacattcacc aaatggttgg gtgaacaact gctgatgaag     780
gccttgtctg gtcgttcttt gactattgtg cgtcccctcta ttattgagtc cgcttttggaa    840
```

```
gaaccttccc ctggttggat cgaaggcgtt aaagttgccg atgccattat cttggcttat    900
gcccgtgaaa aagttagcct gttccctgga aacgttccg gcattattga tgttattcct    960
gtcgatttgg ttgcgaactc catcatcttg tctctggctg aggcgttgtc tggttctggt   1020
caacgtcgta tttatcaatg ttgcagcggt ggttctaatc caatctccct gggtaagttc   1080
attgattatt tgaacgccga ggctaagacc aactatgctg cctacgatca actgttttat   1140
cgtcgtccta ctaaaccttt cgtcgccgtg aaccgtaaat gtttgacgt tgttgttggt    1200 gtcatgcgtg ttgtcctttc tattgccggt aaagctatgc gtttggctgg tgtaaatcgt   1260
gagttgaaag tgcttaagaa ccttgatacg acccgtaaac ttgcaaccat ttttggcttc   1320
tatactgctc ccgactatat cttccgtaac gatagcttga tggccctggc tcagcgtatg   1380
ggtgaattgg atcgtgttct tttcccagtt gatgctcgtc aaattgattg gcagttgtac   1440
ttgtgtaaaa ttcatttgcg tggtctgaac cgttacgctt tgaaggaacg taaactgtat   1500
tcttcgcgtg ctgctgatac tgacgataaa accgcctaa                          1539
```

<210> SEQ ID NO 6
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 6

```
Met Ala Thr Gln Gln Gln Asn Asn Gly Ala Ser Ala Ser Gly Val Leu
1               5                   10                  15

Glu Ile Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Gly Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile His
        115                 120                 125

Ser Ala Ala Ser Val Asn Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Thr Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Arg
    210                 215                 220

Val Met Gly Lys Lys Leu Val Asp Leu Gly Ile Arg Glu Ala Asn Asn
225                 230                 235                 240
```

```
Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Asn Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Gly
385                 390                 395                 400

Val Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Arg Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510

<210> SEQ ID NO 7
<211> LENGTH: 1539
<212> TYPE: DNA
<213> ORGANISM: Artificial Sequence
<220> FEATURE:
<223> OTHER INFORMATION: Synthetic polynucleotide

<400> SEQUENCE: 7
atggcgactc aacaacagaa caacggtgca tctgcatccg cgtcttgga aattcttcgt      60 ggaaagcacg ttcttatcac aggtactacc ggattttttgg gcaaagtggt tctggaaaag     120
ttgattcgta ctgttccgga tattggaggt attcatctgc tgattcgtgg caataaacgt     180
catccagccg ctcgcgaacg tttcctgaac gaaattgcgt cctcctccgt cttcgaacgt     240
ttgcgtcacg atgataatga agccttcgag accttcttgg aagaacgtgt tcactgtatt     300
accggtgaga ttactgaatc ccgttttggt ttgacacctg agcgttttcg tgctttggcc     360
ggtcaggttg acgcttttat tcatagcgct gcaagcgtga actttcgtga gcaattggat     420
aaagccctga aaatcaacac cttgtgtctt gaaaatgttg ctgctcttgc agaattgaac     480
tccgctatgg cggtcattca ggtttccact tgttacgtta acggtaaaac ctccggtcaa     540
```

```
attaccgaat ccgtcattaa atcggctggc gaatccattc cccgttccac tgacggttac    600
tacgagatcg aagaattggt ccatctgttg caagacaaga tttccgatgt aaagctcgt    660 tactccggcc gtgttatggg gaaaaaattg gttgatttgg gtattcgtga ggccaataat    720 tacgatggt  ccgacaccta cacattcacc aaatggttgg gtgaacaact gctgatgaag    780
gccttgtctg gtcgttcttt gactattgtg cgtccctcta ttattgagtc cgctttggaa    840
gaaccttccc ctggttggat cgaaggcgtt aaagttgccg atgccattat cttggcttat    900
gcccgtgaaa aagttagcct gttccctgga aaacgttccg gcattattga tgttattcct    960
gtcgatttgg ttgcgaactc catcatcttg tctctggctg aggcgttgtc tggttctggt   1020
caacgtcgta tttatcaatg ttgcagcggt ggttctaatc caatctccct gggtaagttc   1080
attgattatt tgaacgccga ggctaagacc aactatgctg cctacgatca actgttttat   1140
cgtcgtccta ctaaaccttt cgtcgccgtg aaccgtaaat tgtttgacgt tgttgttggt   1200
gtcatgcgtg ttgtcctttc tattgcccgc aaagctatgc gtttggctgg tgtaaatcgt   1260
gagttgaaag tgcttaagaa ccttgatacg acccgtaaac ttgcaaccat ttttggcttc   1320
tatactgctc ccgactatat cttccgtaac gatagcttga tggccctggc tcagcgtatg   1380
ggtgaattgg atcgtgttct tttcccagtt gatgctcgtc aaattgattg gcagttgtac   1440
ttgtgtaaaa ttcatttgcg tggtctgaac cgttacgctt tgaaggaacg taaactgtat   1500
tcttcgcgtg ctgctgatac tgacgataaa accgcctaa                           1539
```

<210> SEQ ID NO 8
<211> LENGTH: 512
<212> TYPE: PRT
<213> ORGANISM: Artificial Sequence
<220> FEATURE:
<223> OTHER INFORMATION: Synthetic polypeptide

<400> SEQUENCE: 8

```
Met Ala Thr Gln Gln Asn Asn Gly Ala Ser Ala Ser Gly Val Leu
1               5                   10                  15

Glu Ile Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
            35                  40                  45

Gly Gly Ile His Leu Leu Ile Arg Gly Asn Lys Arg His Pro Ala Ala
        50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Ile Thr Glu Ser Arg Phe Gly Leu Thr
            100                 105                 110

Pro Glu Arg Phe Arg Ala Leu Ala Gly Gln Val Asp Ala Phe Ile His
        115                 120                 125

Ser Ala Ala Ser Val Asn Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Thr Ser Gly Gln Ile Thr Glu Ser Val Ile Lys Ser Ala Gly Glu Ser
            180                 185                 190
```

-continued

```
Ile Pro Arg Ser Thr Asp Gly Tyr Tyr Glu Ile Glu Glu Leu Val His
            195                 200                 205
Leu Leu Gln Asp Lys Ile Ser Asp Val Lys Ala Arg Tyr Ser Gly Arg
        210                 215                 220
Val Met Gly Lys Lys Leu Val Asp Leu Gly Ile Arg Glu Ala Asn Asn
225                 230                 235                 240
Tyr Gly Trp Ser Asp Thr Tyr Thr Phe Thr Lys Trp Leu Gly Glu Gln
                245                 250                 255
Leu Leu Met Lys Ala Leu Ser Gly Arg Ser Leu Thr Ile Val Arg Pro
            260                 265                 270
Ser Ile Ile Glu Ser Ala Leu Glu Pro Ser Pro Gly Trp Ile Glu
        275                 280                 285
Gly Val Lys Val Ala Asp Ala Ile Ile Leu Ala Tyr Ala Arg Glu Lys
    290                 295                 300
Val Ser Leu Phe Pro Gly Lys Arg Ser Gly Ile Ile Asp Val Ile Pro
305                 310                 315                 320
Val Asp Leu Val Ala Asn Ser Ile Ile Leu Ser Leu Ala Glu Ala Leu
                325                 330                 335
Ser Gly Ser Gly Gln Arg Arg Ile Tyr Gln Cys Cys Ser Gly Gly Ser
            340                 345                 350
Asn Pro Ile Ser Leu Gly Lys Phe Ile Asp Tyr Leu Asn Ala Glu Ala
        355                 360                 365
Lys Thr Asn Tyr Ala Ala Tyr Asp Gln Leu Phe Tyr Arg Arg Pro Thr
    370                 375                 380
Lys Pro Phe Val Ala Val Asn Arg Lys Leu Phe Asp Val Val Gly
385                 390                 395                 400
Val Met Arg Val Val Leu Ser Ile Ala Arg Lys Ala Met Arg Leu Ala
                405                 410                 415
Gly Val Asn Arg Glu Leu Lys Val Leu Lys Asn Leu Asp Thr Thr Arg
            420                 425                 430
Lys Leu Ala Thr Ile Phe Gly Phe Tyr Thr Ala Pro Asp Tyr Ile Phe
        435                 440                 445
Arg Asn Asp Ser Leu Met Ala Leu Ala Gln Arg Met Gly Glu Leu Asp
    450                 455                 460
Arg Val Leu Phe Pro Val Asp Ala Arg Gln Ile Asp Trp Gln Leu Tyr
465                 470                 475                 480
Leu Cys Lys Ile His Leu Arg Gly Leu Asn Arg Tyr Ala Leu Lys Glu
                485                 490                 495
Arg Lys Leu Tyr Ser Ser Arg Ala Ala Asp Thr Asp Asp Lys Thr Ala
            500                 505                 510
```

<210> SEQ ID NO 9
<211> LENGTH: 954
<212> TYPE: DNA
<213> ORGANISM: Escherichia coli

<400> SEQUENCE: 9

| | |
|---|---:|
| atgtatacga agattattgg tactggcagc tatctgcccg aacaagtgcg gacaaacgcc | 60 |
| gatttggaaa aaatggtgga cacctctgac gagtggattg tcactcgtac cggtatccgc | 120 |
| gaacgccaca ttgccgcgcc aaacgaaacc gtttcaacca tgggctttga gcggcgaca | 180 |
| cgcgcaattg agatggcggg cattgagaaa gaccagattg gcctgatcgt tgtggcaacg | 240 |
| acttctgcta cgcacgcttt cccgagcgca gcttgtcaga ttcaaagcat gttgggcatt | 300 |

```
aaaggttgcc cggcatttga cgttgcagca gcctgcgcag gtttcaccta tgcattaagc    360
gtagccgatc aatacgtgaa atctggggcg gtgaagtatg ctctggtcgt cggttccgat    420
gtactggcgc gcacctgcga tccaaccgat cgtgggacta ttattatttt tggcgatggc    480
gcgggcgctg cggtgctggc tgcctctgaa gagccgggaa tcatttccac ccatctgcat    540
gccgacggta gttatggtga attgctgacg ctgccaaacg ccgaccgcgt gaatccagag    600
aattcaattc atctgacgat ggcgggcaac gaagtcttca aggttgcggt aacggaactg    660
gcgcacatcg ttgatgagac gctggcggcg aataatcttg accgttctca actggactgg    720
ctggttccgc atcaggctaa cctgcgtatt atcagtgcaa cggcgaaaaa actcggtatg    780
tctatggata atgtcgtggt gacgctggat cgccacggta atacctctgc ggcctctgtc    840
ccgtgcgcgc tggatgaagc tgtacgcgac gggcgcatta agccggggca gttggttctg    900
cttgaagcct ttggcggtgg attcacctgg ggctccgcgc tggttcgttt ctaa          954
```

<210> SEQ ID NO 10
<211> LENGTH: 317
<212> TYPE: PRT
<213> ORGANISM: Escherichia coli

<400> SEQUENCE: 10

```
Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg His Ile Ala Ala Pro Asn
        35                  40                  45

Glu Thr Val Ser Thr Met Gly Phe Glu Ala Ala Thr Arg Ala Ile Glu
    50                  55                  60

Met Ala Gly Ile Glu Lys Asp Gln Ile Gly Leu Ile Val Val Ala Thr
65                  70                  75                  80

Thr Ser Ala Thr His Ala Phe Pro Ser Ala Ala Cys Gln Ile Gln Ser
                85                  90                  95

Met Leu Gly Ile Lys Gly Cys Pro Ala Phe Asp Val Ala Ala Ala Cys
            100                 105                 110

Ala Gly Phe Thr Tyr Ala Leu Ser Val Ala Asp Gln Tyr Val Lys Ser
        115                 120                 125

Gly Ala Val Lys Tyr Ala Leu Val Val Gly Ser Asp Val Leu Ala Arg
    130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
            180                 185                 190

Asn Ala Asp Arg Val Asn Pro Glu Asn Ser Ile His Leu Thr Met Ala
        195                 200                 205

Gly Asn Glu Val Phe Lys Val Ala Val Thr Glu Leu Ala His Ile Val
    210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
```

```
                    260                 265                 270
Gly Asn Thr Ser Ala Ala Ser Val Pro Cys Ala Leu Asp Glu Ala Val
                275                 280                 285

Arg Asp Gly Arg Ile Lys Pro Gly Gln Leu Val Leu Leu Glu Ala Phe
            290                 295                 300

Gly Gly Gly Phe Thr Trp Gly Ser Ala Leu Val Arg Phe
305                 310                 315
```

<210> SEQ ID NO 11
<211> LENGTH: 981
<212> TYPE: DNA
<213> ORGANISM: Artificial Sequence
<220> FEATURE:
<223> OTHER INFORMATION: Synthetic polynucleotide

<400> SEQUENCE: 11

```
atgacaatga ttacgccgag ctctgaactc acccttacga aagggaataa aagctggtca      60
tcgacagctg tagctgccgc tttagagtgg aaaccaaaac cgaaattacc tcagcttctt     120
gacgaccact tcggcctgca tggtttagta ttccgcagaa cgtttgccat aagaagctac     180
gaagtaggac cagatcgttc tacctctata cttgctgtga tgaatcatat gcaggaagcc     240
acgttaaatc acgcaaagag cgtcgggatc cttggggacg gattcggcac cattggaa      300
atgagtaagc gggacctgat gtgggttgtt cgtcgtaccc acgtagcggt cgaacggtat     360
ccaacatggg gcgatactgt tgaagtggag tgctggattg gcgcttccgg aaacaacgga     420
atgcgcagag attttctggt gcgggactgt aaaactgggg aaatcttaac gcgctgtacc     480
tccctgtccg ttctgatgaa cacgcgtacc cggagattaa gtacgattcc ggacgaagtc     540
cgtggtgaaa tcggtcccgc ttttattgac aacgtggcgg taaaagacga cgagatcaaa     600
aagttgcaga aattgaacga ttccacagca gattacatac agggcggtct tacgccccgt     660
tggaacgact tggatgtgaa tcagcacgta aataacctta aatatgtggc gtgggtgttc     720
gagaccgttc ccgactctat tttgaaagt caccacattt ccagctttac gctggagtac     780
agacgcgagt gtacgcgcga ttccgttta cgttccctca ccacggtgtc tggcggatct     840
tccgaagctg ggttagtgtg tgatcacttg ctgcaacttg aaggcggaag tgaagttct     900
cgggcccgca cggaatggcg tcccaaactg accgattcct tccgcggaat atcagtaatt     960
ccggccgagc cgcgggtata a                                               981
```

<210> SEQ ID NO 12
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 12

```
Met Thr Met Ile Thr Pro Ser Ser Glu Leu Thr Leu Thr Lys Gly Asn
1               5                   10                  15

Lys Ser Trp Ser Ser Thr Ala Val Ala Ala Ala Leu Glu Trp Lys Pro
            20                  25                  30

Lys Pro Lys Leu Pro Gln Leu Leu Asp Asp His Phe Gly Leu His Gly
        35                  40                  45

Leu Val Phe Arg Arg Thr Phe Ala Ile Arg Ser Tyr Glu Val Gly Pro
    50                  55                  60

Asp Arg Ser Thr Ser Ile Leu Ala Val Met Asn His Met Gln Glu Ala
65                  70                  75                  80
```

```
Thr Leu Asn His Ala Lys Ser Val Gly Ile Leu Gly Asp Gly Phe Gly
                 85                  90                  95

Thr Thr Leu Glu Met Ser Lys Arg Asp Leu Met Trp Val Val Arg Arg
            100                 105                 110

Thr His Val Ala Val Glu Arg Tyr Pro Thr Trp Gly Asp Thr Val Glu
        115                 120                 125

Val Glu Cys Trp Ile Gly Ala Ser Gly Asn Asn Gly Met Arg Arg Asp
130                 135                 140

Phe Leu Val Arg Asp Cys Lys Thr Gly Glu Ile Leu Thr Arg Cys Thr
145                 150                 155                 160

Ser Leu Ser Val Leu Met Asn Thr Arg Thr Arg Leu Ser Thr Ile
                165                 170                 175

Pro Asp Glu Val Arg Gly Glu Ile Gly Pro Ala Phe Ile Asp Asn Val
            180                 185                 190

Ala Val Lys Asp Asp Glu Ile Lys Lys Leu Gln Lys Leu Asn Asp Ser
        195                 200                 205

Thr Ala Asp Tyr Ile Gln Gly Gly Leu Thr Pro Arg Trp Asn Asp Leu
    210                 215                 220

Asp Val Asn Gln His Val Asn Asn Leu Lys Tyr Val Ala Trp Val Phe
225                 230                 235                 240

Glu Thr Val Pro Asp Ser Ile Phe Glu Ser His His Ile Ser Ser Phe
                245                 250                 255

Thr Leu Glu Tyr Arg Arg Glu Cys Thr Arg Asp Ser Val Leu Arg Ser
            260                 265                 270

Leu Thr Val Ser Gly Gly Ser Glu Ala Gly Leu Val Cys Asp
        275                 280                 285

His Leu Leu Gln Leu Glu Gly Gly Ser Glu Val Leu Arg Ala Arg Thr
    290                 295                 300

Glu Trp Arg Pro Lys Leu Thr Asp Ser Phe Arg Gly Ile Ser Val Ile
305                 310                 315                 320

Pro Ala Glu Pro Arg Val
                325

<210> SEQ ID NO 13
<211> LENGTH: 2445
<212> TYPE: DNA
<213> ORGANISM: Escherichia coli

<400> SEQUENCE: 13
atgatgattt tgagtattct cgctacggtt gtcctgctcg gcgcgttgtt ctatcaccgc    60
gtgagcttat ttatcagcag tctgattttg ctcgcctgga cagccgcccct cggcgttgct   120 ggtctgtggt cggcgtgggt actggtgcct ctggccatta tcctcgtgcc atttaacttt   180
gcgcctatgc gtaagtcgat gatttccgcg ccggtatttc gcggtttccg taaggtgatg   240
ccgccgatgt cgcgcactga aaagaagcg attgatgcgg caccacctg gtgggagggc     300 gacttgttcc agggcaagcc ggactggaaa aagctgcata actatccgca gccgcgcctg   360
accgccgaag agcaagcgtt tctcgacggc ccggtagaag aagcctgccg gatggcgaat   420
gatttccaga tcacccatga gctggcgat ctgccgccgg agttgtgggc gtaccttaaa    480
gagcatcgtt tcttcgcgat gatcatcaaa aagagtacg gcgggctgga gttctcggct   540
tatgcccagt ctcgcgtgct gcaaaaactc tccggcgtga gcgggatcct ggcgattacc   600
gtcggcgtgc caaactcatt aggcccgggc gaactgttgc aacattacgg cactgacgag   660
```

```
cagaaagatc actatctgcc gcgtctggcg cgtggtcagg agatcccctg ctttgcactg    720
accagcccgg aagcgggttc cgatgcgggc gcgattccgg acaccgggat tgtctgcatg    780
ggcgaatggc agggccagca ggtgctgggg atgcgtctga cctggaacaa acgctacatt    840
acgctggcac cgattgcgac cgtgcttggg ctggcgttta aactctccga cccggaaaaa    900
ttactcggcg gtgcagaaga tttaggcatt acctgtgcgc tgatcccaac caccacgccg    960
ggcgtggaaa ttggtcgtcg ccacttcccg ctgaacgtac cgttccagaa cggaccgacg   1020
cgcggtaaag atgtcttcgt gccgatcgat tacatcatcg cgggccgaa aatggccggg    1080 caaggctggc ggatgctggt ggagtgcctc tcggtaggcc gcggcatcac cctgccttcc   1140
aactcaaccg gcggcgtgaa atcggtagcg ctggcaaccg gcgcgtatgc tcacattcgc   1200
cgtcagttca aaatctctat tggtaagatg aagggattg aagagccgct ggcgcgtatt    1260
gccggtaatg cctacgtgat ggatgctgcg gcatcgctga ttacctacgg cattatgctc   1320
ggcgaaaaac ctgccgtgct gtcggctatc gttaagtatc actgtaccca ccgcgggcag   1380
cagtcgatta ttgatgcgat ggatattacc ggcggtaaag gcattatgct cgggcaaagc   1440
aacttcctgg cgcgtgctta ccagggcgca ccgattgcca tcaccgttga aggggctaac   1500
attctgaccc gcagcatgat gatcttcgga caaggagcga ttcgttgcca tccgtacgtg   1560
ctggaagaga tggaagcggc gaagaacaat gacgtcaacg cgttcgataa actgttgttc   1620
aaacatatcg gtcacgtcgg tagcaacaaa gttcgcagct tctggctggg cctgacgcgc   1680
ggtttaacca gcagcacgcc aaccggcgat gccactaaac gctactatca gcacctgaac   1740
cgcctgagcg ccaacctcgc cctgctttct gatgtctcga tggcagtgct gggcggcagc   1800
ctgaaacgtc gcgagcgcat ctcggcccgt ctggggata ttttaagcca gctctacctc    1860
gcctctgccg tgctgaagcg ttatgacgac gaaggccgta atgaagccga cctgccgctg   1920
gtgcactggg gcgtacaaga tgcgctgtat caggctgaac aggcgatgga tgatttactg   1980
caaaacttcc gaaccgcgt ggttgccggg ctgctgaatg tggtgatctt cccgaccgga    2040
cgtcattatc tggcaccttc tgacaagctg gatcataaag tggcgaagat tttacaagtg   2100
ccgaacgcca cccgttcccg cattggtcgc ggtcagtacc tgacgccgag cgagcataat   2160
ccggttggct tgctggaaga ggcgctggtg atgtgattg ccgccgaccc aattcatcag    2220
cggatctgta aagagctggg taaaaacctg ccgtttaccc gtctggatga actgcgcac    2280 aacgcgctgg tgaagggct gattgataaa gatgaagccg ctattctggt gaaagctgaa    2340
gaaagccgtc tgcgcagtat taacgttgat gactttgatc cggaagagct ggcgacgaag   2400
ccggtaaagt tgccggagaa agtgcggaaa gttgaagccg cgtaa                   2445
```

<210> SEQ ID NO 14
<211> LENGTH: 814
<212> TYPE: PRT
<213> ORGANISM: Escherichia coli

<400> SEQUENCE: 14

```
Met Met Ile Leu Ser Ile Leu Ala Thr Val Val Leu Leu Gly Ala Leu
1               5                  10                  15

Phe Tyr His Arg Val Ser Leu Phe Ile Ser Ser Leu Ile Leu Leu Ala
            20                  25                  30

Trp Thr Ala Ala Leu Gly Val Ala Gly Leu Trp Ser Ala Trp Val Leu
        35                  40                  45

Val Pro Leu Ala Ile Ile Leu Val Pro Phe Asn Phe Ala Pro Met Arg
    50                  55                  60
```

-continued

```
Lys Ser Met Ile Ser Ala Pro Val Phe Arg Gly Phe Arg Lys Val Met
 65                  70                  75                  80

Pro Pro Met Ser Arg Thr Glu Lys Glu Ala Ile Asp Ala Gly Thr Thr
                 85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Ala Phe Leu
        115                 120                 125

Asp Gly Pro Val Glu Glu Ala Cys Arg Met Ala Asn Asp Phe Gln Ile
130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Gln Val Leu Gly Met Arg
            260                 265                 270

Leu Thr Trp Asn Lys Arg Tyr Ile Thr Leu Ala Pro Ile Ala Thr Val
        275                 280                 285

Leu Gly Leu Ala Phe Lys Leu Ser Asp Pro Glu Lys Leu Leu Gly Gly
        290                 295                 300

Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
            340                 345                 350

Ile Gly Gly Pro Lys Met Ala Gly Gln Gly Trp Arg Met Leu Val Glu
        355                 360                 365

Cys Leu Ser Val Gly Arg Gly Ile Thr Leu Pro Ser Asn Ser Thr Gly
        370                 375                 380

Gly Val Lys Ser Val Ala Leu Ala Thr Gly Ala Tyr Ala His Ile Arg
385                 390                 395                 400

Arg Gln Phe Lys Ile Ser Ile Gly Lys Met Glu Gly Ile Glu Glu Pro
                405                 410                 415

Leu Ala Arg Ile Ala Gly Asn Ala Tyr Val Met Asp Ala Ala Ala Ser
            420                 425                 430

Leu Ile Thr Tyr Gly Ile Met Leu Gly Glu Lys Pro Ala Val Leu Ser
        435                 440                 445

Ala Ile Val Lys Tyr His Cys Thr His Arg Gly Gln Gln Ser Ile Ile
        450                 455                 460

Asp Ala Met Asp Ile Thr Gly Gly Lys Gly Ile Met Leu Gly Gln Ser
465                 470                 475                 480
```

| | | | | | | | | | | | |
|---|---|---|---|---|---|---|---|---|---|---|---|
|Asn|Phe|Leu|Ala|Arg|Ala|Tyr|Gln|Gly|Ala|Pro|Ile|Ala|Ile|Thr|Val|
| | | | |485| | | |490| | | |495| | | |

Glu Gly Ala Asn Ile Leu Thr Arg Ser Met Met Ile Phe Gly Gln Gly
              500                 505                 510

Ala Ile Arg Cys His Pro Tyr Val Leu Glu Glu Met Glu Ala Ala Lys
              515                 520                 525

Asn Asn Asp Val Asn Ala Phe Asp Lys Leu Leu Phe Lys His Ile Gly
              530                 535                 540

His Val Gly Ser Asn Lys Val Arg Ser Phe Trp Leu Gly Leu Thr Arg
545                 550                 555                 560

Gly Leu Thr Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
              580                 585                 590

Ser Met Ala Val Leu Gly Gly Ser Leu Lys Arg Arg Glu Arg Ile Ser
              595                 600                 605

Ala Arg Leu Gly Asp Ile Leu Ser Gln Leu Tyr Leu Ala Ser Ala Val
              610                 615                 620

Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
              645                 650                 655

Asp Asp Leu Leu Gln Asn Phe Pro Asn Arg Val Val Ala Gly Leu Leu
              660                 665                 670

Asn Val Val Ile Phe Pro Thr Gly Arg His Tyr Leu Ala Pro Ser Asp
              675                 680                 685

Lys Leu Asp His Lys Val Ala Lys Ile Leu Gln Val Pro Asn Ala Thr
              690                 695                 700

Arg Ser Arg Ile Gly Arg Gly Gln Tyr Leu Thr Pro Ser Glu His Asn
705                 710                 715                 720

Pro Val Gly Leu Leu Glu Glu Ala Leu Val Asp Val Ile Ala Ala Asp
              725                 730                 735

Pro Ile His Gln Arg Ile Cys Lys Glu Leu Gly Lys Asn Leu Pro Phe
              740                 745                 750

Thr Arg Leu Asp Glu Leu Ala His Asn Ala Leu Val Lys Gly Leu Ile
              755                 760                 765

Asp Lys Asp Glu Ala Ala Ile Leu Val Lys Ala Glu Glu Ser Arg Leu
              770                 775                 780

Arg Ser Ile Asn Val Asp Asp Phe Asp Pro Glu Glu Leu Ala Thr Lys
785                 790                 795                 800

Pro Val Lys Leu Pro Glu Lys Val Arg Lys Val Glu Ala Ala
                805                 810

<210> SEQ ID NO 15
<211> LENGTH: 1686
<212> TYPE: DNA
<213> ORGANISM: Escherichia coli

<400> SEQUENCE: 15
atgaagaagg tttggcttaa ccgttatccc gcggacgttc cgacggagat caaccctgac    60
cgttatcaat ctctggtaga tatgtttgag cagtcggtcg cgcgctacgc cgatcaacct   120
gcgtttgtga atatggggga ggtaatgacc ttccgcaagc tggaagaacg cagtcgcgcg   180
tttgccgctt atttgcaaca agggttgggg ctgaagaaag gcgatcgcgt tgcgttgatg   240

```
atgcctaatt tattgcaata tccggtggcg ctgtttggca ttttgcgtgc cgggatgatc      300
gtcgtaaacg ttaacccgtt gtataccccg cgtgagcttg agcatcagct taacgatagc      360
ggcgcatcgg cgattgttat cgtgtctaac tttgctcaca cactggaaaa agtggttgat      420
aaaaccgccg ttcagcacgt aattctgacc cgtatgggcg atcagctatc tacggcaaaa      480
ggcacggtag tcaatttcgt tgttaaatac atcaagcgtt tggtgccgaa ataccatctg      540
ccagatgcca tttcatttcg tagcgcactg cataacggct accggatgca gtacgtcaaa      600
cccgaactgg tgccggaaga tttagctttt ctgcaataca ccggcggcac cactggtgtg      660
gcgaaaggcg cgatgctgac tcaccgcaat atgctggcga acctggaaca ggttaacgcg      720
acctatggtc cgctgttgca tccgggcaaa gagctggtgg tgacggcgct gccgctgtat      780
cacatttttg ccctgaccat taactgcctg ctgtttatcg aactgggtgg cagaacctg       840 cttatcacta acccgcgcga tattccaggg ttggtaaaag agttagcgaa atatccgttt      900
accgctatca cgggcgttaa caccttgttc aatgcgttgc tgaacaataa agagttccag      960
cagctggatt tctccagtct gcatctttcc gcaggcggtg ggatgccagt gcagcaagtg     1020
gtggcagagc gttgggtgaa actgaccgga cagtatctgc tggaaggcta tggccttacc     1080
gagtgtgcgc cgctggtcag cgttaaccca tatgatattg attatcatag tggtagcatc     1140
ggtttgccgg tgccgtcgac ggaagccaaa ctggtggatg atgatgataa tgaagtacca     1200
ccaggtcaac cgggtgagct ttgtgtcaaa ggaccgcagg tgatgctggg ttactggcag     1260
cgtcccgatg ctaccgatga aatcatcaaa atggctggt tacacaccgg cgacatcgcg      1320
gtaatggatg aagaaggatt cctgcgcatt gtcgatcgta aaaagacat gattctggtt       1380 tccggtttta acgtctatcc caacgagatt gaagatgtcg tcatgcagca tcctggcgta     1440
caggaagtcg cggctgttgg cgtaccttcc ggctccagtg gtgaagcggt gaaaatcttc     1500
gtagtgaaaa aagatccatc gcttaccgaa gagtcactgg tgactttttg ccgccgtcag     1560
ctcacgggat acaaagtacc gaagctggtg gagtttcgtg atgagttacc gaaatctaac     1620
gtcggaaaaa ttttgcgacg agaattacgt gacgaagcgc gcggcaaagt ggacaataaa     1680
gcctaa                                                                 1686
```

<210> SEQ ID NO 16
<211> LENGTH: 561
<212> TYPE: PRT
<213> ORGANISM: Escherichia coli

<400> SEQUENCE: 16

```
Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110
```

```
Leu Glu His Gln Leu Asn Asp Ser Gly Ala Ser Ala Ile Val Ile Val
            115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
            195                 200                 205

Ala Phe Leu Gln Tyr Thr Gly Gly Thr Thr Gly Val Ala Lys Gly Ala
            210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
            275                 280                 285

Pro Gly Leu Val Lys Glu Leu Ala Lys Tyr Pro Phe Thr Ala Ile Thr
            290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Met Pro
            325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
            355                 360                 365

Asn Pro Tyr Asp Ile Asp Tyr His Ser Gly Ser Ile Gly Leu Pro Val
370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
            420                 425                 430

Trp Leu His Thr Gly Asp Ile Ala Val Met Asp Glu Glu Gly Phe Leu
            435                 440                 445

Arg Ile Val Asp Arg Lys Lys Asp Met Ile Leu Val Ser Gly Phe Asn
450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Gly Glu Ala
            485                 490                 495

Val Lys Ile Phe Val Val Lys Lys Asp Pro Ser Leu Thr Glu Glu Ser
                500                 505                 510

Leu Val Thr Phe Cys Arg Arg Gln Leu Thr Gly Tyr Lys Val Pro Lys
            515                 520                 525

Leu Val Glu Phe Arg Asp Glu Leu Pro Lys Ser Asn Val Gly Lys Ile
```

Leu Arg Arg Glu Leu Arg Asp Glu Ala Arg Gly Lys Val Asp Asn Lys
545                 550                 555                 560

Ala

<210> SEQ ID NO 17
<211> LENGTH: 735
<212> TYPE: DNA
<213> ORGANISM: Escherichia coli

<400> SEQUENCE: 17

```
atgaattttg aaggaaaaat cgcactggta accggtgcaa gccgcggaat tggccgcgca    60
attgctgaaa cgctcgcagc ccgtggcgcg aaagttattg gcactgcgac cagtgaaaat   120
ggcgctcagg cgatcagtga ttatttaggt gccaacggca aaggtctgat gttgaatgtg   180
accgacccgg catctatcga atctgttctg aaaaaattc gcgcagaatt tggtgaagtg   240
gatatcctgg tcaataatgc cggtatcact cgtgataacc tgttaatgcg aatgaaagat   300
gaagagtgga acgatattat cgaaaccaac ctttcatctg ttttccgtct gtcaaaagcg   360
gtaatgcgcg ctatgatgaa aaagcgtcat ggtcgtatta tcactatcgg ttctgtggtt   420
ggtaccatgg gaaatggcgg tcaggccaac tacgctgcgg cgaaagcggg cttgatcggc   480
ttcagtaaat cactggcgcg cgaagttgcg tcacgcggta ttactgtaaa cgttgttgct   540
ccgggcttta ttgaaacgga catgacacgt gcgctgagcg atgaccagcg tgcgggtatc   600
ctggcgcagg ttcctgcggg tcgcctcggc ggcgcacagg aaatcgccaa cgcggttgca   660
ttcctggcat ccgacgaagc agcttacatc acgggtgaaa ctttgcatgt gaacggcggg   720
atgtacatgg tctaa                                                   735
```

<210> SEQ ID NO 18
<211> LENGTH: 244
<212> TYPE: PRT
<213> ORGANISM: Escherichia coli

<400> SEQUENCE: 18

Met Asn Phe Glu Gly Lys Ile Ala Leu Val Thr Gly Ala Ser Arg Gly
1               5                   10                  15

Ile Gly Arg Ala Ile Ala Glu Thr Leu Ala Ala Arg Gly Ala Lys Val
            20                  25                  30

Ile Gly Thr Ala Thr Ser Glu Asn Gly Ala Gln Ala Ile Ser Asp Tyr
        35                  40                  45

Leu Gly Ala Asn Gly Lys Gly Leu Met Leu Asn Val Thr Asp Pro Ala
    50                  55                  60

Ser Ile Glu Ser Val Leu Glu Lys Ile Arg Ala Glu Phe Gly Glu Val
65                  70                  75                  80

Asp Ile Leu Val Asn Asn Ala Gly Ile Thr Arg Asp Asn Leu Leu Met
                85                  90                  95

Arg Met Lys Asp Glu Glu Trp Asn Asp Ile Ile Glu Thr Asn Leu Ser
            100                 105                 110

Ser Val Phe Arg Leu Ser Lys Ala Val Met Arg Ala Met Met Lys Lys
        115                 120                 125

Arg His Gly Arg Ile Ile Thr Ile Gly Ser Val Val Gly Thr Met Gly
    130                 135                 140

Asn Gly Gly Gln Ala Asn Tyr Ala Ala Ala Lys Ala Gly Leu Ile Gly
145                 150                 155                 160

```
Phe Ser Lys Ser Leu Ala Arg Glu Val Ala Ser Arg Gly Ile Thr Val
                165                 170                 175
Asn Val Val Ala Pro Gly Phe Ile Glu Thr Asp Met Thr Arg Ala Leu
            180                 185                 190
Ser Asp Asp Gln Arg Ala Gly Ile Leu Ala Gln Val Pro Ala Gly Arg
        195                 200                 205
Leu Gly Gly Ala Gln Glu Ile Ala Asn Ala Val Ala Phe Leu Ala Ser
    210                 215                 220
Asp Glu Ala Ala Tyr Ile Thr Gly Glu Thr Leu His Val Asn Gly Gly
225                 230                 235                 240
Met Tyr Met Val

<210> SEQ ID NO 19
<211> LENGTH: 822
<212> TYPE: DNA
<213> ORGANISM: Artificial Sequence
<220> FEATURE:
<223> OTHER INFORMATION: Synthetic polynucleotide

<400> SEQUENCE: 19
atgaccgcag gactgatggc tgcaaacgt ggactgatta tgggcctggc caatgataaa      60
tcaatcgcgt ggggcattgc taaagcactg gtgatgcag gtgcggaact ggcgttttct     120
taccagggtg aagcactgaa gaagcgtgtt gaaccactgg ctgcaagcct gggcaccccg    180
ctgttattcg aatgtgatgt ggcaaacgaa gactcaatgg acgccctgtt tgcgggactg    240
aaagacgcat gggcacccct ggattttgtt gtgcatgcaa ttggctttag cgataaaaac    300
gaactgcgcg tcgttacgt ggatacgagc cgcggtaatt tcacgatgac gatggacatt    360
tcagtgtata gctttactgc tgtttgcgca cgcgctgctg ccatgatgcc gaacggtggt    420
agcctgctga ccctgaccta ctatggagcc gaacaggtaa tgccgcatta taacgttatg    480
ggtgtggcga agctgcgct tgaagcaagc gtgaaataca tcgcggaaga tctgggcaaa    540
ctgggcattc gttgtaatgc tatctcggct ggcccgatta aaaccctggc tgcaagcggc    600
attggcgact ttcgctatat catgaagtgg aacgagctga acagcccgct gcgccgcaac    660
gttacccagg aagaagttgg caaagccgcg ttatatctgt tgagcgatct gggcagcggc    720
accaccggtg aaaacctgca tgtggatgcc ggttaccacg tcgtcggcat gaaagcggtt    780
gatgcgccgg atattgacgt agtcacgggt cgtaaagact aa                      822

<210> SEQ ID NO 20
<211> LENGTH: 273
<212> TYPE: PRT
<213> ORGANISM: Rhodobacter capsulatus

<400> SEQUENCE: 20

Met Thr Ala Gly Leu Met Ala Gly Lys Arg Gly Leu Ile Met Gly Leu
1               5                   10                  15
Ala Asn Asp Lys Ser Ile Ala Trp Gly Ile Ala Lys Ala Leu Gly Asp
            20                  25                  30
Ala Gly Ala Glu Leu Ala Phe Ser Tyr Gln Gly Glu Ala Leu Lys Lys
        35                  40                  45
Arg Val Glu Pro Leu Ala Ala Ser Leu Gly Thr Pro Leu Leu Phe Glu
    50                  55                  60
Cys Asp Val Ala Asn Glu Asp Ser Met Asp Ala Leu Phe Ala Gly Leu
65                  70                  75                  80
Lys Asp Ala Trp Gly Thr Leu Asp Phe Val Val His Ala Ile Gly Phe
```

```
                        85                  90                  95
Ser Asp Lys Asn Glu Leu Arg Gly Arg Tyr Val Asp Thr Ser Arg Gly
            100                 105                 110

Asn Phe Thr Met Thr Met Asp Ile Ser Val Tyr Ser Phe Thr Ala Val
            115                 120                 125

Cys Ala Arg Ala Ala Met Met Pro Asn Gly Gly Ser Leu Leu Thr
            130                 135                 140

Leu Thr Tyr Tyr Gly Ala Glu Gln Val Met Pro His Tyr Asn Val Met
145                 150                 155                 160

Gly Val Ala Lys Ala Ala Leu Glu Ala Ser Val Lys Tyr Ile Ala Glu
                165                 170                 175

Asp Leu Gly Lys Leu Gly Ile Arg Cys Asn Ala Ile Ser Ala Gly Pro
            180                 185                 190

Ile Lys Thr Leu Ala Ala Ser Gly Ile Gly Asp Phe Arg Tyr Ile Met
            195                 200                 205

Lys Trp Asn Glu Leu Asn Ser Pro Leu Arg Arg Asn Val Thr Gln Glu
            210                 215                 220

Glu Val Gly Lys Ala Ala Leu Tyr Leu Leu Ser Asp Leu Gly Ser Gly
225                 230                 235                 240

Thr Thr Gly Glu Asn Leu His Val Asp Ala Gly Tyr His Val Val Gly
                245                 250                 255

Met Lys Ala Val Asp Ala Pro Asp Ile Asp Val Val Thr Gly Arg Lys
            260                 265                 270

Asp

<210> SEQ ID NO 21
<211> LENGTH: 456
<212> TYPE: DNA
<213> ORGANISM: Shigella flexneri

<400> SEQUENCE: 21
atgactacta acactcatac tctgcagatt gaagagattt tagaacttct gccgcaccgt      60
ttcccgttct tactggtgga tcgcgtgctg gattttgaag aaggtcgttt tctgcgcgca     120
gtaaaaaatg tctctgtcaa tgagccattc ttccagggcc atttccctgg aaaaccgatt     180
ttcccgggtg tgctgattct ggaagcaatg gcacaggcaa caggtattct ggcgtttaaa     240
agcgtaggaa aactggaacc gggtgagctg tactacttcg ctggtattga cgaagcgcgc     300
ttcaagcgcc cggtcgtgcc tggcgatcaa atgatcatgg aagtcacttt cgaaaaaacg     360
cgccgcggcc tgacccgttt taaggggtt gctctggtcg atggtaaagt agtttgcgaa     420
gcaacgatga tgtgtgctcg tagccggag gcctaa                                456

<210> SEQ ID NO 22
<211> LENGTH: 151
<212> TYPE: PRT
<213> ORGANISM: Shigella flexneri

<400> SEQUENCE: 22

Met Thr Thr Asn Thr His Thr Leu Gln Ile Glu Glu Ile Leu Glu Leu
1               5                   10                  15

Leu Pro His Arg Phe Pro Phe Leu Leu Val Asp Arg Val Leu Asp Phe
                20                  25                  30

Glu Glu Gly Arg Phe Leu Arg Ala Val Lys Asn Val Ser Val Asn Glu
            35                  40                  45

Pro Phe Phe Gln Gly His Phe Pro Gly Lys Pro Ile Phe Pro Gly Val
```

```
           50                  55                  60
Leu Ile Leu Glu Ala Met Ala Gln Ala Thr Gly Ile Leu Ala Phe Lys
 65                  70                  75                  80

Ser Val Gly Lys Leu Glu Pro Gly Leu Tyr Tyr Phe Ala Gly Ile
                 85                  90                  95

Asp Glu Ala Arg Phe Lys Arg Pro Val Pro Gly Asp Gln Met Ile
                100                 105                 110

Met Glu Val Thr Phe Glu Lys Thr Arg Arg Gly Leu Thr Arg Phe Lys
                115                 120                 125

Gly Val Ala Leu Val Asp Gly Lys Val Val Cys Glu Ala Thr Met Met
                130                 135                 140

Cys Ala Arg Ser Arg Glu Ala
145                 150
```

<210> SEQ ID NO 23
<211> LENGTH: 720
<212> TYPE: DNA
<213> ORGANISM: Escherichia coli

<400> SEQUENCE: 23

```
atggtcatta aggcgcaaag cccggcgggt ttcgcggaag agtacattat tgaaagtatc    60
tggaataacc gcttccctcc cgggactatt tgcccgcag  aacgtgaact ttcagaatta   120
attggcgtaa cgcgtactac gttacgtgaa gtgttacagc gtctggcacg agatggctgg   180
ttgaccattc aacatggcaa gccgacgaag gtgaataatt tctgggaaac ttccggttta   240
aatatccttg aaacactggc gcgactggat cacgaaagtg tgccgcagct tattgataat   300
ttgctgtcgg tgcgtaccaa tatttccact attttattc  gcaccgcgtt tcgtcagcat   360
cccgataaag cgcaggaagt gctggctacc gctaatgaag tggccgatca cgccgatgcc   420
tttgccgagc tggattacaa catattccgc ggcctggcgt ttgcttccgg caacccgatt   480
tacggtctga ttcttaacgg gatgaaaggg ctgtatacgc gtattggtcg tcactatttc   540
gccaatccgg aagcgcgcag tctggcgctg gcttctacc  acaaactgtc ggcgttgtgc   600
agtgaaggcg cgcacgatca ggtgtacgaa acagtgcgtc gctatgggca tgagagtggc   660
gagatttggc accggatgca gaaaaatctg ccgggtgatt tagccattca ggggcgataa   720
```

<210> SEQ ID NO 24
<211> LENGTH: 239
<212> TYPE: PRT
<213> ORGANISM: Escherichia coli

<400> SEQUENCE: 24

```
Met Val Ile Lys Ala Gln Ser Pro Ala Gly Phe Ala Glu Glu Tyr Ile
  1               5                  10                  15

Ile Glu Ser Ile Trp Asn Asn Arg Phe Pro Pro Gly Thr Ile Leu Pro
                 20                  25                  30

Ala Glu Arg Glu Leu Ser Glu Leu Ile Gly Val Thr Arg Thr Thr Leu
             35                  40                  45

Arg Glu Val Leu Gln Arg Leu Ala Arg Asp Gly Trp Leu Thr Ile Gln
 50                  55                  60

His Gly Lys Pro Thr Lys Val Asn Asn Phe Trp Glu Thr Ser Gly Leu
 65                  70                  75                  80

Asn Ile Leu Glu Thr Leu Ala Arg Leu Asp His Glu Ser Val Pro Gln
                 85                  90                  95

Leu Ile Asp Asn Leu Leu Ser Val Arg Thr Asn Ile Ser Thr Ile Phe
```

```
                100                 105                 110
Ile Arg Thr Ala Phe Arg Gln His Pro Asp Lys Ala Gln Glu Val Leu
            115                 120                 125

Ala Thr Ala Asn Glu Val Ala Asp His Ala Asp Ala Phe Ala Glu Leu
        130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
210                 215                 220

Arg Met Gln Lys Asn Leu Pro Gly Asp Leu Ala Ile Gln Gly Arg
225                 230                 235

<210> SEQ ID NO 25
<211> LENGTH: 930
<212> TYPE: DNA
<213> ORGANISM: Escherichia coli

<400> SEQUENCE: 25
atgacgcaat tgcatttgt gttccctgga cagggttctc aaaccgttgg aatgctggct      60
gatatggcgg cgagctatcc aattgtcgaa gaaacgtttg ctgaagcttc tgcggcgctg     120
ggctacgacc tgtgggcgct gacccagcag gggccagctg aagaactgaa taaaacctgg     180
caaactcagc tgcgctgtt gactgcatct gttgcgctgt atcgcgtatg gcagcagcag     240
ggcggtaaag caccggcaat gatggccggt cacagcctgg gggaatactc cgcgctggtt     300
tgcgctggtg tgattgattt cgctgatgcg gtgcgtctgg ttgagatgcg cggcaagttc     360
atgcaagaag ccgtaccgga aggcacgggc gctatggcgg caatcatcgg tctggatgat     420
gcgtctattg cgaaagcgtg tgaagaagct gcagaaggtc aggtcgtttc tccggtaaac     480
tttaactctc cggacaggt ggttattgcc ggtcataaag aagcggttga gcgtgctggc     540
gctgcctgta aagcggcggg cgcaaaacgc gcgctgccgt taccagtgag cgtaccgtct     600
cactgtgcgc tgatgaaacc agcagccgac aaactggcag tagaattagc gaaaatcacc     660
tttaacgcac caacagttcc tgttgtgaat aacgttgatg tgaaatgcga accaatggt      720 gatgccatcc gtgacgcact ggtacgtcag ttgtataacc cggttcagtg gacgaagtct     780
gttgagtaca tggcagcgca aggcgtagaa catctctatg aagtcggccc gggcaaagtg     840
cttactggcc tgacgaaacg cattgtcgac accctgaccg cctcggcgct gaacgaacct     900
tcagcgatgg cagcggcgct cgagctttaa                                      930

<210> SEQ ID NO 26
<211> LENGTH: 309
<212> TYPE: PRT
<213> ORGANISM: Escherichia coli

<400> SEQUENCE: 26

Met Thr Gln Phe Ala Phe Val Phe Pro Gly Gln Gly Ser Gln Thr Val
1               5                   10                  15

Gly Met Leu Ala Asp Met Ala Ala Ser Tyr Pro Ile Val Glu Glu Thr
            20                  25                  30
```

Phe Ala Glu Ala Ser Ala Ala Leu Gly Tyr Asp Leu Trp Ala Leu Thr
            35                  40                  45

Gln Gln Gly Pro Ala Glu Glu Leu Asn Lys Thr Trp Gln Thr Gln Pro
 50                  55                  60

Ala Leu Leu Thr Ala Ser Val Ala Leu Tyr Arg Val Trp Gln Gln Gln
 65                  70                  75                  80

Gly Gly Lys Ala Pro Ala Met Met Ala Gly His Ser Leu Gly Glu Tyr
                 85                  90                  95

Ser Ala Leu Val Cys Ala Gly Val Ile Asp Phe Ala Asp Ala Val Arg
            100                 105                 110

Leu Val Glu Met Arg Gly Lys Phe Met Gln Glu Ala Val Pro Glu Gly
            115                 120                 125

Thr Gly Ala Met Ala Ala Ile Ile Gly Leu Asp Asp Ala Ser Ile Ala
130                 135                 140

Lys Ala Cys Glu Glu Ala Ala Glu Gly Gln Val Val Ser Pro Val Asn
145                 150                 155                 160

Phe Asn Ser Pro Gly Gln Val Val Ile Ala Gly His Lys Glu Ala Val
                165                 170                 175

Glu Arg Ala Gly Ala Ala Cys Lys Ala Ala Gly Ala Lys Arg Ala Leu
            180                 185                 190

Pro Leu Pro Val Ser Val Pro Ser His Cys Ala Leu Met Lys Pro Ala
            195                 200                 205

Ala Asp Lys Leu Ala Val Glu Leu Ala Lys Ile Thr Phe Asn Ala Pro
            210                 215                 220

Thr Val Pro Val Val Asn Asn Val Asp Val Lys Cys Glu Thr Asn Gly
225                 230                 235                 240

Asp Ala Ile Arg Asp Ala Leu Val Arg Gln Leu Tyr Asn Pro Val Gln
                245                 250                 255

Trp Thr Lys Ser Val Glu Tyr Met Ala Ala Gln Gly Val Glu His Leu
            260                 265                 270

Tyr Glu Val Gly Pro Gly Lys Val Leu Thr Gly Leu Thr Lys Arg Ile
            275                 280                 285

Val Asp Thr Leu Thr Ala Ser Ala Leu Asn Glu Pro Ser Ala Met Ala
            290                 295                 300

Ala Ala Leu Glu Leu
305

<210> SEQ ID NO 27
<211> LENGTH: 1221
<212> TYPE: DNA
<213> ORGANISM: Escherichia coli

<400> SEQUENCE: 27
atgaaacgtg cagtgattac tggcctgggc attgtttcca gcatcggtaa taaccagcag      60
gaagtcctgg catctctgcg tgaaggacgt tcagggatca cttttctctca ggagctgaag    120 gattccggca tgcgtagcca cgtctgggca aacgtaaaac tggataccac tggcctcatt    180
gaccgcaaag ttgtgcgctt tatgagcgac gcatccattt atgcattcct ttctatggag    240
caggcaatcg ctgatgcggg cctctctccg gaagcttacc agaataaccc gcgcgttggc    300
ctgattgcag gttccggcgg cggctccccg cgtttccagg tgttcggcgc tgacgcaatg    360 cgcggccccgc gcggcctgaa agcggttggc ccgtatgtgg tcaccaaagc gatggcatcc    420
ggcgtttctg cctgcctcgc caccccgttt aaaattcatg gcgttaacta ctccatcagc    480

```
tccgcgtgtg cgacttccgc acactgtatc ggtaacgcag tagagcagat ccaactgggc      540
aaacaggaca tcgtgtttgc tggcggcggc gaagagctgt gctgggaaat ggcttgcgaa      600
ttcgacgcaa tgggtgcgct gtctactaaa tacaacgaca ccccggaaaa agcctcccgt      660
acttacgacg ctcaccgtga cggtttcgtt atcgctggcg gcggcggtat ggtagtggtt      720
gaagagctgg aacacgcgct ggcgcgtggt gctcacatct atgctgaaat cgttggctac      780
ggcgcaacct ctgatggtgc agacatggtt gctccgtctg cgaaggcgc agtacgctgc      840 atgaagatgg cgatgcatgg cgttgatacc ccaatcgatt acctgaactc ccacggtact      900
tcgactccgg ttggcgacgt gaaagagctg gcagctatcc gtgaagtgtt cggcgataag      960
agcccggcga tttctgcaac caaagccatg accggtcact ctctgggcgc tgctggcgta     1020
caggaagcta tctactctct gctgatgctg aacacggct ttatcgcccc gagcatcaac      1080
attgaagagc tggacgagca ggctgcgggt ctgaacatcg tgaccgaaac gaccgatcgc     1140
gaactgacca ccgttatgtc taacagcttc ggcttcggcg gcaccaacgc cacgctggta     1200
atgcgcaagc tgaaagatta a                                                1221

<210> SEQ ID NO 28
<211> LENGTH: 406
<212> TYPE: PRT
<213> ORGANISM: Escherichia coli

<400> SEQUENCE: 28

Met Lys Arg Ala Val Ile Thr Gly Leu Gly Ile Val Ser Ser Ile Gly
1               5                   10                  15

Asn Asn Gln Gln Glu Val Leu Ala Ser Leu Arg Glu Gly Arg Ser Gly
            20                  25                  30

Ile Thr Phe Ser Gln Glu Leu Lys Asp Ser Gly Met Arg Ser His Val
        35                  40                  45

Trp Gly Asn Val Lys Leu Asp Thr Thr Gly Leu Ile Asp Arg Lys Val
    50                  55                  60

Val Arg Phe Met Ser Asp Ala Ser Ile Tyr Ala Phe Leu Ser Met Glu
65                  70                  75                  80

Gln Ala Ile Ala Asp Ala Gly Leu Ser Pro Glu Ala Tyr Gln Asn Asn
                85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

Val Gly Pro Tyr Val Val Thr Lys Ala Met Ala Ser Gly Val Ser Ala
    130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Gly Glu Glu
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
    210                 215                 220

His Arg Asp Gly Phe Val Ile Ala Gly Gly Gly Met Val Val Val
225                 230                 235                 240
```

Glu Glu Leu Glu His Ala Leu Ala Arg Gly Ala His Ile Tyr Ala Glu
            245                 250                 255

Ile Val Gly Tyr Gly Ala Thr Ser Asp Gly Ala Asp Met Val Ala Pro
        260                 265                 270

Ser Gly Glu Gly Ala Val Arg Cys Met Lys Met Ala Met His Gly Val
    275                 280                 285

Asp Thr Pro Ile Asp Tyr Leu Asn Ser His Gly Thr Ser Thr Pro Val
    290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Ala Met Thr Gly His Ser Leu Gly
                325                 330                 335

Ala Ala Gly Val Gln Glu Ala Ile Tyr Ser Leu Leu Met Leu Glu His
            340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr
    370                 375                 380

Val Met Ser Asn Ser Phe Gly Phe Gly Gly Thr Asn Ala Thr Leu Val
385                 390                 395                 400

Met Arg Lys Leu Lys Asp
                405

<210> SEQ ID NO 29
<211> LENGTH: 1242
<212> TYPE: DNA
<213> ORGANISM: Escherichia coli

<400> SEQUENCE: 29
gtgtctaagc gtcgtgtagt tgtgaccgga ctgggcatgt tgtctcctgt cggcaatacc      60
gtagagtcta cctggaaagc tctgcttgcc ggtcagagtg gcatcagcct aatcgaccat     120
ttcgatacta gcgcctatgc aacgaaattt gctggcttag taaaggattt taactgtgag     180
gacattatct cgcgcaaaga acagcgcaag atggatgcct tcattcaata tggaattgtc     240
gctggcgttc aggccatgca ggattctggc cttgaaataa cggaagagaa cgcaacccgc     300
attggtgccg caattggctc cgggattggc ggcctcggac tgatcgaaga aaaccacaca     360
tctctgatga acggtggtcc acgtaagatc agcccattct tcgttccgtc aacgattgtg     420
aacatggtgg caggtcatct gactatcatg tatggcctgc gtggcccgag catctctatc     480
gcgactgcct gtacttccgg cgtgcacaac attggccatg ctgcgcgtat tatcgcgtat     540
ggcgatgctg acgtgatggt tgcaggtggc gcagagaaag ccagtacgcc gctgggcgtt     600
ggtggttttg cgcggcacg tgcattatct acccgcaatg ataacccgca agcggcgagc     660
cgcccgtggg ataaagagcg tgatggtttc gtactgggcg atggtgccgg tatgctggta     720
cttgaagagt acgaacacgc gaaaaaacgg ggtgcgaaaa tttacgctga actcgtcggc     780
tttggtatga gcagcgatgc ttatcatatg acgtcaccgc cagaaaatgg cgcaggcgca     840
gctctggcga tggcaaatgc tctgcgtgat gcaggcattg aagcgagtca gattggctac     900
gttaacgcgc acggtacttc tacgccggct ggcgataaag ctgaagcgca ggcggtgaaa     960
accatcttcg gtgaagctgc aagccgtgtg ttggtaagct ccacgaaatc tatgaccggt    1020
cacctgttag gtcggcgggt gcagtagaa tctatctact ccatcctggc gctgcgcgat    1080
caggctgttc cgccaaccat caacctggat aacccggatg aaggttgcga tctggatttc    1140

```
gtaccgcacg aagcgcgtca ggttagcgga atggaataca ctctgtgtaa ctccttcggc    1200
ttcggtggca ctaatggttc tttgatcttt aaaaagatct aa                      1242
```

<210> SEQ ID NO 30
<211> LENGTH: 413
<212> TYPE: PRT
<213> ORGANISM: Escherichia coli
<400> SEQUENCE: 30

```
Met Ser Lys Arg Arg Val Val Thr Gly Leu Gly Met Leu Ser Pro
1               5                   10                  15

Val Gly Asn Thr Val Glu Ser Thr Trp Lys Ala Leu Leu Ala Gly Gln
            20                  25                  30

Ser Gly Ile Ser Leu Ile Asp His Phe Asp Thr Ser Ala Tyr Ala Thr
        35                  40                  45

Lys Phe Ala Gly Leu Val Lys Asp Phe Asn Cys Glu Asp Ile Ile Ser
    50                  55                  60

Arg Lys Glu Gln Arg Lys Met Asp Ala Phe Ile Gln Tyr Gly Ile Val
65                  70                  75                  80

Ala Gly Val Gln Ala Met Gln Asp Ser Gly Leu Glu Ile Thr Glu Glu
                85                  90                  95

Asn Ala Thr Arg Ile Gly Ala Ala Ile Gly Ser Gly Ile Gly Gly Leu
            100                 105                 110

Gly Leu Ile Glu Glu Asn His Thr Ser Leu Met Asn Gly Gly Pro Arg
        115                 120                 125

Lys Ile Ser Pro Phe Phe Val Pro Ser Thr Ile Val Asn Met Val Ala
    130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
            180                 185                 190

Lys Ala Ser Thr Pro Leu Gly Val Gly Gly Phe Gly Ala Ala Arg Ala
        195                 200                 205

Leu Ser Thr Arg Asn Asp Asn Pro Gln Ala Ala Ser Arg Pro Trp Asp
    210                 215                 220

Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
                245                 250                 255

Glu Leu Val Gly Phe Gly Met Ser Ser Asp Ala Tyr His Met Thr Ser
            260                 265                 270

Pro Pro Glu Asn Gly Ala Gly Ala Ala Leu Ala Met Ala Asn Ala Leu
        275                 280                 285

Arg Asp Ala Gly Ile Glu Ala Ser Gln Ile Gly Tyr Val Asn Ala His
    290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

Ser Met Thr Gly His Leu Leu Gly Ala Ala Gly Ala Val Glu Ser Ile
            340                 345                 350

Tyr Ser Ile Leu Ala Leu Arg Asp Gln Ala Val Pro Pro Thr Ile Asn
```

```
                355                 360                 365
Leu Asp Asn Pro Asp Glu Gly Cys Asp Leu Asp Phe Val Pro His Glu
        370                 375                 380

Ala Arg Gln Val Ser Gly Met Glu Tyr Thr Leu Cys Asn Ser Phe Gly
385                 390                 395                 400

Phe Gly Gly Thr Asn Gly Ser Leu Ile Phe Lys Lys Ile
                405                 410

<210> SEQ ID NO 31
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 31
gaccttaaaa ccctaaaggc ttaagggcat ccgcttacag aca            43

<210> SEQ ID NO 32
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 32
ggagaaaata ccgcatcagg cgcctcagga gagcgttcac cgac            44

<210> SEQ ID NO 33
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 33
taaaccatgg cgactcaaca acagaaca                              28

<210> SEQ ID NO 34
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 34
ctatgtcgac ttaggcggtt ttatcgtcag tatca                      35

<210> SEQ ID NO 35
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 35
tcgacataga tctagaactt actcggaagc ttcttaatta agaggatcca ttgacgtcta   60
tgaattcgtt t                                                        71

<210> SEQ ID NO 36
<211> LENGTH: 67
<212> TYPE: DNA
<213> ORGANISM: Artificial Sequence
<220> FEATURE:
```

<223> OTHER INFORMATION: Synthetic polynucleotide

<400> SEQUENCE: 36
aaacgaattc atagacgtca atggatcctc ttaattaaga agcttccgag taagttctag    60
atctatg                                                              67

<210> SEQ ID NO 37
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 37
aaaagtcgac aaccgaaaag tgactgagcg tacatgtata cgaagattat tggtactggc    60

<210> SEQ ID NO 38
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 38
aaaaggatcc ttagaaacga accagcgcgg                                     30

<210> SEQ ID NO 39
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 39
aaaagtcgac ataaaataag gcttacagag aacatgtata cgaagattat tggtactggc    60

<210> SEQ ID NO 40
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 40
aaaaggatcc ttagaaacga accagcgcgg                                     30

<210> SEQ ID NO 41
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 41
tagaggccag cctggccata aggagatata catatgaaga aggtttggct taaccgttat    60

<210> SEQ ID NO 42
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 42
cggttttggt ttccactcta acatggttta ttcctccttt cattaggctt tattgtccac    60

```
tttg                                                          64

<210> SEQ ID NO 43
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 43
caaagtggac aataaagcct aatgaaagga ggaataaacc atgttagagt ggaaaccaaa    60
accg                                                          64

<210> SEQ ID NO 44
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 44
tggtggccag tttggcctta tacccgcggc tcggccggaa t                  41

<210> SEQ ID NO 45
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 45
taaaccatgg cgactcaaca acagaaca                                 28

<210> SEQ ID NO 46
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 46
ctatgtcgac ttaggcggtt ttatcgtcag tatca                         35

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
tgtggaattg tgagcggata                                          20

<210> SEQ ID NO 48
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 48
cgcttctgcg ttctgattt                                           19

<210> SEQ ID NO 49
```

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
gtcgtcggtt ccgatgtact                                              20

<210> SEQ ID NO 50
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 50
aaaaggatcc ttagaccatg tacatcccgc c                                 31

<210> SEQ ID NO 51
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 51
acaggaagag tatcatgact actaac                                       26

<210> SEQ ID NO 52
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 52
ttaggcctcc cggctacgag cac                                          23

<210> SEQ ID NO 53
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 53
actaagtcga cataaggaga tatacatatg acc                               33

<210> SEQ ID NO 54
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 54
aggtcaagct tattagtctt tacg                                         24

<210> SEQ ID NO 55
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 55
```

```
agtaagcttg agtttaggaa gagtatcatg                                        30

<210> SEQ ID NO 56
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 56
aagctgacgt cttaggcctc ccggctacg                                         29

<210> SEQ ID NO 57
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 57
gatacgaccc gtaaacttgc aaccattttt ggc                                    33

<210> SEQ ID NO 58
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 58
cgcttctgcg ttctgattt                                                    19

<210> SEQ ID NO 59
<211> LENGTH: 5905
<212> TYPE: DNA
<213> ORGANISM: Artificial Sequence
<220> FEATURE:
<223> OTHER INFORMATION: Synthetic polynucleotide

<400> SEQUENCE: 59
ggcatccgct tacagacaag ctgtgaccgt ctccgggagc tgcatgtgtc agaggttttc        60
accgtcatca ccgaaacgcg cgaggcagca gatcaattcg cgcgcgaagg cgaagcggca      120
tgcatttacg ttgacaccat cgaatggtgc aaaaccttc gcggtatggc atgatagcgc       180
ccggaagaga gtcaattcag ggtggtgaat gtgaaaccag taacgttata cgatgtcgca      240
gagtatgccg gtgtctctta tcagaccgtt tcccgcgtgg tgaaccaggc cagccacgtt      300
tctgcgaaaa cgcgggaaaa agtggaagcg gcgatggcgg agctgaatta cattcccaac      360
cgcgtggcac aacaactggc gggcaaacag tcgttgctga ttggcgttgc cacctccagt      420
ctggccctgc acgcgccgtc gcaaattgtc gcggcgatta atctcgcgc cgatcaactg       480 ggtgccagcg tggtggtgtc gatggtagaa cgaagcggcg tcgaagcctg taaagcggcg      540
gtgcacaatc ttctcgcgca acgcgtcagt gggctgatca ttaactatcc gctggatgac      600
caggatgcca ttgctgtgga agctgcctgc actaatgttc cggcgttatt tcttgatgtc      660
tctgaccaga cacccatcaa cagtattatt ttctcccatg aagacggtac gcgactgggc      720
gtggagcatc tggtcgcatt gggtcaccag caaatcgcgc tgttagcggg cccattaagt      780
tctgtctcgg cgcgtctgcg tctggctggc tggcataaat atctcactcg caatcaaatt      840
cagccgatag cggaacggga aggcgactgg agtgccatgt ccggttttca acaaaccatg      900
```

```
caaatgctga atgagggcat cgttcccact gcgatgctgg ttgccaacga tcagatggcg    960
ctgggcgcaa tgcgcgccat taccgagtcc gggctgcgcg ttggtgcgga tatctcggta   1020
gtgggatacg acgataccga agacagctca tgttatatcc cgccgttaac caccatcaaa   1080
caggattttc gcctgctggg gcaaaccagc gtggaccgct tgctgcaact ctctcagggc   1140
caggcggtga agggcaatca gctgttgccc gtctcactgg tgaaaagaaa accaccctg    1200
gcgcccaata cgcaaaccgc ctctccccgc gcgttggccg attcattaat gcagctggca   1260
cgacaggttt cccgactgga aagcgggcag tgagcgcaac gcaattaatg taagttagcg   1320
cgaattgatc tggtttgaca gcttatcatc gactgcacgg tgcaccaatg cttctggcgt   1380
caggcagcca tcggaagctg tggtatggct gtgcaggtcg taaatcactg cataattcgt   1440
gtcgctcaag gcgcactccc gttctggata atgttttttg cgccgacatc ataacggttc   1500
tggcaaatat tctgaaatga gctgttgaca attaatcatc cggctcgtat aatgtgtgga   1560
attgtgagcg gataacaatt tcacacagga acagcgccg ctgagaaaaa gcgaagcggc    1620
actgctcttt aacaatttat cagacaatct gtgtgggcac tcgaccggaa ttatcgatta   1680
actttattat taaaaattaa agaggtatat attaatgtat cgattaaata aggaggaata   1740
aaccatggat ccgagctcga gatctgcagc tggtaccata tgggaattcg aagctttcta   1800
gaacaaaaac tcatctcaga agaggatctg aatagcgccg tcgaccatca tcatcatcat   1860
cattgagttt aaacggtctc cagcttggct gttttggcgg atgagagaag attttcagcc   1920
tgatacagat taaatcagaa cgcagaagcg gtctgataaa acagaatttg cctggcggca   1980
gtagcgcggt ggtcccacct gaccccatgc cgaactcaga agtgaaacgc cgtagcgccg   2040
atggtagtgt ggggtctccc catgcgagag tagggaactg ccaggcatca aataaaacga   2100
aaggctcagt cgaaagactg ggcctttcgt tttatctgtt gtttgtcggt gaacgctctc   2160
ctgaggcgcc tgatgcggta ttttctcctt acgcatctgt gcggtatttc acaccgcata   2220
tggtgcactc tcagtacaat ctgctctgat gccgcatagt taagccagcc ccgacacccg   2280
ccaacacccg ctgacgagct tagtaaagcc ctcgctagat tttaatgcgg atgttgcgat   2340
tacttcgcca actattgcga taacaagaaa aagccagcct ttcatgatat atctcccaat   2400
ttgtgtaggg cttattatgc acgcttaaaa ataataaaag cagacttgac ctgatagttt   2460
ggctgtgagc aattatgtgc ttagtgcatc taacgcttga gttaagccgc gccgcgaagc   2520
ggcgtcggct tgaacgaatt gttagacatt atttgccgac taccttggtg atctcgcctt   2580
tcacgtagtg gacaaattct tccaactgat ctgcgcgcga ggccaagcga tcttcttctt   2640
gtccaagata agcctgtcta gcttcaagta tgacgggctg atactgggcc ggcaggcgct   2700
ccattgccca gtcggcagcg acatccttcg gcgcgatttt gccggttact gcgctgtacc   2760
aaatgcggga caacgtaagc actacatttc gctcatcgcc agcccagtcg ggcggcgagt   2820
tccatagcgt taaggtttca tttagcgcct caaatagatc ctgttcagga accggatcaa   2880
agagttcctc cgccgctgga cctaccaagg caacgctatg ttctcttgct tttgtcagca   2940
agatagccag atcaatgtcg atcgtggctg gctcgaagat acctgcaaga atgtcattgc   3000
gctgccattc tccaaattgc agttcgcgct tagctggata cgccacgga atgatgtcgt    3060
cgtgcacaac aatggtgact tctacagcgc ggagaatctc gctctctcca ggggaagccg   3120
aagtttccaa aaggtcgttg atcaaagctc gccgcgttgt ttcatcaagc cttacggtca   3180
ccgtaaccag caaatcaata tcactgtgtg gcttcaggcc gccatccact gcggagccgt   3240
acaaatgtac ggccagcaac gtcggttcga gatggcgctc gatgacgcca actacctctg   3300
```

```
atagttgagt cgatacttcg gcgatcaccg cttccctcat gatgtttaac tttgttttag      3360
ggcgactgcc ctgctgcgta acatcgttgc tgctccataa catcaaacat cgacccacgg      3420
cgtaacgcgc ttgctgcttg gatgcccgag gcatagactg taccccaaaa aaacagtcat      3480
aacaagccat gaaaaccgcc actgcgccgt taccaccgct gcgttcggtc aaggttctgg      3540
accagttgcg tgagcgcata cgctacttgc attacagctt acgaaccgaa caggcttatg      3600
tccactgggt tcgtgccttc atccgttttcc acggtgtgcg tcaccggca accttgggca      3660 gcagcgaagt cgaggcattt ctgtcctggc tggcgaacga gcgcaaggtt tcggtctcca      3720
cgcatcgtca ggcattggcg gccttgctgt tcttctacgg caaggtgctg tgcacggatc      3780
tgccctggct tcaggagatc ggaagacctc ggccgtcgcg gcgcttgccg gtggtgctga      3840
ccccggatga agtggttcgc atcctcggtt ttctggaagg cgagcatcgt tgttcgccc       3900 agcttctgta tggaacgggc atgcggatca gtgagggttt gcaactgcgg gtcaaggatc      3960
tggatttcga tcacggcacg atcatcgtgc gggagggcaa gggctccaag gatcgggcct      4020
tgatgttacc cgagagcttg gcacccagcc tgcgcgagca ggggaattaa ttcccacggg      4080
ttttgctgcc cgcaaacggg ctgttctggt gttgctagtt tgttatcaga atcgcagatc      4140
cggcttcagc cggtttgccg gctgaaagcg ctatttcttc cagaattgcc atgattttt      4200 ccccacggga ggcgtcactg gctcccgtgt tgtcggcagc tttgattcga taagcagcat      4260
cgcctgtttc aggctgtcta tgtgtgactg ttgagctgta acaagttgtc tcaggtgttc      4320
aatttcatgt tctagttgct ttgtttttact ggtttcacct gttctattag gtgttacatg      4380
ctgttcatct gttacattgt cgatctgttc atggtgaaca gctttgaatg caccaaaaac      4440
tcgtaaaagc tctgatgtat ctatctttt tacaccgttt tcatctgtgc atatggacag      4500
ttttcccttt gatatgtaac ggtgaacagt tgttctactt ttgtttgtta gtcttgatgc      4560
ttcactgata gatacaagag ccataagaac ctcagatcct tccgtattta gccagtatgt      4620
tctctagtgt ggttcgttgt ttttgcgtga gccatgagaa cgaaccattg agatcatact      4680
tactttgcat gtcactcaaa aattttgcct caaaactggt gagctgaatt tttgcagtta      4740
aagcatcgtg tagtgttttt cttagtccgt tatgtaggta ggaatctgat gtaatggttg      4800
ttggtatttt gtcaccattc atttttatct ggttgttctc aagttcggtt acgagatcca      4860
tttgtctatc tagttcaact tggaaaatca acgtatcagt cgggcggcct cgcttatcaa      4920
ccaccaattt catattgctg taagtgttta aatctttact tattggtttc aaaacccatt      4980
ggttaagcct tttaaactca tggtagttat tttcaagcat taacatgaac ttaaattcat      5040
caaggctaat ctctatattt gccttgtgag ttttcttttg tgttagttct tttaataacc      5100
actcataaat cctcatagag tatttgtttt caaaagactt aacatgttcc agattatatt      5160
ttatgaattt ttttaactgg aaaagataag gcaatatctc ttcactaaaa actaattcta      5220 attttcgct tgagaacttg gcatagtttg tccactggaa atctcaaag cctttaacca        5280 aaggattcct gatttccaca gttctcgtca tcagctctct ggttgcttta gctaatacac      5340
cataagcatt ttccctactg atgttcatca tctgagcgta ttggttataa gtgaacgata      5400
ccgtccgttc tttccttgta gggttttcaa tcgtggggtt gagtagtgcc acacagcata      5460
aaattagctt ggtttcatgc tccgttaagt catagcgact aatcgctagt tcatttgctt      5520
tgaaaacaac taattcagac atacatctca attggtctag gtgattttaa tcactatacc      5580
aattgagatg ggctagtcaa tgataattac tagtcctttt cctttgagtt gtgggtatct      5640
```

```
gtaaattctg ctagaccttt gctggaaaac ttgtaaattc tgctagaccc tctgtaaatt      5700
ccgctagacc tttgtgtgtt tttttgttt atattcaagt ggttataatt tatagaataa       5760
agaaagaata aaaaagata aaagaatag atcccagccc tgtgtataac tcactacttt        5820
agtcagttcc gcagtattac aaaaggatgt cgcaaacgct gtttgctcct ctacaaaaca      5880
gaccttaaaa ccctaaaggc ttaag                                             5905

<210> SEQ ID NO 60
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 60
ataaaataag gcttacagag aac                                                23

<210> SEQ ID NO 61
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 61
aaccgaaaag tgactgagcg tac                                                23

<210> SEQ ID NO 62
<211> LENGTH: 906
<212> TYPE: DNA
<213> ORGANISM: Artificial Sequence
<220> FEATURE:
<223> OTHER INFORMATION: Synthetic polynucleotide

<400> SEQUENCE: 62
atgaccttag agtggaaacc aaaaccgaaa ttacctcagc ttcttgacga ccacttcggc        60
ctgcatggtt tagtattccg cagaacgttt gccataagaa gctacgaagt aggaccagat      120
cgttctacct ctatacttgc tgtgatgaat catatgcagg aagccacgtt aaatcacgca      180
aagagcgtcg ggatccttgg ggacggattc ggcaccacat tggaaatgag taagcgggac      240
ctgatgtggg ttgttcgtcg tacccacgta gcggtcgaac ggtatccaac atggggcgat      300
actgttgaag tggagtgctg gattggcgct tccggaaaca acggaatgcg cagagatttt      360
ctggtgcggg actgtaaaac tggggaaatc ttaacgcgct gtacctccct gtccgttctg      420
atgaacacgc gtacccggag attaagtacg attccggacg aagtccgtgg tgaaatcggt      480
cccgctttta ttgacaacgt ggcggtaaaa gacgacgaga tcaaaaagtt gcagaaattg      540
aacgattcca cagcagatta catacagggc ggtcttacgc cccgttggaa cgacttggat      600
gtgaatcagc acgtaaataa ccttaaatat gtggcgtggg tgttcgagac cgttcccgac      660
tctatttttg aaagtcacca catttccagc tttacgctgg agtacagacg cgagtgtacg      720
cgcgattccg ttttacgttc cctcaccacg gtgtctggcg atcttccga agctgggtta       780 gtgtgtgatc acttgctgca acttgaaggc ggaagtgaag ttcttcgggc ccgcacggaa      840
tggcgtccca aactgaccga ttccttccgc ggaatatcag taattccggc cgagccgcgg      900
gtataa                                                                  906

<210> SEQ ID NO 63
<211> LENGTH: 301
```

<210> SEQ ID NO 63
<211> LENGTH: 300
<212> TYPE: PRT
<213> ORGANISM: Artificial Sequence
<220> FEATURE:
<223> OTHER INFORMATION: Synthetic polypeptide

<400> SEQUENCE: 63

```
Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
            20                  25                  30

Arg Ser Tyr Glu Val Gly Pro Asp Arg Ser Thr Ser Ile Leu Ala Val
        35                  40                  45

Met Asn His Met Gln Glu Ala Thr Leu Asn His Ala Lys Ser Val Gly
50                  55                  60

Ile Leu Gly Asp Gly Phe Gly Thr Thr Leu Glu Met Ser Lys Arg Asp
65                  70                  75                  80

Leu Met Trp Val Val Arg Arg Thr His Val Ala Val Glu Arg Tyr Pro
                85                  90                  95

Thr Trp Gly Asp Thr Val Glu Val Glu Cys Trp Ile Gly Ala Ser Gly
            100                 105                 110

Asn Asn Gly Met Arg Arg Asp Phe Leu Val Arg Asp Cys Lys Thr Gly
        115                 120                 125

Glu Ile Leu Thr Arg Cys Thr Ser Leu Ser Val Leu Met Asn Thr Arg
130                 135                 140

Thr Arg Arg Leu Ser Thr Ile Pro Asp Glu Val Arg Gly Glu Ile Gly
145                 150                 155                 160

Pro Ala Phe Ile Asp Asn Val Ala Val Lys Asp Glu Ile Lys Lys
                165                 170                 175

Leu Gln Lys Leu Asn Asp Ser Thr Ala Asp Tyr Ile Gln Gly Gly Leu
            180                 185                 190

Thr Pro Arg Trp Asn Asp Leu Asp Val Asn Gln His Val Asn Asn Leu
        195                 200                 205

Lys Tyr Val Ala Trp Val Phe Glu Thr Val Pro Asp Ser Ile Phe Glu
210                 215                 220

Ser His His Ile Ser Ser Phe Thr Leu Glu Tyr Arg Arg Glu Cys Thr
225                 230                 235                 240

Arg Asp Ser Val Leu Arg Ser Leu Thr Thr Val Ser Gly Gly Ser Ser
                245                 250                 255

Glu Ala Gly Leu Val Cys Asp His Leu Leu Gln Leu Glu Gly Gly Ser
            260                 265                 270

Glu Val Leu Arg Ala Arg Thr Glu Trp Arg Pro Lys Leu Thr Asp Ser
        275                 280                 285

Phe Arg Gly Ile Ser Val Ile Pro Ala Glu Pro Arg Val
290                 295                 300
```

<210> SEQ ID NO 64
<211> LENGTH: 682
<212> TYPE: DNA
<213> ORGANISM: Artificial Sequence
<220> FEATURE:
<223> OTHER INFORMATION: Synthetic polynucleotide

<400> SEQUENCE: 64

```
gatatctcgg tagtgggata cgacgatacc gaagacagct catgttatat cccgccgtta      60
accaccatca aacaggattt tcgcctgctg gggcaaacca gcgtggaccg cttgctgcaa     120
ctctctcagg gccaggcggt gaagggcaat cagctgttgc ccgtctcact ggtgaaaaga     180
```

```
aaaaccaccc tggcgcccaa tacgcaaacc gcctctcccc gcgcgttggc cgattcatta    240
atgcagctgg cacgacaggt ttcccgactg gaaagcgggc agtaataatt taaattggtt    300
tgacagctta tcatcgactg cacggtgcac caatgcttct ggcgtcaggc agccatcgga    360
agctgtggta tggctgtgca ggtcgtaaat cactgcataa ttcgtgtcgc tcaaggcgca    420
ctcccgttct ggataatgtt ttttgcgccg acataattgt gagcgctcac aatttctgaa    480
atgagctgtt gacaattaat catccggctc gtataatgtg tggaattgtg agcggataac    540
aatttcacac aggaaacagc gccgctgaga aaaagcgaag cggcactgct ctttaacaat    600
ttatcagaca atctgtgtgg gcactcgacc ggaattatcg attaacttta ttattaaaaa    660
ttaaaggagg aataaaccat gg                                             682
```

PRODUCTION OF FATTY ALCOHOLS FROM ENGINEERED MICROORGANISMS

CROSS-REFERENCE TO RELATED APPLICATIONS

The present application is a national stage application filed under 35 USC §371 and claims priority to international application to PCT International Application No. PCT/US2013/051340, filed Jul. 19, 2013, which claims priority to previously filed U.S. Provisional Application. No. 61/674,053 filed Jul. 20, 2012; PCT International Application No. PCT/US2012/069444 filed Dec. 13, 2012, PCT International Application No. PCT/US2012/069553 filed Dec. 13, 2012 and PCT International Application No. PCT/US2013/037472 filed Apr. 19, 2013, all of which are hereby incorporated in their entireties for all purposes.

FIELD OF THE INVENTION

This invention relates to recombinant microorganisms and particularly recombinant bacterial microorganisms exhibiting selective enhanced production of C12 to C14 fatty alcohols and to the fatty alcohol compositions produced by the engineered microorganisms.

REFERENCE TO A SEQUENCE LISTING, A TABLE OR A COMPUTER PROGRAM LISTING APPENDIX SUBMITTED AS AN ASCII TEXT FILE

Sequence Listing written in file CX5-118WO2_ST25.TXT, created on Jul. 17, 2013, 98,697 bytes, machine format IBM-PC, MS Windows operating system, is hereby incorporated by reference.

BACKGROUND OF THE INVENTION

Crude petroleum has traditionally been used as a primary source for raw materials for producing numerous specialty chemicals. Particular specialty chemicals that can be produced from the petrochemical raw materials include fatty alcohols. Fatty alcohols have many industrial and commercial uses. For example, fatty alcohols act as surfactants which are useful in personal care and household products, such as detergents. Fatty alcohols are also used in waxes, lubricating oils, cosmetics and solvents. However, obtaining fatty alcohols from crude petroleum requires a significant amount of energy and involves the use of a non-renewable energy source.

Further, even those fatty alcohols that are obtained from renewable sources, such as from plant or animal derived fatty acids, generally are prepared using a hydrogenation step. Hydrogenation is a costly process step but is utilized to eliminate the double bonds of unsaturated fatty acids. A number of prior art references disclose genetically engineered microorganisms that produce products including fatty acid derivatives such as fatty acid esters and fatty alcohols. For example, reference is made to International application publications WO 2007/136762; WO 2008/119082; WO2010/075483; WO2011/008535; and WO 2011/019858; and U.S. Pat. No. 6,143,538. However a need still exists in the field for improved fatty alcohol production from bioengineered microorganisms that is efficient and cost effective and further that is tailored for use in particular industrial applications. In certain industrial applications, the presence of one or more double bonds in a fatty alcohol is not a desirable characteristic because the double bond lowers the melting point, reduces the shelf-life and reduces the heat stability of the fatty alcohol. Therefore, compositions and methods that provide products having increased saturation levels in fatty alcohols are also commercially beneficial. In addition, it would be beneficial to optimize specific blends of fatty alcohols (e.g., blends of predominantly C12 and C14 fatty alcohol carbon chain lengths) to target particular industrial applications that utilize these fatty alcohols or derivatives thereof.

SUMMARY OF THE INVENTION

The invention relates to methods for selective enhanced production of C12 to C14 fatty alcohol compositions and blends and engineered microbial cells which have been modified to comprise a nucleic acid sequence which codes for a protein having the enzymatic activity of a β-ketoacyl acyl carrier protein ("ACP") synthase III and a nucleic acid sequence which codes for a heterologous protein having fatty alcohol reductase ("FAR") activity. The inventive methods further comprise the expression of genes coding for enzymes having FAR activity and β-ketoacyl ACP synthase II activity. The fatty alcohol composition produced by the modified microbial organisms according to the invention may be used inter alia in detergent compositions, cleaning compositions and personal care compositions.

In one aspect, the invention provides an engineered prokaryotic cell comprising two recombinant polynucleotides the first polynucleotide encoding a heterologous fatty alcohol forming reductase ("FAR") and the second polynucleotide encoding a β-ketoacyl acyl carrier protein synthase II ("FabH"). In some embodiments, the engineered cell when cultured in the presence of a carbon source under suitable culture conditions produces a fatty alcohol composition having a chain length profile of at least 50% of C12 to C16 fatty alcohols. In some embodiments, the engineered cell is a bacterial cell such as, *E. coli*. In other embodiments, the engineered cell produces a fatty alcohol composition with a carbon chain length profile of at least 60% (at least 65%, at least 70%, at least 75%, at least 80%, at least 85%, and at least 90%) of C12 to C16 fatty alcohols relative to the total fatty alcohol composition produced by engineered host cell. In some embodiments, the engineered cell produces a fatty alcohol composition with a carbon chain length profile of at least 60% (65%, 70%, 75%, 80%, 85% and 90%) of C12 to C14 fatty alcohols relative to the total fatty alcohol composition produced by the cell. In various embodiments, the FAR comprises an amino acid sequence having at least 75% (at least 80%, at least 85%, at least 90%, at least 95%, at least 96%, at least 97%, at least 98%, at least 99% and even 100%) sequence identity to the amino acid sequence of SEQ ID NO:2. In other embodiments the FAR comprises an amino acid sequence having at least 95% (96%, 97%, 98%, 99% and even 100%) sequence identity to the amino acid sequence of SEQ ID NO:4. SEQ ID NO: 6 or SEQ ID NO: 8. In further embodiments, the FabH ("FabH") comprises an amino acid sequence having at least 80% (85%, 88%, 90%, 92%, 94%, 96%, 98%, 99% and 100%) sequence identity with SEQ ID NO: 10.

In a second aspect, the invention provides an engineered prokaryotic cell comprising three recombinant polynucleotides, the first polynucleotide encoding a heterologous fatty alcohol forming reductase ("FAR"), the second polynucleotide encoding a β-ketoacyl acyl carrier protein synthase III ("FabH") and the third polynucleotide encoding a thioesterase (TE). In some embodiments the TE comprises an amino acid sequence comprising at least 85% (90%, 92%, 95%, 97%, 98%, 99% and even 100%) sequence identity to SEQ ID NO: 12 or SEQ ID NO: 63. In further embodiments, the engineered prokaryotic cell will optionally comprise a fourth recombinant polynucleotide (e.g., an introduced polynucleotide encoding a FadD such as an *E. coli* FadD having at least 95% (such as 95%, 96%, 97%, 98%, 99% and even 100%) sequence identity to SEQ ID NO: 16.

In a third aspect, the engineered prokaryotic cell according to the first aspect and the second aspect further comprises one or more introduced polynucleotide sequences encoding an enzyme having FabD activity and/or FabG activity. In some embodiments, the polynucleotide encoding the enzyme having FabD activity comprises an amino acid sequence having at least 90% (91%, 92%, 93%, 94%, 95%, 96%, 97%, 98%, 99% and even 100%) sequence identity to SEQ ID NO: 26. In some embodiments, the polynucleotide encoding the enzyme having FabG activity comprises an amino acid sequence having at least 90% (91%, 92%, 93%, 94%, 95%, 96%, 97%, 98%, 99% and even 100%) sequence identity to SEQ ID NO: 18.

In yet a further embodiment, the engineered prokaryotic cells according to the first aspect, the second aspect and the third aspect further comprise one or more introduced polynucleotide sequences encoding an enzyme having FabI activity and/or FabZ activity. In some embodiments, the polynucleotide encoding the enzyme having FabI activity comprises an amino acid sequence having at least 90% (91%, 92%, 93%, 94%, 95%, 96%, 97%, 98%, 99% and even 100%) sequence identity to SEQ ID NO: 20. In other embodiments, the polynucleotide sequence encoding the enzyme having FabZ activity comprises an amino acid sequence having at least 90% (91%, 92%, 93%, 94%, 95%, 96%, 97%, 98%, 99% and even 100%) sequence identity to SEQ ID NO: 22.

In yet a further embodiment, the engineered prokaryotic cells according to the first aspect, the second aspect and the third aspect comprise a gene selected from one or more of fadE, fadR, fadD, fabB, fabH and fabF which has been attenuated.

In a fourth aspect, the invention provides a fatty alcohol composition produced by the engineered cells according to the first, second or third aspect. In some embodiments, the fatty alcohol composition produced by the engineered cells is recovered from the cell culture. In some embodiments the fatty alcohol composition is a component of a detergent composition, a personal care composition, a surfactant composition and/or a cleaning composition.

In a fifth aspect, the invention provides a method of producing a fatty alcohol composition comprising providing an engineered cell according to the first, second or third aspects, culturing the engineered host cell under suitable culture conditions in the presence of a carbon source; producing fatty alcohols; and optionally recovering the fatty alcohols from the culture medium. In some embodiments, the carbon source comprises a fermentable sugar. In some embodiments, the fermentable sugars are obtained from a cellulosic feedstock obtained from biomass such as biomass selected from grain (e.g. corn), corn stover, corn cobs, wheat straw, bagasse and beet pulp. In some embodiments the biomass has been pretreated. In some embodiments at least 1 g/L of fatty alcohols are produced by the engineered cells. In further embodiments, the total fatty alcohol composition produced by the engineered cells comprises at least 60% (70%, 75%, 80%, 85%, 90%, and 95%) of C12 to C14 fatty alcohols.

In a sixth aspect, the invention provides a vector comprising a first polynucleotide sequence encoding a fatty alcohol forming reductase ("FAR") and a second polynucleotide sequence encoding a β-ketoacyl acyl carrier protein synthase III (KAS-III), wherein the polynucleotide sequences are operably linked to a promoter that is functional in a prokaryotic host cell. In some embodiments, the vector is chromosomally integrated into a host cell. In other embodiments, the promoter is the same for the first polynucleotide sequence encoding the FAR and the second polynucleotide sequence encoding the KAS-III. In still other embodiments, the promoter is different for the first polynucleotide sequence encoding FAR and the second polynucleotide sequence encoding KAS-III. In further embodiments, the polynucleotide encoding the KAS-III is operably linked to a ribosome binding sequence comprising a nucleic acid sequence having at least 95% sequence identity to SEQ ID NO: 60 or SEQ ID NO: 61, or at least 95% sequence identity to bases 1-22 of SEQ ID NO: 60 or bases 2-23 of SEQ ID NO: 61. In yet other embodiments, the vector comprises a third polynucleotide sequence encoding a TE comprising an amino acid sequence having at least 90% sequence identity to SEQ ID NO: 12 or SEQ ID NO: 63. In further embodiments, the vector optionally comprises a fourth recombinant polynucleotide (e.g., an introduced polynucleotide encoding a FadD such as an *E. coli* FadD having at least 95% (such as at least 95%, 96%, 97%, 98%, 99% and even 100%) sequence identity to SEQ ID NO: 16. In a further embodiment, the invention relates to a host cell transformed with a vector according to the sixth aspect of the invention. In some embodiments, the host cell is a bacterial cell, for example *E. coli*.

In a seventh aspect, the invention relates to a recombinant bacterial culture that produces a composition of fatty alcohols comprising carbon chain lengths of at least 60% of C12, C14 and C16 fatty alcohols, wherein the bacterial culture comprises an engineered bacterial microorganism comprising a gene encoding a heterologous FAR comprising at least 90% (at least 95%, at least 97% and even 100%) sequence identity to SEQ ID NO: 2, SEQ ID NO:4, SEQ ID NO: 6 or SEQ ID NO:8 and a gene encoding a heterologous FabH comprising at least 90% (at least 95%, at least 97% and even 100%) sequence identity to SEQ ID NO: 10. In some embodiments the engineered bacterial microorganism is an *E. coli* strain. In some embodiments the fatty alcohol composition produced by the bacterial culture will comprise at least 80% of C12, C14 and C16 fatty alcohols. In some embodiments the fatty alcohol composition produced by the bacterial culture will comprise at least 60% of the combination of C12 and C14 fatty alcohols. In further embodiments, the fatty alcohol composition produced by the bacterial culture will be recovered from the culture.

BRIEF DESCRIPTION OF THE FIGURES

Figure 3:
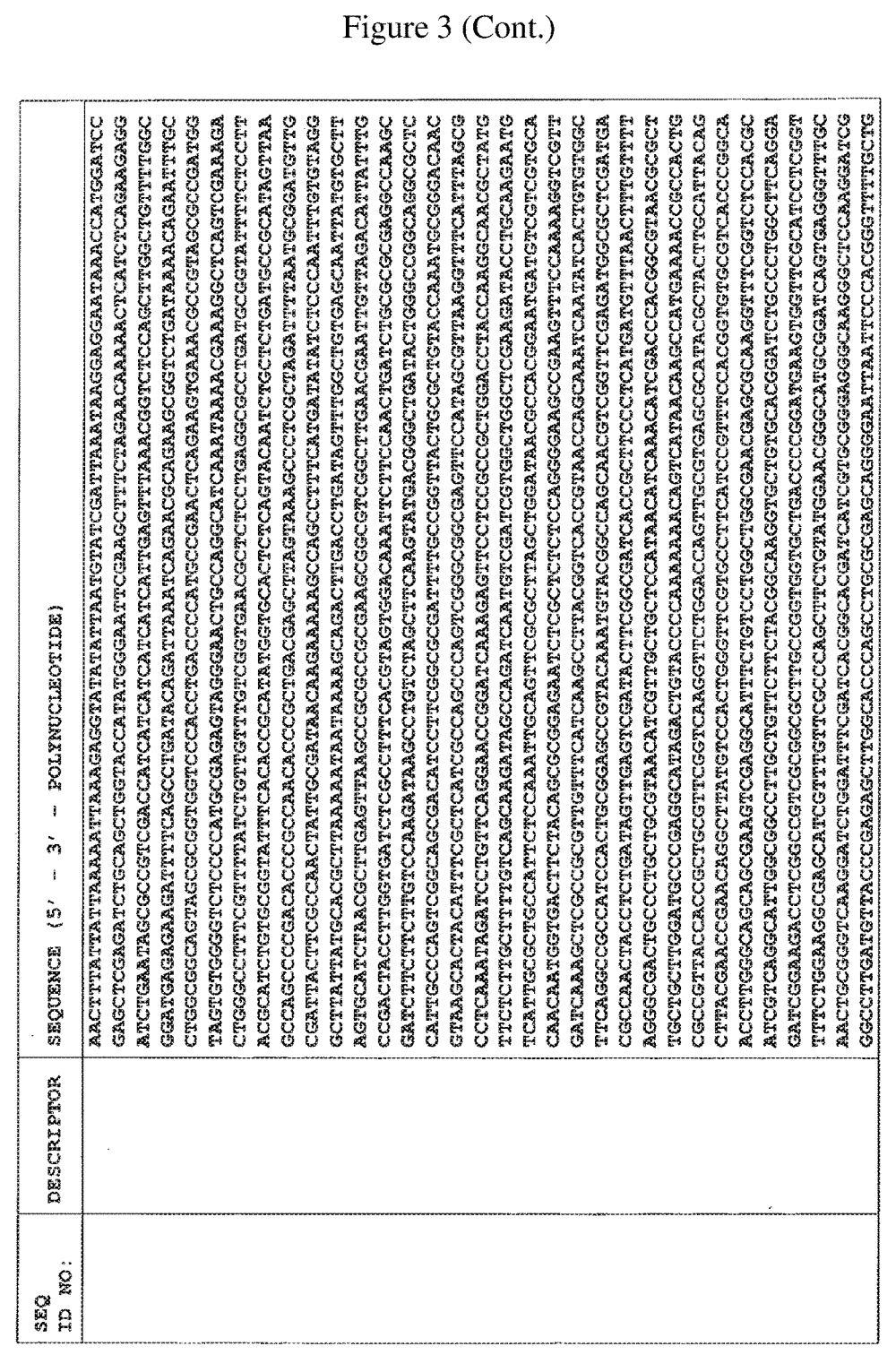

FIG. 3 describes polynucleotide and amino acid sequences encompassed by the invention:

Figure 1:
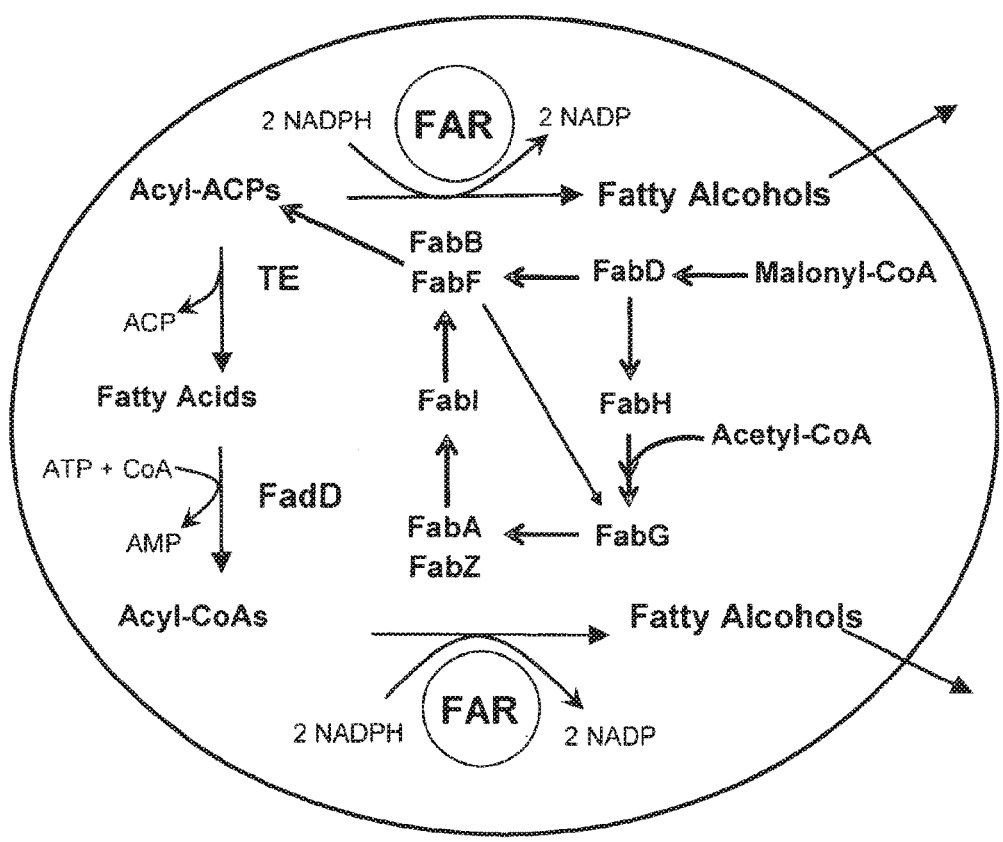
FIG. 1 illustrates a pathway for the production of fatty alcohols in an engineered microbial host cell according to an embodiment of the invention, wherein the fatty alcohols are secreted from the engineered cell.

SEQ ID NO:1 illustrates a codon optimized FAR polynucleotide sequence encoding the wild-type FAR amino acid sequence of SEQ ID NO: 2;

SEQ ID NO:3 illustrates a FAR polynucleotide sequence encoding a variant FAR ("FAR-V1") amino acid sequence of SEQ ID NO:4;

SEQ ID NO:5 illustrates a FAR polynucleotide sequence encoding a variant FAR ("FAR-V2") amino acid sequence of SEQ ID NO:6;

SEQ ID NO:7 illustrates a FAR polynucleotide sequence encoding a variant FAR ("FAR-V3") amino acid sequence of SEQ ID NO:8;

SEQ ID NO:9 illustrates an *E. coli* fabH polynucleotide sequence encoding a β ketoacyl acyl carrier protein synthase III amino acid sequence of SEQ ID NO:10:

SEQ ID NO:11 illustrates a polynucleotide sequence encoding the thioesterase ("TE") amino acid sequence of SEQ ID NO: 12;

SEQ ID NO: 13 illustrates a polynucleotide sequence encoding the FadE amino acid sequence of SEQ ID NO: 14;

SEQ ID NO:15 illustrates a polynucleotide sequence encoding the FadD amino acid sequence of SEQ ID NO: 16;

SEQ ID NO: 17 illustrates a polynucleotide sequence encoding the FabG amino acid sequence of SEQ ID NO: 18;

SEQ ID NO: 19 illustrates a polynucleotide sequence encoding the FabI amino acid sequence of SEQ ID NO:20;

SEQ ID NO: 21 illustrates a polynucleotide sequence encoding the FabZ amino acid sequence of SEQ ID NO: 22;

SEQ ID NO: 23 illustrates a polynucleotide sequence encoding the FadR amino acid sequence of SEQ ID NO: 24;

SEQ ID NO: 25 illustrates a polynucleotide sequence encoding the FabD amino acid sequence of SEQ ID NO: 26;

SEQ ID NO: 27 illustrates a polynucleotide sequence encoding the FabB amino acid sequence of SEQ ID NO: 28;

SEQ ID NO: 29 illustrates a polynucleotide sequence encoding the FabF amino acid sequence of SEQ ID NO: 30;

SEQ ID NO: 59 illustrates the DNA sequence of plasmid pLS8379 and SEQ ID NO: 62 illustrates a polynucleotide sequence encoding a TE polypeptide of SEQ ID NO: 63.

ABBREVIATIONS AND TERMS

Unless defined otherwise herein, all technical and scientific terms used herein have the same meaning as commonly understood by one of ordinary skill in the art to which this invention pertains. Many technical dictionaries are known to those of skill in the art. Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art.

Also, as used herein, the singular "a", "an," and "the" include the plural references, unless the context clearly indicates otherwise. Further, the term "or" is used in the present application to mean the disjunctive "or" and the conjunctive "and".

Amino acids are designated using the three-letter symbols or one-letter symbols recommended by the IUPAC-IUB Biochemical Nomenclature Commission. Unless otherwise indicated, nucleic acids are written left to right in 5' to 3' orientation: amino acid sequences are written left to right in amino to carboxy orientation, respectively. "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

As used herein, the term "comprising" and its cognates are used in their inclusive sense (i.e., equivalent to the term "including" and its corresponding cognates).

The term "fatty alcohol" as used herein refers to an aliphatic alcohol of the formula R—OH, where the R group is at least 4, 5, 6, 7, 8, 9, 10, 11, 12, 13, 14, 15, 16, 17, 18, 19, 20 or more carbons in length. R can be saturated or unsaturated. Further saturated or unsaturated fatty alcohols can be described as "Ca:b-OH", wherein "a" is an integer that represents the total number of carbon atoms in the fatty alcohol and "b" is an integer that refers to the number of double bonds in the carbon chain. In some embodiments, a fatty alcohol produced according to the methods disclosed herein is a C8-C24 saturated or unsaturated fatty alcohol (i.e., a C8, C9, C10, C11, C12, C13, C14, C15, C16, C17, C18, C19, C20, C21, C22, or C24 fatty alcohol). In some embodiments, multiple fatty alcohols are produced with varying saturation levels. For example, in some embodiments, C10, C12, C14, C16 and/or C18 fatty alcohols are produced. In some embodiments, one or more of the following fatty alcohols is produced: 1-decanol (C10:0), 1-dodecanol (C12:0), 1-tetradecanol (C14:0), 1-hexadecanol (C16:0), 1-octadecanol (C18:0).

The term "carbon chain length" as used herein means the number of carbon atoms in a carbon chain of a fatty alcohol or fatty alcohol substrate. For example the term "C12 fatty alcohol" refers to a fatty alcohol molecule having 12 carbons.

The phrase "preference for cleaving a substrate having a certain carbon chain length" or "predominantly cleaving a substrate having a certain carbon chain length" means that an enzyme cleaves or hydrolyzes mainly substrates having a defined number of carbon atoms. The preference is not necessarily exclusive. For example, an enzyme having a preference for cleaving substrates with chain lengths of 12 carbons, may still cleave substrates having chain lengths of 10 or 14 carbon atoms. A more specific non-limiting example includes but is not limited to a TE that predominantly hydrolyzes C12 acyl ACP. The enzyme may still cleave a C10 or C14 ACP substrate.

The term a "fatty alcohol composition" as used herein, means a composition which encompasses at least one fatty alcohol and which is produced from an engineered microbial organism according to the methods of the invention. The fatty alcohol compositions of the invention may include one or more fatty alcohols. For example a fatty alcohol composition may include only C12 fatty alcohols or a fatty alcohol composition may include a combination of C12, C14 and C16 fatty alcohols and these fatty alcohols may be saturated or unsaturated fatty alcohols.

The term "fatty acid" as used herein means a compound having the formula $RCO_2H$, wherein R is at least two carbons in length and generally between 4 and 22 carbons in length. Fatty acids may be saturated or unsaturated and further "R" can be linear or branched.

The term "acyl-ACP as used herein means a compound having the formula RCO-S-ACP, wherein "R" is at least three carbons in length and may be a straight chain or branched chain and saturated or unsaturated. The abbreviation "ACP" refers to an acyl carrier protein.

The terms "fatty acyl-CoA reductase", "fatty acyl reductase", and "fatty acyl acyl-ACP reductase" (EC 1,1.1.*) are used interchangeably herein to refer to an enzyme that catalyzes the reduction of a fatty acyl-CoA, a fatty acyl-ACP, or other fatty acyl thioester complex to a fatty alcohol, in a reaction linked to the oxidation of NAD(P)H to NAD(P)$^+$. The abbreviation "FAR" is used herein to refer to these fatty alcohol forming enzymes. In some embodiments, a FAR enzyme includes functional fragments. In some embodiments, the FAR enzyme is a modified or variant FAR, wherein a wild-type FAR has been genetically modified to include at least 1 (at least 2, 3, 4, 5, 6, 7, 8, 9, 10, 12, 15 or more) amino acid alterations (e.g., substitutions, deletions and/or insertions) as compared to a reference FAR.

The term "acyl-CoA" refers to an acyl thioester formed between the carbonyl carbon of an alkyl chain and the sulfydryl group of the 4'-phosphopantetthionyl moiety of co-enzyme A (CoA) which has the formula R—C(O)—S—CoA, wherein R is an alkyl group having at least 4 carbon atoms and preferably between 10 and 14 carbon atoms. R may be straight or branched and saturated or unsaturated.

The phrase "fatty acid biosynthetic ("Fab") enzymes" as used herein means a complex of enzymes involved in a number of reactions to produce saturated and unsaturated fatty acids. The process is primed by the enzymatic conversion of malonyl-CoA into malonyl-ACP and continues by successive addition of 2 carbons derived from malonyl-ACP residues, providing ACP intermediates (i.e., acyl-ACPs). There are at least 8 enzymes involved fatty acid initiation and elongation biosynthesis including FabA, FabB, FabD, FabF, FabG, FabH, FabI, and FabZ, collectively and individually referred to herein as "fatty acid biosynthetic" enzymes. Furthermore the ACP protein plays a key role in fatty acid biosynthesis by anchoring the nascent acyl chain and making the acyl chain accessible to other enzymes.

The term "FabD" refers to a malonyl-CoA-ACP transferase (EC 2.3.1.39).

The term "FabF" refers to a β-ketoacyl-ACP synthase II (3-oxoacyl-ACP synthetase (EC 2.3.1.41) which catalyzes the conversion of palmitoleate to cis-vaccenate.

The term "FabG" refers to a 3'ketoacyl-ACP-reductase (3-oxoacyl ACP reductase) (EC 1.1.1.100) which catalyzes the NADPH dependent reduction of beta-ketoacyl-ACP substrates to beta-hydroxyacyl-ACP products, the first reductive step in the elongation cycle of fatty acid biosynthesis.

The term "FabI" refers to a trans-2-enoyl-ACP reductase (EC 1.3.1.9 and 1.3.1.10) that catalyzes the reaction of a trans-2,3-dehydroacyl-[ACP]+NAD(P)H+H$^+$ to an acyl-ACP+NAD(P)$^+$.

The term "FabZ" refers to a beta-hydroxyacyl-ACP dehydratase (EC 4.2.1.59 to 4.2.61) that catalyzes the reaction of a (3R)-3-hydroxyacyl-ACP to a trans $\Delta^2$-enoylacylACP+ $H_2O$.

The term "FabB" refers to a beta-ketoacyl-ACP synthase I (EC 2.3.1.41) that catalyzes the chemical reaction of an acyl-ACP to a 3-oxoacyl-ACP.

The term "FadD" refers to an "acyl-CoA synthetase" ("ACS") (EC 6.2.1 (acid-thiol ligases)). In some embodiments, the ACS is classified as EC 6.2.1.3. These ACSs are also known as long chain fatty acid-CoA ligases. An ACS catalyzes the reaction of free fatty acids (both saturated and unsaturated fatty acids) into metabolically active CoA esters (e.g., acyl-CoA) during fatty acid degradation. In some embodiments the FadD may be classified as EC 2.3.1.86 (fatty acyl CoA synthase).

The term "FadK" refers to an acyl-CoA synthetase (ACS) (EC 6.2.1) that catalyzes the reaction of free fatty acids having preferentially C10 or less carbon chain lengths. In some cases the gene (fadK) encoding FadK has also been known as ydiD. Reference is made to Morgan-Kiss R M et al. 2004 J. Biol. Chem., 279:37324-37333.

In some bacterial organisms, (e.g. *E. coli*) both fadD and fadK genes occur and both genes encode enzymes having ACS activity. In some bacterial organisms there may be more than two genes which encode enzymes having ACS activity.

The term "thioesterase or thioester hydrolase (TE)" enzyme used herein means an enzyme having thioesterase activity. TEs are identified as members of EC 3.1.2.1 to EC 3.1.2.27 and also EC 3.1.1.5 and EC 3.1.2.- and these enzyme which hydrolyze the thioester bond between a carbonyl group and a sulfur atom are classified based on enzyme function and substrate identity. In addition, TEs are classified based on the ThYme database (Thioester-active enzyme). In this classification system, TEs have been classified based on amino acid sequence similarity. Under the ThYme system, TEs are further divided into 24 different families (TE1-TE24). Reference is made to D. C. Cantu et al., (2010) Protein Science, 19:1281-1295 and D. C. Cantu et al., (2011) Nucleic Acid Research 39:doi10:1093/nar/gkq1072. TEs according to the invention will have the ability to catalyze a thioester cleavage reaction hydrolyzing a thioester into an acid and a thiol. TEs useful in the invention may be obtained from a number of sources including plant, bacterial, algal, and fungal sources.

The phrase "altered level of expression" means a polynucleotide or polypeptide in a recombinant microorganism encompassed by the invention is present in an amount or concentration that is different (e.g. greater or less) than the amount or concentration when compared to a corresponding reference microorganism.

The term "FabH" refers to 3-oxoacyl-(acyl-carrier protein) synthase III activity and is used interchangeably with "KASIII" and "β-ketoacyl-ACP synthase III". FabH participates in the initial condensation reaction in the fatty acid biosynthetic pathway, by catalyzing the condensation of acetyl-CoA with malonyl-ACP to form aceto-acetyl-ACP and is categorized as EC 2.3.1.180. The FabH enzymes have a His-Asn-Cys catalytic triad at their active site.

The term "FadR" protein as used herein, refers to a multifunctional dual regulator that exerts negative control over the fatty acid degradative regulon and activates expression of fabA and fabF. The FadR regulator is encoded by a fadR gene. A "regulon" comprises a set of genes under control of a single regulatory protein.

The term "FadE" enzyme as used herein means an acyl-CoA dehydrogenase enzyme (EC 1.3.99.-). A FadE gene is also known as yafH.

Throughout the specification a reference may be made using an abbreviated gene name or an enzyme name. For example "fabH" refers to a gene encoding a β-ketoacyl ACP synthase III or as sometimes referred to herein a FabH enzyme.

The term "analogous sequence" or "homologous sequence" as used herein means a sequence wherein the function of the gene is essentially the same as a reference gene. For example, a reference gene may be a fabH gene from E. coli. In some embodiments, the analogous sequence will have at least about 60%, for example, at least about 65%, 70%, 75%, 80%, 85%, 88%, 90%, 91%, 92%, 93%, 94%, 95%, 96%, 97%, 98%, 99% sequence identity with the reference sequence.

The term "wild-type" or "native" as used herein in reference to a polypeptide or protein mean a polypeptide or protein expressed by a naturally occurring microorganism found in nature. When used in reference to a microorganism, the term means a naturally occurring (not genetically modified or engineered) microorganism.

The term "substrate" as used herein refers to a substance or compound that is converted or suitable for conversion into another compound (e.g., a product) by the action of at least one enzyme. The term includes not only a single compound but also combinations comprising more than one compound.

The term "conversion" as used herein refers to the enzymatic transformation of a substrate to at least one corresponding product. "Percent conversion" refers to the percent of the substrate that is converted to the product(s) within a specified period of time and under specified conditions.

Nucleic acid sequences may be "introduced" into a cell by protoplast fusion, transfection, transduction, transformation, electroporation or any other suitable method known in the art. A nucleic acid sequence introduced into a prokaryotic cell may be integrated into a chromosome or may be maintained as an episome.

The terms "transformed" and "stably transformed" as used herein refer to a cell that has a non-native (i.e., heterologous) polynucleotide sequence integrated into its genome or as an episomal plasmid that is maintained for at least two generations.

The term "gene" as used herein refers to a polynucleotide (e.g., a DNA segment), that encodes a polypeptide and includes regions preceding and following the coding regions as well as intervening sequences (introns) between individual coding segments (exons).

The terms "endogenous" when used in reference to a gene refers to a gene that is found in a parental strain of a cell (e.g., a bacterial cell). As used herein in making comparisons between endogenous nucleic acid sequences, "homologous genes" (or "homologue" genes) refers to genes from different, but usually related species, which correspond to each other and are identical or very similar to each other. The term encompasses genes that are separated by speciation (i.e., the development of new species) (e.g., orthologous genes), as well as genes that have been separated by genetic duplication (e.g., paralogous genes).

The term "heterologous" polynucleotide as used herein means any polynucleotide that is introduced into a host cell by laboratory techniques, and includes polynucleotides that are removed from a host cell, subjected to laboratory manipulation, and then reintroduced into a host cell.

In some embodiments, when "heterologous" is used with reference to a nucleic acid or polypeptide, the term refers to a sequence that is not normally expressed and secreted by an organism (e.g., a "wild-type" organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

As used herein, a "heterologous enzyme" is used in reference to an enzyme that is encoded by a heterologous gene. However, it is also contemplated herein that a heterologous gene can encode an endogenous or homologous enzyme. As used herein, the term "heterologous gene" refers to a gene that occurs in a form not found in a parental strain of the host cell. Thus, in some embodiments, a heterologous gene is a gene that is derived from a species that is different from the species of the host cell expressing the gene. In some embodiments, a heterologous gene is a modified version of a gene that is endogenous to the host cell (e.g., an endogenous gene subjected to manipulation and then introduced or transformed into the host cell). For example, in some embodiments, a heterologous gene has an endogenous coding sequence, but has modifications in the promoter sequence. Similarly, in other embodiments, a heterologous gene encodes the same amino acid sequence as an endogenous gene, but has modifications in codon usage and/or to noncoding regions (e.g., introns), and/or combinations thereof. In some embodiments, the heterologous gene is a gene that has been modified to overexpress a gene product of interest.

The term "expression" as used herein includes any step involved in the production of a polypeptide including, but not limited to, transcription, post-transcriptional modification, translation, post-translational modification, and secretion.

The term "overexpression" as used herein refers to any state in which a gene is caused to be expressed at an elevated rate or level as compared to the endogenous expression rate or level for that gene. In some embodiments, "overexpression" includes an elevated translation rate or level of the gene compared to the endogenous translation rate or level for that gene. In some embodiments, overexpression includes an elevated transcription rate or level of the gene compared to the endogenous transcription rate or level for that gene. It is intended that the term encompass overexpression of endogenous, as well as heterologous proteins.

The term "recombinant" as used herein includes reference to a cell or vector, that has been modified by the introduction of a heterologous nucleic acid sequence or that the cell is derived from a cell so modified. Thus, for example, recombinant cells express genes that are not found in identical form within the native (i.e. non-recombinant) form of the cell or express native genes that are otherwise abnormally expressed, under-expressed or not expressed at all as a result of deliberate human intervention. "Recombinant," "engineered," and "non-naturally occurring," when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (i.e. non-recombinant) form of the cell or express native genes that are otherwise expressed at a different level.

The term "plasmid" as used herein refers to a circular double-stranded (ds) DNA construct used as a cloning vector, and which forms an extrachromosomal self-replicating genetic element in some eukaryotes or prokaryotes, or integrates into the host chromosome.

The term "operably linked" as used herein refers to a configuration in which a control sequence is appropriately placed (i.e., in a functional relationship) at a position relative to a polynucleotide of interest such that the control sequence directs or regulates the expression of the polynucleotide and/or polypeptide of interest. Thus, a nucleic acid is "operably linked" to another nucleic acid sequence when it is placed into a functional relationship with another nucleic acid sequence.

The term "control sequence" as used herein includes all components, which are necessary and/or advantageous for the expression of a polynucleotide of the present disclosure. Each control sequence may be native or foreign to the polynucleotide of interest. Such control sequences include, but are not limited to, leaders, polyadenylation sequences, propeptide sequences, promoters, signal peptide sequences, and transcription terminators.

The terms "modified host cell", "engineered host cell" or "recombinant host cell" as used interchangeably herein refer to a cell whose genetic material has been altered using genetic engineering techniques. An engineered cell also refers to a derivative of or the progeny of a cell whose genetic material has been altered using genetic engineering techniques. An example of a genetic modification as a result of genetic engineering techniques includes a modification to the genomic DNA. Another example of a genetic modification as a result of genetic engineering techniques includes introduction of a stable heterologous nucleic acid into the cell.

The phrase "a corresponding engineered cell grown under essentially the same culture conditions" as used herein means a reference host cell (either engineered or native) which is grown under essentially the same culture conditions, including but not limited to pH, temperature, time, and culture media as compared to an engineered cell encompassed by the invention and to which the reference cell is being compared.

The term "carbon source" as used herein refers to a substrate that is suitable for use as a source of carbon for cell growth.

Nucleic acids "hybridize" when they associate, typically in solution. There are numerous texts and other reference materials that provide details regarding hybridization methods for nucleic acids (See e.g., Tijssen, LABORATORY TECHNIQUES IN BIOCHEMISTRY AND MOLECULAR BIOLOGY—HYBRIDIZATION WITH NUCLEIC ACID PROBES," Part 1, Chapter 2, Elsevier, New York, [1993], incorporated herein by reference). For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. ("low" stringency), at least at 55° C. ("medium" or "moderate" stringency), at least at 60° C. ("medium-high" stringency), at least at 65° C. ("high" stringency), and at least at 70° C. ("very high" stringency). In some embodiments, the stringency conditions include those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. In other embodiments, the stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors to accomplish the desired stringency.

The phrase "naturally-occurring enzyme" as used herein refers to an enzyme having the unmodified amino acid sequence identical to that found in nature (i.e., "wild-type"). Naturally occurring enzymes include native enzymes (i.e., those enzymes naturally expressed or found in the particular microorganism).

The term "variant" or "mutant" as used interchangeably herein refer to a polypeptide sequence or polynucleotide sequence encoding a polypeptide, said sequence comprising one or more modifications relative to a corresponding wild-type enzyme (or other specified reference sequence) or the wild-type polynucleotide (or other specified reference sequence) such as substitutions, insertions, deletions, and/or truncations of one or more specific amino acid residues or of one or more specific nucleotides or codons in the polypeptide or polynucleotide. In some embodiments, reference to a variant at an amino acid residue refers to a substitution of the amino acid residue for another amino acid residue. Mutagenesis and directed evolution methods are well known in the art for creating variants. See, e.g., U.S. Pat. No. 7,783,428; U.S. Pat. No. 6,429,175; U.S. Pat. No. 6,376,246; U.S. Pat. No. 6,586,182; U.S. Pat. No. 6,117,679; and Ling, et al., 1999, "Approaches to DNA mutagenesis: an overview," *Anal. Biochem.*, 254(2):157-78; Smith, 1985. "In vitro mutagenesis," *Ann. Rev. Genet.*, 19:423-462; Carter, 1986. "Site-directed mutagenesis," *Biochem. J.*, 237:1-7; Minshull, et al., 1999, "Protein evolution by molecular breeding," *Current Opinion in Chemical Biology*, 3:284-290;

The terms "isolated" or "recovered" as used herein refer to a material that is removed from its original environment (e.g., the natural environment, if it is naturally occurring). For example, the material is said to be "isolated" when it is present in a particular composition in a higher or lower concentration than exists in a naturally-occurring or wild-type organism or in combination with components not normally present upon expression from a naturally-occurring or wild-type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still considered to be isolated, in that such vector or composition is not part of its natural environment. In some embodiments, the term isolated refers to fatty alcohol compounds of varying chain lengths which are isolated or recovered from an engineered cell according to the invention.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, the term "biologically active fragment," or "functional fragment" refers to a polypeptide that has an amino-terminal and/or carboxy-terminal deletion(s) and/or internal deletion(s), but where the remaining amino acid sequence is identical to the corresponding positions in the sequence to which it is being compared (e.g., a full-length FAR of the present invention) and that retains substantially all of the activity of the full-length polypeptide. For example, a biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length FAR polypeptide.

The term "attenuated" or "inactivated" used interchangeably herein, as applied to a gene refers to any genetic modification that decreases or eliminates the expression of the gene and/or the functional activity of the corresponding gene product (mRNA and/or protein). The term encompasses complete or partial inactivation, suppression, deletion, interruption, blockage, promoter alterations, antisense RNA, dsRNA, or down-regulation of a gene. This can be accomplished, for example, by gene "knockout," inactivation, mutation (e.g., insertion, deletion, point, or frameshift mutations that disrupt the expression or activity of the gene product), or by use of inhibitory RNAs (e.g., sense, anti-sense, or RNAi technology). A deletion may encompass all or part of a gene's coding sequence. The term "knockout" refers to the deletion of most (at least about 95%, at least about 96%, at least about 97%, at least about 98%, or at least about 99%) or all (100%) of the coding sequence of a gene. In some embodiments, any number of nucleotides can be deleted, from a single base to an entire piece of a chromosome.

With respect to "homologs," reference to particular gene names is for illustration and not limitation. It is understood that gene names vary from organism to organism and reference to a gene name is not intended to be limiting, but is intended to encompass homologs and polymorphic variants with equivalent activity. In certain embodiments, the invention includes a polynucleotide or polypeptide sequence with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% identity with the named gene or gene product.

The terms "peptide," "polypeptide." and "protein" are used interchangeably herein to refer to a polymer of amino acid residues. In various aspects of the invention, the availability of a polypeptide sequence of a specific enzyme provides a description of all polynucleotides capable of encoding the polypeptide of known sequence because of the known correspondence of particular codons and the amino acids they encode. In certain embodiments, the degeneracy of the genetic code is used to produce a large number of polynucleotides that encode a polypeptide described herein.

"Identity" or "percent identity" in the context of two or more polypeptide sequences or two or more polynucleotide sequences refers to two or more sequences or sub-sequences that are the same or have a specified percentage of amino acid residues or nucleotide residues that are the same. For example, the sequence can have a percent identity of at least about 50%, about 60%, about 70%, about 75%, about 80%, about 85%, about 90%, about 91%, about 92%, about 93%, about 94%, about 95%, about 96%, about 97%, about 98%, or about 99% over a specified region to a reference sequence when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al. infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a variant FAR has sequence identity to SEQ ID NO:2 is the BLAST algorithm, which is described in Altschul et al., 1990, *J. Mol. Biol.* 215:403-410, which is incorporated herein by reference. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1997. Nucleic Acids Res., 25:3389-3402). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues: always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915). Other programs that may be used include the Needleman-Wunsch procedure, J. Mol. Biol. 48: 443-453 (1970), using blosum62, a Gap start penalty of 7 and gap extend penalty of 1; and gapped BLAST 2.0 (see Altschul, et al. 1997, Nucleic Acids Res., 25:3389-3402) both available to the public at the National Center for Biotechnology Information Website.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation. Version 8.01, July 2009, Worldwide Web .tcoffee.org), or Protein Align. In Protein Align, alignments are computed by optimizing a function based on residue similarity scores (obtained from applying an amino acid substitution matrix to pairs of aligned residues) and gap penalties. Penalties are imposed for introducing any extending gaps in one sequence with respect to another. The final optimized function value is referred to as the alignment score. When aligning multiple sequences, Protein Align optimizes the "sum of pairs" score, i.e., the sum of all the separate pairwise alignment scores.

As used herein, the term "culturing" refers to growing a population of microbial cells under suitable conditions using any suitable medium (e.g., liquid, solid, or semi-solid media).

The term "extracellular environment" means the aqueous solution surrounding a cell membrane, excluding the intracellular space. For example, a secreted enzyme or a compound is found in the extracellular environment. In some embodiments, the extracellular environment comprises the culture medium used to grow the cell.

The term "contacting" refers to combining an enzyme and a substrate under conditions in which the enzyme can act on the substrate. Those skilled in the art will recognize that mixing a solution containing an enzyme with a substrate will effect "contacting." Similarly, in the context of culturing microorganisms, culturing microorganisms in a media containing a substrate (e.g., a fermentable sugar) will effect "contacting" the microorganism with the substrate.

The term fermentable sugars" refers to simple sugars (monosaccharides, disaccharides and short oligosaccharides) such as but not limited to glucose, xylose, galactose, arabinose, mannose and sucrose. Fermentable sugar is any sugar that a microorganism can utilize for growth or which can be used in the production of end-products such as but not limited to ethanol, hydrocarbon, amino acids and other chemical compounds.

The terms "cleaning compositions" and "cleaning formulations" refer to compositions that find use in the removal of undesired compounds from items to be cleaning, such as fabric, dishes, contact lenses, other solid substrates, hair (shampoos), skin (soaps and creams), teeth (mouthwashes, toothpastes, etc.), etc. The terms further refer to any composition that is suited for cleaning, bleaching, disinfecting and/or sterilizing any object and/or surface. It is intended that the terms include, but are not limited to detergent compositions (e.g., laundry and fine fabric detergents), hard surface cleaning formulations (e.g. for glass, wood, ceramics and metal countertops, windows, etc.), oven cleaners, carpet cleaners, fabric fresheners, fabric softeners, hand and machine dish detergents, dish rinse aids, and textile and laundry pre-spotters. In addition, the terms encompass cleaning compositions for use in household and institutional use, including but not limited to liquid cleaning and disinfecting agents, such as anti-bacterial hand soaps and wipes, cleaning bars, mouthwashes, denture cleaners, car shampoos, bathroom cleaners, hair shampoos and conditioners/rinses for humans and other animals, shower gels, foam baths, etc. Indeed, it is not intended that the term be limited to any particular cleaning composition. The terms encompass any materials/compounds selected for the particular type of cleaning compositions desired and the form of the product (e.g., liquid, gel, granule, or spray), as long as the composition is compatible with the fatty alcohol(s) of the present invention. The specific selection of cleaning composition materials are readily made by considering the surface, item or fabric to be cleaned, and the desired form of the composition for the cleaning conditions during use.

DETAILED DESCRIPTION OF THE INVENTION

1. FAR Enzymes and Polynucleotides:

The engineered prokaryotic cells encompassed by the invention are modified to express a polynucleotide encoding a heterologous FAR. Polynucleotides encoding FAR enzymes are known in the art (See e.g., WO2011/008535; WO2011/019858; WO2012/006114; US2010/02036; U.S. Pat. No. 7,332,311; U.S. Pat. No. 6,143,538 and Metz et al. 2000. Plant Physiol. 122:635-644).

In some embodiments, FAR substrates, (e.g., acyl-CoA) are reduced to a fatty alcohol in a two-step process. An NAD(P)H dependent acyl-CoA reductase converts an acyl-CoA to a fatty aldehyde and then the fatty aldehyde is reduced to a fatty alcohol by a NAD(P)H dependent alcohol dehydrogenase. Enzymes involved in this two-step conversion include the enzymes Acr1 and YqhD (See, Reiser and Somerville, J. Bacteriol. (1997) 179:2969; Ishige et al., Appl. Environ. Microbiol. (2000) 66:3481; Hofrander et al. (2011) FEBS Letters 585:3538-3543 and Kalscheuer et al., 2006, Appl. Environ. Microbiol. 72:1373).

Preferred fatty alcohol forming acyl-CoA reductases (FARs) useful in the present invention catalyze the direct reduction of acyl-CoA and/or acyl-ACP substrates to fatty alcohols wherein free fatty aldehydes are essentially not released as an intermediate. Essentially these FARs reduce acyl chains to fatty alcohols by one enzymatic step. Depending on the substrate chain length it is possible to have trace amounts of aldehydes produced and released. In this direct reduction process, FAR converts at least acyl-ACP substrates to a fatty alcohol end-product without the subsequent action of an alcohol dehydrogenase.

In some embodiments, the FAR is a prokaryotic enzyme. In some embodiments, the FAR is derived from a species of *Marinobacter* including, but not limited to *M. algicola*, *M. alkaliphilus*, *M. aquaeolei*, *M. arcticus*, *M. bryozoorum*, *M. daepoensis*, *M. excellens*, *M. flavimaris*, *M. guadonensis*. *M. hydrocarbonoclasticus*, *M. koreenis*, *M. lipolyticus*, *M. litoralis*, *M. lutaoensis*, *M. maritimus*, *M. sediminum*, *M. squalenivirans*, and *M. vinifirmus*, and equivalent and synonymous species thereof.

In certain embodiments, the FAR is derived from *M. algicola* strain DG893 and has an amino acid sequence that is at least about 70% identical, at least about 75%, at least about 80% identical, at least about 85% identical, at least about 90% identical, at least about 93% identical at least about 95% identical, at least about 97% identical, at least about 98% identical and/or at least about 99% identical to SEQ ID NO:2 and/or a functional fragment thereof. In another embodiment, the FAR enzyme has an amino acid sequence that is identical to SEQ ID NO:2. In certain embodiments, the FAR is a variant of the wild-type FAR of SEQ ID NO:2 for example a FAR having at least 90%, (91%, 92%, 93%, 94%, 95%, 96%, 97%, 98%, 99% and even 100% sequence identity to SEQ ID NO: 4, SEQ ID NO: 6 or SEQ ID NO: 8. In some embodiments, the variant FAR is FAR-V1 comprising an amino acid sequence of SEQ ID NO: 4; in other embodiments the variant FAR is FAR-V2 comprising the amino acids sequence of SEQ ID NO: 6; and in other embodiments the variant FAR is FAR-V3 comprising the amino acid sequence of SEQ ID NO: 8. In some embodiments, the FAR variant comprises at least 95%, (at least 96%, 97%, 98%, and 99%) amino acid sequence identity to SEQ ID NO: 8. In some embodiments, the FAR variants will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:4, SEQ ID NO: 6 or SEQ ID NO: 8.

In certain embodiments, the FAR is derived from *Marinobacter aquaeolei* and has an amino acid sequence that is at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ID NO: 5 as disclosed in WO 2012/006114 and/or a functional fragment thereof. In another specific embodiment, the FAR enzyme has an amino acid sequence that is identical to SEQ ID NO: 5. In certain embodiments, the FAR is a variant of the wild-type FAR of SEQ ID NO:5 that has at least 1, at least 2, at least 3, at least 4, at least 5, at least 6, at least 7, at least 8, at least 9, at least 10, at least 12, at least 14, at least 16, at least 18, at least 20, or more amino acid alterations (e.g., substitutions, deletions and/or insertions) relative to SEQ ID NO:5. In certain embodiments, the FAR is encoded by a polynucleotide sequence having at least 85% (at least 90%, 91%, 92%, 93%, 94%, 95%, 96%, 97%, 98%, 99% sequence identity to SEQ ID NO:4 as disclosed in WO 2012/006114.

In certain embodiments, the FAR is obtained from a marine bacterium selected from the group of *Meptuniibacter caesariensis* strain MED92. *Reinekea* sp. strain MED297, *Marinomonas* sp. strain MED121, unnamed gammaproteobacterium strain HTCC2207, and *Marinobacter* sp. strain ELB17, as well as equivalents and synonymous species thereof. In certain embodiments, the FAR is obtained from the genus *Oceanobacter*. In some embodiments, the FAR is obtained from the *Oceanobacter* species strain RED65 (e.g. NCBI accession number ZP_01305629) and has an amino acid sequence that is at least about 70% identical, at least about 75% identical, at least about 80% identical, at least about 85% identical, at least about 90% identical, at least about 93% identical, at least about 95% identical, at least about 97% identical, at least about 98% identical and/or at least about 99% identical to SEQ ID NOs:6 and/or 8 as disclosed in WO 2011/008535.

In various embodiments, the FAR is encoded by a polynucleotide selected from the group of FAR_Hch (*Hahella chejuensis* KCTC 2396 GenBank YP_436183); FAR_Mac (from marine *Actinobacterium* strain PHSC20C1); FAR_JVC (JCVI_ORF_1096697648832, GenBank Accession No. EDD40059.1); FAR_Fer (JCVI_S-CAF_1101670217388); FAR_Key (JCVI_S-CAF_1097205236585); FAR_Gal (JCVI_S-CAF_1101670289386); *Vitis vinifera* FAR (GenBank Accession No. CAO22305.1 or CAO67776.1); *Desulfatibacillum alkenivorans* FAR (GenBank Accession No. NZ_ABII01000018.1); *Stigmatella aurantiaca* FAR (NZ_AAMD01000005.1); *Phytophthora ramorum* FAR (GenBank Accession No.: AAQX01001105.1); GenBank Accession no. AAD38039.1; gi|5020215|gb|AAD38039.1|AF149917_1 acyl CoA reductase [*Simmondsia chinensis*]; GenBank Accession no. BAC79425.1; gi|331463071|dbj|BAC79425.1| fatty-acyl reductase [*Bombyx mori*]; GenBank Accession no. DQ446732.1 or NM_115529.1; gi|91806527|gb|DQ446732.1| *Arabidopsis thaliana* clone pENTR221-At3g44560; gi|18410556|ref|NM_115529.1|; and (GenBank Accession no. EU817405.1; gi|210063138|gb|EU817405.1| *Ostrinia scapulalis*.

As indicated herein, "heterologous FAR" encompasses wild-type FARs, variants and functional fragments thereof. In various embodiments, a functional fragment of a full-length wild-type FAR or a variant FAR comprises at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises about at least 75%, about at least 80%, about at least 85%, about at least 90%, about at least 91%, about at least 92%, about at least 93%, about at least 94%, about at least 95%, about at least 96%, about at least 97%, about at least 98%, or about at least 99% of the amino acid sequence of a full-length FAR polypeptide.

In another aspect, the present invention provides polynucleotides encoding FAR enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FAR polypeptide encompassed by the invention is coded for by a polynucleotide sequence that has been codon optimized. In particular embodiments, the polynucleotides that encode the FAR enzymes described herein are codon-optimized for expression in a host bacterial cell. Indeed, it is intended that the polynucleotides of the present invention be produced using any suitable methods and components as known in the art.

In some embodiments, a FAR enzyme is encoded by a polynucleotide sequence that has at least about 70%, at least about 75%, at least about 80%, at least about 85%, at least about 90%, at least about 93%, at least about 95%, at least about 96%, at least about 97%, or at least about 99% sequence identity to SEQ ID NO:1, SEQ ID NO:3, SEQ ID NO:5 and/or SEQ ID NO:7 and further hybridizes with SEQ ID NO:1. SEQ ID NO:3, SEQ ID NO: 5 and/or SEQ ID NO:7 under medium, medium-high, high or very high stringency conditions.

In some embodiments, the preferred substrates for the heterologous FAR are fatty acyl-ACP substrates comprising carbon chain lengths of C10 to C18. In certain embodiments, the fatty acyl-ACP substrates comprise carbon chain lengths of C12 to C16, and in other embodiments, the fatty acyl-ACP substrates comprise carbon chain lengths of C12 to C14. In certain embodiments, the substrate comprises a majority of saturated hydrocarbons. In certain embodiments, the substrate pool for the heterologous FAR comprises over about 70% (e.g., about 75%, 80%, 85%, 88%, 90%, 92%, 94%, 95%, 96%, 97%, 98%, and 99%) C10 to C18 fatty acyl-ACP substrates; over about 70% (e.g., about 75%, 80%, 85%, 88%, 90%, 92%, 94%, 95%, 96%, 97%, 98%, and 99%) C10 to C16 fatty acyl-ACP substrates; over about 70% (e.g., about 75%, 80%, 85%, 88%, 90%, 92%, 94%, 95%, 96%, 97%, 98%, and 99%) C12 to C16 fatty acyl-ACP substrates and also over about 70% (e.g., about 75%, 80%, 85%, 88%, 90%, 92%, 94%, 95%, 96%, 97%, 98%, and 99%) C12 to C14 fatty acyl-ACP substrates. In certain embodiments, the substrate pool for the heterologous FAR comprises over about 70% (e.g., about 75%, 80%, 85%, 88%, 90%, 92%, 94%, 95%, 96%, 97%, 98%, and 99%) C10 to C18 fatty acyl-CoA substrates; over about 70% (e.g., about 75%, 80%, 85%, 88%, 90%, 92%, 94%, 95%, 96%, 97%, 98%, and 99%) C10 to C16 fatty acyl-CoA substrates; over about 70% (e.g., about 75%, 80%, 85%, 88%, 90%, 92%, 94%, 95%, 96%, 97%, 98%, and 99%) C12 to C16 fatty acyl-CoA substrates and also over about 70% (e.g., about 75%, 80%, 85%, 88%, 90%, 92%, 94%, 95%, 96%, 97%, 98%, and 99%) C12 to C14 fatty acyl-CoA substrates.

2. FabH Enzymes and Polynucleotides:

The engineered prokaryotic cells encompassed by the invention are additionally modified to express a recombinant polynucleotide encoding a FabH. Polynucleotides encoding FabH enzymes are known in the art (See e.g., Tsay et al., 1992, J. Biol. Chem. 267: 6807-6814).

In some embodiments, the FabH is derived from a bacterial species and in some preferred embodiments the FabH is derived from an *E. coli* strain. In some embodiments, a FabH enzyme coded for by a recombinant polynucleotide comprises an amino acid sequence that is at least about 70% identical, at least about 75% identical, at least about 80% identical, at least about 85% identical, at least about 90% identical, at least about 93% identical, at least about 95% identical, at least about 97% identical, at least about 98% identical and/or at least about 99% identical to SEQ ID NO: 10 and/or a functional fragment thereof. In another embodiment, the FabH enzyme has an amino acid sequence that is identical to SEQ ID NO: 10. In certain embodiments, the FabH is a variant of the wild-type FabH of SEQ ID NO:10 for example a FabH having at least 90%, (91%, 92%, 93%, 94%, 95%, 96%, 97%, 98% and 99%) sequence identity to SEQ ID NO: 10. In some embodiments, the variant FabH will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO: 10.

Homologous fabH genes and polypeptides are known in the art; for example fabH may be derived from *E. coli* strains (see, Tsay et al., J. Biol. Chem. (1992) 267:6807-6814; *Mycobacterium* strains (see. Scarsdale et al., J. Biol. Chem. (2001) 276:20516-20522; and Choi et al., J. Biol. Chem. (2000) 275:28201-28207)), *Staphylococcus* strain (Qiu et al., (2005) Protein Sci. 14:2087-2094); *Streptococcus* strains (Khandekar et al., J. Biol. Chem. (2001) 276:30024-30030); and *Haemophilus* strains (Ketan et al., FEB Letters 583: 2939-2946). In some cases, the FabH enzyme uses acetyl-CoA as the primer and synthesizes straight chain fatty acids, and in other cases the FabH enzyme uses branched chain acyl-CoA as primers. Additional KAS-III polypeptides can be identified by searching the following databases which are available on the world wide web: KEGG database; Entrez databases (NCBI); ExPASy (Swiss Institute of Bioinformatics); and the BRENDA database.

The KASIII from the bacterium *Shigella flexneri* (CDC796-83] has 99% sequence identity to the FabH amino acid sequence of SEQ ID NO: 10. The KASIII from *Yersinia aldovae* (ATCC 35236; ref gb|EEP95833.1) has 80% amino acid sequence identity to SEQ ID NO: 10. Other non-limiting examples of FabHs are listed in Table 1 below.

TABLE 1

| Strain | % Amino Acid Identity | NCBI Protein Accession Number | Reference |
| --- | --- | --- | --- |
| *Salmonella typhimurium* LT2 | 95 | NP_460163.1 | J. Biol. Chem., August 2001, p. 30024-30030 |
| *Streptococcus pneumonia* | 39 | EGJ18508.1 | J. Biol. Chem., August 2001, p. 30024-30030 |
| *Cronobacter sakazakii.* | 89 | E899 | J. Bacteriol. (2011) 193: 5861 |
| *Klebsiella oxytoca* KCTC 1686 | 90 | 1006551 | J. Bacteriol. (2012) 194: 2371-2372 |
| *Erwinia amylovora* CFBP1430 | 81 | 665029 | Mol. Plant Microbe Interact. (2010) 23: 384-393 |
| *Salmonella enterica* subsp. *enterica* serovar | 95 | 1132507 | J. Bacteriol. (2012) 194: 2115-2116 |
| *Citrobacter* sp. 30_2 | 94 | 469595 | |
| *Escherichia albertii* TW07627 | 96 | 502347 | |
| *Lactococcus lactis* I11403 | 38 | AAK04869.1 | J. Biol. Chem., December 2003, p. 51494-51503 |
| *Brenneria* sp. EniD312 | 82 | 598467 | |

FabH activity can be assayed in a number of well-known ways. FabH expression may be characterized based on its effect on the phenotypic output, wherein cells with and without expressed fabH are compared and the phenotypic output is a fatty alcohol chain length profile. Since FabH expression may be the only variable changed, it can be inferred that changes in the fatty alcohol profile are caused by FabH expression. Additionally, cells expressing exogenous FabH can be assayed directly for changes in KAS III activity by assaying for acetoacetyl-ACP synthase activity (via the in vitro conversion of malonyl-ACP and acetyl-CoA into aceto-acetyl-CoA) as described by Tsay et al. (J Biol. Chem. 1992:267:6807-14.) Further examples of methods that can be used to measure KAS activity include a complementation growth assay where a native FabH is compromised (See, Morgan-Kiss and Cronan, 2008 Arch. Microbiol., 427-459) and filtered disc assays such as that described in Choi et al., (2000) J. Bacteriol. 182:365-370.

As indicated herein, "heterologous FabH" encompasses wild-type FabHs, variants and functional fragments thereof. In various embodiments, a functional fragment of a full-length wild-type FabH or a variant FabH comprises at least about 70%, at least about 75%, at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the amino acid sequence of a full-length FabH polypeptide.

In some embodiments, the FabH is a variant of a native FabH. In some embodiments, the native FabH has been engineered such that the substrate specificity has been altered (Nomura et al., Appl. Environ. Microbiol., (2004) 70(2):999-1007).

In another aspect, the present invention provides polynucleotides encoding FabH enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FabH polypeptide encompassed by the invention is coded for by a polynucleotide sequence that has been codon optimized. In particular embodiments, the polynucleotides that encode the FabH enzymes described herein are codon-optimized for expression in a host *E. coli* cell. Indeed, it is intended that the polynucleotides of the present invention be produced using any suitable methods and components as known in the art.

In some embodiments, a FabH enzyme is encoded by a polynucleotide sequence that has at least about 70%, at least about 75%, at least about 80%, at least about 85%, at least about 90%, at least about 93%, at least about 95%, at least about 96%, at least about 97%, or at least about 99% sequence identity to SEQ ID NO: 9 and further hybridizes with SEQ ID NO:9 under medium, medium-high, high or very high stringency conditions. In some embodiments, the nucleic acid coding for the FAR and FabH enzymes as described herein are co-expressed on the same vector and are operably linked to a promoter, and optionally, to other control sequences 3. Other Fab Enzymes and Polynucleotides:

The engineered prokaryotic cells encompassed by the invention are additionally modified to express one or more introduced polynucleotides encoding a FabD, FabG, FabI, FabB and/or FabZ enzyme. Polynucleotides encoding these fatty acid biosynthetic (Fab) enzymes are known in the art (See e.g., Magnuson et al, 1993 Mol. Microbiol. 522-542; Wang and Cronan. 2004 JBC 34489-34495).

In some embodiments, the Fab enzyme is derived from a bacterial species and in some preferred embodiments the Fab enzymes are derived from an *E. coli* strain.

In some embodiments, a FabD enzyme coded for by a polynucleotide comprises an amino acid sequence that is at least about 80% identical, at least about 85% identical, at least about 90% identical, at least about 93% identical, at least about 95% identical, at least about 97% identical, at least about 98% identical and/or at least about 99% identical to SEQ ID NO:26 and/or a functional fragment thereof. In another embodiment, the FabD enzyme has an amino acid sequence that is identical to SEQ ID NO:26. In certain embodiments, the FabD is a variant of the wild-type FabD of SEQ ID NO:26 for example a FabD having at least 90%, (91%, 92%, 93%, 94%, 95%, 96%, 97%, 98%, and 99%) sequence identity to SEQ ID NO: 26. In some embodiments, the variant FabD will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:26.

FabD homologs are known in the art; for example FabD may be derived from *E. coli* strains (see, Magnuson et al., 1992 FEBS Letters 16:299 (3): 262-266). FabD is a highly conserved gene and homologs can be found in plants (e.g., *Arabidopsis thaliana*, AT2G30200); mammals (e.g., *Canis familiaris* ENSCAFP00000001310); yeast (e.g., *Schizosaccharomyces pombe* SPAC11G75c); and other bacteria (e.g., *Shigella flexneri*).

FabD activity can be assayed in a number of well-known ways. For example. FabD activity can be determined through complementation assays or by a conversion of malonyl CoA to malonyl-ACP as described in Magnuson et al., 1992 FEBS Letters 16:299(3):262-6.

As indicated herein, "heterologous FabD" encompasses wild-type FabDs, variants and functional fragments thereof. In various embodiments, a functional fragment of a full-length wild-type FabD or a variant FabD comprises at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises at least about 80%, at least about 85%, at least about 90%, at least about 91%, at least about 92%, at least about 93%, at least about 94%, at least about 95%, at least about 96%, at least about 97%, at least about 98%, or at least about 99% of the amino acid sequence of a full-length FabD polypeptide.

In another aspect, the present invention provides polynucleotides encoding FabD enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FabD polypeptide encompassed by the invention is coded for by a polynucleotide sequence that has been codon optimized. In particular embodiments, the polynucleotides that encode the FabD enzymes described herein are codon-optimized for expression in a host *E. coli* cell. Indeed, it is intended that the polynucleotides of the present invention be produced using any suitable methods and components as known in the art.

In some embodiments, a FabD enzyme is encoded by a polynucleotide sequence that has at least about 75%, at least about 80%, at least about 85%, at least about 90%, at least about 93%, at least about 95%, at least about 96%, at least about 97%, or at least about 99% sequence identity to SEQ ID NO: 25 and further hybridizes with SEQ ID NO:25 under medium, medium-high, high or very high stringency conditions.

In some embodiments, a FabG enzyme coded for by a recombinant polynucleotide comprises an amino acid sequence that is at least about 80% identical, at least about 85% identical, at least about 90% identical, at least about 93% identical, at least about 95% identical, at least about 97% identical, at least about 98% identical and/or at least about 99% identical to SEQ ID NO: 18 and/or a functional fragment thereof. In another embodiment, the FabG enzyme has an amino acid sequence that is identical to SEQ ID NO: 18. In certain embodiments, the FabG is a variant of the wild-type FabG of SEQ ID NO: 18 for example a FabG having at least 90% (91%, 92%, 93%, 94%, 95%, 96%, 97%, 98%, and 99%) sequence identity to SEQ ID NO: 18. In some embodiments, the variant FabG will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:18.

FabG homologs are known in the art; for example FabG may be derived from *E. coli* strains and reference is made, for example to Lai and Cronan, 2004, J. Bacteriol. Mar. p.

1869-1878. FabG is a highly conserved gene and homologs can be found in plants (e.g., *Arabidopsis thaliana*, AT2G30200); mammals (e.g., *Canis familiaris* ENSCAFP0000) 1310); yeast (e.g., *Schizosaccharomyces pombe* SPAC11G75c); and other bacteria (e.g., *Shigella flexneri*).

FabG activity can be assayed in a number of well-known ways. One example is to generate a temperature sensitive strain and reference is made to Lai and Cronan 2004, J. Bacteriol. Mar. p. 1869. Another method to measure FabG activity is to purify the enzyme and test for in vitro activity by measuring the product of the reaction acetoacetyl-ACP+NADPH+$H^+$ to (R)-3-hydroxybutanoyl-ACP+$NADP^+$.

As indicated herein, "heterologous FabG" encompasses wild-type FabGs, variants and functional fragments thereof. In various embodiments, a functional fragment of a full-length wild-type FabG or a variant FabG comprises at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises at least about 80%, at least about 85%, at least about 90%, at least about 91%, at least about 92%, at least about 93%, at least about 94%, at least about 95%, at least about 96%, at least about 97%, at least about 98%, or at least about 99% of the amino acid sequence of a full-length FabG polypeptide.

In another aspect, the present invention provides polynucleotides encoding FabG enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FabG polypeptide encompassed by the invention is coded for by a polynucleotide sequence that has been codon optimized. In particular embodiments, the polynucleotides that encode the FabG enzymes described herein are codon-optimized for expression in a host *E. coli* cell. Indeed, it is intended that the polynucleotides of the present invention be produced using any suitable methods and components as known in the art.

In some embodiments, a FabG enzyme is encoded by a polynucleotide sequence that has at least about 75%, at least about 80%, at least about 85%, at least about 90%, at least about 93%, at least about 95%, at least about 96%, at least about 97%, or at least about 99% sequence identity to SEQ ID NO: 17 and further hybridizes with SEQ ID NO: 17 under medium, medium-high, high or very high stringency conditions.

In some embodiments, a FabI enzyme coded for by a recombinant polynucleotide comprises an amino acid sequence that is at least about 80% identical, at least about 85% identical, at least about 90% identical, at least about 93% identical, at least about 95% identical, at least about 97% identical, at least about 98% identical and/or at least about 99% identical to SEQ ID NO:20 and/or a functional fragment thereof. In another embodiment, the FabI enzyme has an amino acid sequence that is identical to SEQ ID NO:20. In certain embodiments, the FabI is a variant of the wild-type FabI of SEQ ID NO:20; for example a FabI having at least 90%, (91%, 92%, 93%, 94%, 95%, 96%, 97%, 98%, and 99%) sequence identity to SEQ ID NO: 20. In some embodiments, the variant FabI will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:20.

FabI homologs are known in the art; for example FabI may be derived from *E. coli* strains or from *Rhodobacter* strains such as *R. capsulatus* (see, Heath and Rock, 1996, JBC 271:44(11) 27795-27801. In some embodiments, FabI homologues will have a sequence identity that is less than 90% but greater than 40% to SEQ ID NO: 20; that is less than 85% but greater than 40% to SEQ ID NO: 20; that is less than 75% but greater than 40% to SEQ ID NO: 20; that is less than 65% but greater than 40% to SEQ ID NO: 20; and that is less than 55% but greater than 40% to SEQ ID NO: 20.

FabI activity can be assayed in a number of well-known ways. For example complementation assays as previously mentioned above for other Fab enzyme activity and reference is made to Heath and Rock (1995) JBC 270:44 (3) 26538-26542. Further assays include in-vitro measurements of the FabI reaction such as measurement of product from crotonyl-ACP+NADH+$H^+$ to butyryl-ACP+$NAD^+$. Dehydration assays as described in Heath and Rock (1996) JBC 271:44(11) 27795-27801 may also be used to measure FabI activity.

As indicated herein, "heterologous FabI" encompasses wild-type FabIs, variants and functional fragments thereof. In various embodiments, a functional fragment of a full-length wild-type FabI or a variant FabI comprises at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises at least about 80%, at least about 85%, at least about 90%, at least about 91%, at least about 92%, at least about 93%, at least about 94%, at least about 95%, at least about 96%, at least about 97%, at least about 98%, or at least about 99% of the amino acid sequence of a full-length FabI polypeptide, such as an *E. coli* FabI or a *Rhodobacter capsulatus* FabI (such as SEQ ID NO: 20).

In another aspect, the present invention provides polynucleotides encoding FabI enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FabI polypeptide encompassed by the invention is coded for by a polynucleotide sequence that has been codon optimized. In particular embodiments, the polynucleotides that encode the FabI enzymes described herein are codon-optimized for expression in a host *E. coli* cell. Indeed, it is intended that the polynucleotides of the present invention be produced using any suitable methods and components as known in the art.

In some embodiments, a FabI enzyme is encoded by a polynucleotide sequence that has at least about 75%, at least about 80%, at least about 85%, at least about 90%, at least about 93%, at least about 95%, at least about 96%, at least about 97%, or at least about 99% sequence identity to SEQ ID NO: 19 and further hybridizes with SEQ ID NO: 19 under medium, medium-high, high or very high stringency conditions.

In some embodiments, a FabZ enzyme coded for by a recombinant polynucleotide comprises an amino acid sequence that is at least about 80% identical, at least about 85% identical, at least about 90% identical, at least about 93% identical, at least about 95% identical, at least about 97% identical, at least about 98% identical and/or at least about 99% identical to SEQ ID NO:22 and/or a functional fragment thereof. In another embodiment, the FabZ enzyme has an amino acid sequence that is identical to SEQ ID NO:22. In certain embodiments, the FabZ is a variant of the wild-type FabZ of SEQ ID NO:22; for example a FabZ having at least 90%, (91%, 92%, 93%, 94%, 95%, 96%, 97%, 98% and 99%) sequence identity to SEQ ID NO: 22. In some embodiments, the variant FabZ will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:22.

FabZ homologs are known in the art; for example FabZ may be derived from *E. coli* strains (see, Heath and Rock 1996, JBC 271:44(11) 27795-27801).

FabZ activity can be assayed in a number of well-known ways. One example includes dehydration assays using an in-vitro system as described in Heath and Rock, 1996 JBC 271:44(11) 27795-27801.

As indicated herein, "heterologous FabZ" encompasses wild-type FabZs, variants and functional fragments thereof. In various embodiments, a functional fragment of a full-length wild-type FabZ or a variant FabZ comprises at least about 80%, at least about 85%, at least about 90%, at least about 91%, at least about 92%, at least about 93%, at least about 94%, at least about 95%, at least about 96%, at least about 97%, at least about 98%, or at least about 99% identical to the wild-type or reference amino acid sequence. In certain embodiments, a functional fragment comprises at least about 80%, at least about 85%, at least about 90%, at least about 91%, at least about 92%, at least about 93%, at least about 94%, at least about at least 95%, at least about 96%, at least about 97%, at least about 98%, or at least about 99% of the amino acid sequence of a full-length FabZ polypeptide.

In another aspect, the present invention provides polynucleotides encoding FabZ enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FabZ polypeptide encompassed by the invention is coded for by a polynucleotide sequence that has been codon optimized. In particular embodiments, the polynucleotides that encode the FabZ enzymes described herein are codon-optimized for expression in a host *E. coli* cell. Indeed, it is intended that the polynucleotides of the present invention be produced using any suitable methods and components as known in the art.

In some embodiments, a FabZ enzyme is encoded by a polynucleotide sequence that has at least about 75%, at least about 80%, at least about 85%, at least about 90%, at least about 93%, at least about 95%, at least about 96%, at least about 97%, or at least about 99% sequence identity to SEQ ID NO: 21 and further hybridizes with SEQ ID NO:21 under medium, medium-high, high or very high stringency conditions.

In some embodiments, a FabB enzyme coded for by a recombinant polynucleotide comprises an amino acid sequence that is at least about 80% identical, at least about 85% identical, at least about 90% identical, at least about 93% identical, at least about 95% identical, at least about 97% identical, at least about 98% identical and/or at least about 99% identical to SEQ ID NO:28 and/or a functional fragment thereof. In another embodiment, the FabB enzyme has an amino acid sequence that is identical to SEQ ID NO:28. In certain embodiments, the FabB is a variant of the wild-type FabB of SEQ ID NO:28 for example a FabB having at least 90%, (91%, 92%, 93%, 94%, 95%, 96%, 97%, 98%, and 99%) sequence identity to SEQ ID NO: 28. In some embodiments, the variant FabB will have at least 1, at least 2, at least 3, at least 4, at least 5, at least 6, at least 7, at least 8, at least 9, at least 10, at least 12, at least 14, at least 16, at least 18, at least 20 or more amino acid alterations (e.g., substitutions, deletions and/or insertions) relative to SEQ ID NO:28.

FabB homologs are known in the art; for example FabB may be derived from *E. coli* strains (see, Kitagawa M. et al., (2005) DNA Res., 12:291-299). Other non-limiting examples of FabB homologous are *Drosophila pseudoobscura* (GA 17498-PA) and *Xenopus tropicalis* (ENSXETP00000009583).

FabB activity can be assayed in a number of well-known ways. For example, enzymatic activity can be measured in-vitro by purifying a FabB enzyme. In general the reaction of dodecanoyl-ACP+a malonyl-ACP to 3-oxo-myristoyl-ACP+$CO_2$+a holo-ACP is measured. In addition complementation assays can be conducted with temperature sensitive FabB and reference is made to Mendoza et al., (1983) JBC 258:4925) 2098-2101.

As indicated herein, "heterologous FabB" encompasses wild-type FabBs, variants and functional fragments thereof. In various embodiments, a functional fragment of a full-length wild-type FabB or a variant FabB comprises at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises at least about 80%, at least about 85%, at least about 90%, at least about 91%, at least about 92%, at least about 93%, at least about 94%, at least about 95%, at least about 96%, at least about 97%, at least about 98%, or at least about 99% of the amino acid sequence of a full-length FabB polypeptide.

In another aspect, the present invention provides polynucleotides encoding FabB enzymes as described above. The polynucleotide can be a DNA or RNA, and can be single-stranded or double-stranded. The polynucleotide can be isolated from a naturally occurring microorganism, or prepared wholly or partially via synthetic means.

In certain embodiments, the FabB polypeptide encompassed by the invention is coded for by a polynucleotide sequence that has been codon optimized. In particular embodiments, the polynucleotides that encode the FabB enzymes described herein are codon-optimized for expression in a host *E. coli* cell. Indeed, it is intended that the polynucleotides of the present invention be produced using any suitable methods and components as known in the art.

In some embodiments, a FabB enzyme is encoded by a polynucleotide sequence that has at least about 75%, at least about 80%, at least about 85%, at least about 90%, at least about 93%, at least about 95%, at least about 96%, at least about 97%, or at least about 99% sequence identity to SEQ ID NO: 27 and further hybridizes with SEQ ID NO:27 under medium, medium-high, high or very high stringency conditions.

In some embodiments, a recombinant or engineered microbial host cell encompassed by the invention will comprise: a first introduced polynucleotide encoding a FAR enzyme (for example a polynucleotide encoding a FAR enzyme having at least 90% (also at least 93%, 95%, 96%, 97%, 98%, 99% and even 100%) sequence identity to SEQ ID NOs: 2, 4, 6, or 8; a second introduced polynucleotide encoding a FabH having at least 90% (also at least 93%, 95%, 96%, 97%, 98%, 99% and even 100%) sequence identity to SEQ ID NO: 10; and optionally one or more additional introduced polynucleotides comprises a) a polynucleotide encoding a FabD having at least 90% (also at least 93%, 95%, 96%, 97%, 98%, 99% and even 100%) sequence identity to SEQ ID NO: 26; b) a polynucleotide encoding a FabF having at least 90% (also at least 93%, 95%, 96%, 97%, 98%, 99% and even 100%) sequence identity to SEQ ID NO: 29; c) a polynucleotide encoding a FabG having at least 90% (also at least 93%, 95%, 96%, 97%, 98%, 99% and even 100%) sequence identity to SEQ ID NO: 17; d) a polynucleotide encoding a FabI having at least 90% (also at least 93%, 95%, 96%, 97%, 98%, 99% and even 100%) sequence identity to SEQ ID NO: 19; e) a polynucleotide encoding a FabZ having at least 90% (at least 93%, 95%, 96%, 97%, 98%, 99% and even 100%) sequence identity to SEQ ID NO: 21, f) a polynucleotide encoding a FabB having at least 90% (at least 93%, 95%, 96%, 97%, 98%, 99% and even 100%) sequence identity to SEQ ID NO: 27 and g) a combination of anyone of a) to f).

In some embodiments, a recombinant or engineered microbial host cell encompassed by the invention will comprise: a first introduced polynucleotide encoding a FAR enzyme (for example a polynucleotide encoding a FAR enzyme having at least 90% (also at least 93%, 95%, 96%, 97%, 98%, 99% and even 100%) sequence identity to SEQ ID NOs: 2, 4, 6, or 8; a second introduced polynucleotide encoding a FabH having at least 90% (also at least 93%, 95%, 96%, 97%, 98%, 99% and even 100%) sequence identity to SEQ ID NO: 10; a third introduced polynucleotide encoding a FabD having at least 95% (also at least 96%, 97%, 98%, 99% and even 100%) sequence identity to SEQ ID NO: 26 and a fourth introduced polynucleotide encoding a FabG having at least 95% (also at least 96%, 97%, 98%, 99% and even 100%) sequence identity to SEQ ID NO: 17.

4. DNA Constructs, Vectors and Transformation:

In some embodiments, the nucleic acid coding for the FAR and FabH enzymes as described herein are co-expressed on the same vector and are operably linked to a promoter, and optionally, to other control sequences.

In some embodiments, the invention encompasses a vector comprising a first nucleic acid sequence encoding a FAR having an amino acid sequence that is at least about 70% identical, at least about 75%, at least about 80% identical, at least about 85% identical, at least about 90% identical, at least about 93% identical at least about 95% identical, at least about 97% identical, at least about 98% identical and/or at least about 99% identical to SEQ ID NOs:2, 4, 6 or 8 and/or a functional fragment thereof and comprising a second nucleic acid sequence encoding a FabH having an amino acid sequence that is at least about 70% identical, at least about 75%, at least about 80% identical, at least about 85% identical, at least about 90% identical, at least about 93% identical at least about 95% identical, at least about 97% identical, at least about 98% identical and/or at least about 99% identical to SEQ ID NO: 10 and/or a functional fragment thereof. In other embodiments, the vector will comprise a first nucleic acid sequence encoding a FAR having an amino acid sequence that is at least 95% identical to SEQ ID NO: 8 and a second nucleic acid sequence encoding a FabH having at least 95% sequence identity to SEQ ID NO: 10.

In some embodiments, a vector will compromise a first DNA construct encoding a FAR enzyme and a second DNA construct encoding a FabH enzyme and each DNA construct will have the same promoter. In other embodiments, the promoter will be different for the nucleic acid sequence encoding the FAR enzyme and the nucleic acid sequence encoding the FabH enzyme. In some embodiments, the FAR encoding genes will be transcribed first on the vector and in other embodiments the FabH encoding gene will be transcribed first on the vector. Suitable promoters include, but are not limited to constitutive promoters, regulated promoters, and inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art. See e.g. Nevoigt et al. (2006) *Appl. Environ. Microbiol.* 72:5266-5273, the disclosure of which is herein incorporated by reference in its entirety.

Polynucleotides coding for the introduced Fab enzymes as described herein above and the vectors comprising said polynucleotides or DNA constructs include polynucleotides comprising a sequence having at least 90% (at least 91%, 92%, 93%, 94%, 95%, 96%, 97%, 98%, 99% and even 100%) sequence identity to SEQ ID NO: 25 encoding a FabD; polynucleotides comprising a sequence having at least 90% (at least 91%, 92%, 93%, 94%, 95%, 96%, 97%, 98%, 99% and even 100%) sequence identity to SEQ ID NO: 17 encoding a FabG; polynucleotides comprising a sequence having at least 90% (at least 91%, 92%, 93%, 94%, 95%, 96%, 97%, 98%, 99% and even 100%) sequence identity to SEQ ID NO: 19 encoding a FabI; polynucleotides comprising a sequence having at least 90% (at least 91%, 92%, 93%, 94%, 95%, 96%, 97%, 98%, 99% and even 100%) sequence identity to SEQ ID NO: 21 encoding a FabZ; and polynucleotides comprising a sequence having at least 90% (at least 91%, 92%, 93%, 94%, 95%, 96%, 97%, 98%, 99% and even 100%) sequence identity to SEQ ID NO: 27 encoding a FabB.

For bacterial host cells, suitable promoters for directing transcription of the nucleic acid constructs of the present disclosure, include, but are not limited to the promoters obtained or derived the *E. coli* lac operon, *Streptomyces coelicolor* agarase gene (dagA). *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis penicillinase* gene (penP). *Bacillus subtilis* xylA and xylB genes, *Bacillus megaterium* promoters, and prokaryotic beta-lactamase gene (VIIIa-Kamaroff et al., *Proc. Natl Acad. Sci. USA* 75: 3727-3731 (1978)), as well as the tac promoter (DeBoer et al., *Proc. Natl Acad. Sci. USA* 80: 21-25 (1993)). Additional promoters include trp promoter, phage lambda PL, T7 promoter, promoters found at PromEC. See e.g., the website margalit.huji.ac.il/promec/index.html. Particularly useful promoters include the Tre promoter (Brosius J. et al., (1985) J. Biol. Chem. 260: 3539-3541). Additional promoters suitable for use in the present disclosure are described in Terpe H., 2006, Appl. Microbiol. Biotechnol. 72:211-222 and in Sambrook et al., (2001) *Molecular Cloning: A Laboratory Manual*, 3$^{rd}$ ed., Cold Spring Harbor Laboratory Press, New York.

In various embodiments, an expression vector optionally contains a ribosome binding site (RBS) for translation initiation, and a transcription terminator, such as the transcriptional terminators $T_1$ and $T_2$ derived from the rrnB operon from *E. coli* (See e.g., Orosz et al., (1991) Eur. J. Biochem. 201: 653-659). RBS are effective control elements for protein production and the type of RBS can result in different expression levels of the same protein or enzyme. In some embodiments, the expression of a Fab enzyme may be too high for the microbial system resulting in toxicity if other enzymes in the metabolic pathway are not capable or evolved to utilize the expressed protein. Studies have been conducted to design RBS to provide optimized protein expression. In general the mRNA region containing the RBS may range from about 18 to 50 nucleic acid residues in length. The RBS in bacteria are usually located about 8 base pairs upstream of the start codon. To accelerate the development of optimized enzyme pathway engineering both library based approaches and biophysical models using algorithms to predict a RBS with target translation initiation rates have been explored and reference is specifically made to H. Salis et al., Nature Biotechnology 2009, 27(10) 946-951. One skilled in the art is aware of a number of well-characterized RBS and reference is made to Vellanoweth & Rabinowitz, 1992 [Mol. Microbiol. 6: 1105-1114. The influence of ribosome-binding-site elements on translational efficiency in *B. subtilis* and *E. coli* in vivo].

In addition one of skill in the art could use the algorithm described in Slais et al., supra, to calculate other RBS sequences with similar translational efficiencies and then empirically test these sequences. In some embodiments according to the instant invention, a 23 base pair RBS region was taken from the native *E. coli* FabA gene SEQ ID NO: 60 (5' ATAAAATAAGGCTTACAGAGAAC) and also from the native *E. coli* FabH gene, SEQ ID NO: 61 (5'AAC-CGAAAAGTGACTGAGCGTAC) and used as a RBS for FabH expression.

Some embodiments of the instant invention include a DNA construct comprising a promoter, a RBS comprising at least 95%, (96%, 97%, 98%, 99% and 100% sequence identity to SEQ ID NO: 60 or SEQ ID NO: 61 and a nucleic acid coding for a FabH enzyme having at least 80% (at least 85%, 90%, 91%, 92%, 93%, 94%, 95%, 96%, 97%, 98%, 99% and even 100%) sequence identity to SEQ ID NO: 10, wherein the promoter and the RBS are operable linked to the nucleic acid encoding the FabH enzyme. In some embodiments, the DNA construct comprises a first polynucleotide sequence encoding a FAR comprising at least 80%, (for example 85%, 90%, 93%, 95%, 96%, 97%, 98%, 99%, and even 100%) sequence identity to SEQ ID NO: 2, 4, 6 or 8 and a second polynucleotide sequence comprising a RBS comprising at least 95%, (96%, 97%, 98%, 99% and 100% sequence identity to SEQ ID NO: 60 or 61 and a nucleic acid coding for a FabH enzyme having at least 80% (at least 85%, 90%, 91%, 92%, 93%, 94%, 95%, 96%, 97%, 98%, 99% and even 100%) sequence identity to SEQ ID NO: 10, wherein the RBS is located between the FAR and the FabH and is operably linked to the nucleic acid encoding the FabH enzyme. In some embodiments, the vector also optionally includes appropriate sequences for amplifying expression, e.g., translational enhancers.

In various embodiments, the polynucleotides useful for expressing the recombinant enzymes in the bacterial host cells are operably linked to other control sequences, including but not limited to, a transcription terminator sequence, a signal sequence that when translated directs the expressed polypeptide into the secretory pathway of the recombinant host cell, and/or a polyadenylation sequence (eukaryotes). The choice of appropriate control sequences for use in the polynucleotide constructs of the present disclosure is within the skill in the art and in various embodiments is dependent on the recombinant host cell used and the desired method of recovering the fatty alcohol compositions produced. Indeed, it is not intended that the present invention be limited to any particular control sequence(s).

A recombinant expression vector according to the invention can be any suitable vector, e.g., a plasmid or a virus, which can be manipulated by recombinant DNA techniques to facilitate expression of at least one heterologous enzyme in the recombinant host cell. In certain embodiments, the expression vector is integrated into the chromosome of the recombinant host cell and comprises one or more heterologous genes operably linked to one or more control sequences useful for production of at least one heterologous enzyme as described above. In other embodiments, the expression vector is an extra chromosomal replicative DNA molecule, e.g., a linear or closed circular plasmid, that is found either in low copy number (e.g., from about 1 to about 10 copies per genome equivalent (such as at least about 1, 2, 3, 4, 5, 6, 7, 8, 9, or 10)) or in high copy number (e.g., more than about 10 copies per genome equivalent (such as at least 10, at least 15, at least 20, at least 30, at least 40, at least 50 and in some embodiments at least 100. In various embodiments, the expression vector includes a selectable marker, such as a gene that confers antibiotic resistance (e.g. ampicillin, kanamycin, chloramphenicol or tetracycline resistance) to the recombinant host organism that comprises the vector.

Expression vectors which, in certain embodiments, are useful for expressing enzymes as disclosed herein (for example FAR and FabH either singly or co-expressed on the same vector are commercially available e.g., from Sigma-Aldrich Chemicals, St. Louis Mo. and Stratagene. LaJolla Calif. In some embodiments, examples of suitable expression vectors are plasmids which are derived from pBR322 (Gibco BRL), pUC (Gibco BRL), pREP4, pCEP4 (Invitrogen) or pPoly (Lathe et al., 1987 Gene 57:193-201). In certain embodiments, the present disclosure provides a plasmid for expression of heterologous genes in *E. coli*.

Figure 2:
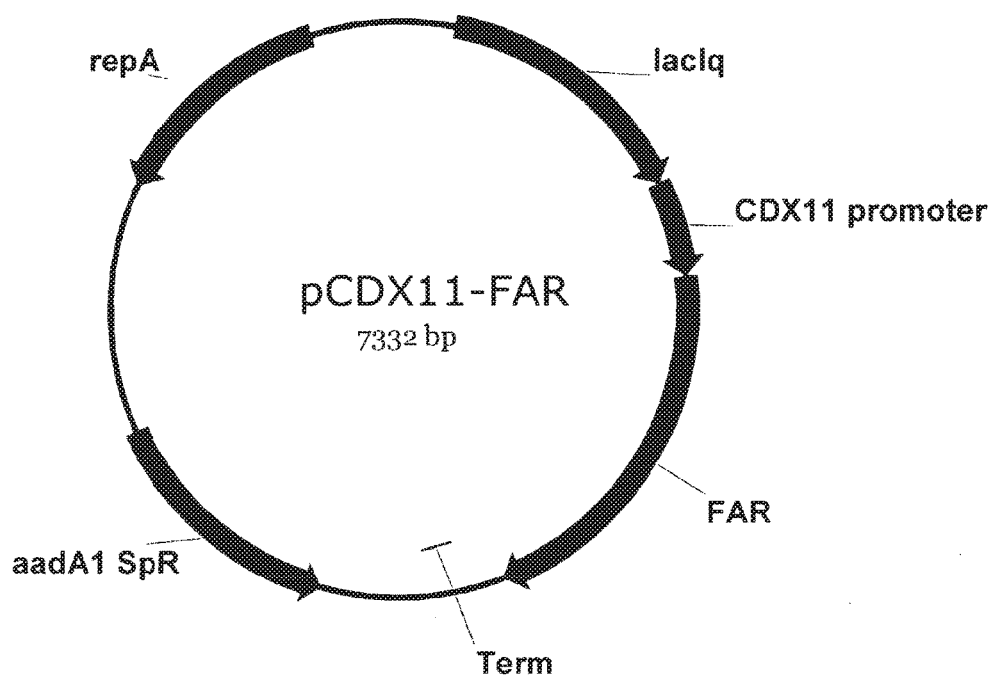
FIG. 2 illustrates plasmid pCDX11-FAR, wherein repA denotes the gene which encodes the protein necessary for plasmid replication from the SC101 ori; aadA1SpR denotes the gene which encodes a spectinomycin resistance protein; lacIq denotes a transcription factor; and CDX11 promoter denotes a synthetic inducible promoter element.

Expression vector pCK110900, which comprises a P15A origin of replication "ori" (P15A ori), lac a CAP binding site, a lac promoter, a T7 ribosomal binding site (T7g10 RBS) and a chloramphenicol resistance gene (camR) is an exemplary vector that finds use in the present invention. This expression vector is depicted in FIG. 3 of U.S. Patent Publication No. 2006/0195947, which is incorporated herein by reference in its entirety. Other suitable plasmid vectors include, but are not limited to derivatives of pCL1920 and pCL1921 (Lerner and Inouye, 1990; NAR 18:4631). These vectors contain the pSC101 ori and confer resistance to spectinomycin (GenBank: AB236930). In some embodiments, the vector is an expression vector derived from pCL1920 including the Trc promoter and the lacIq gene from *E. coli*. pLS8379 (SEQ ID NO: 59). In other embodiments, the vector is the plasmid pCDX11-FAR (FIG. 2).

Methods, reagents and tools for transforming host cells described herein, such as bacteria, are known in the art. General methods, reagents and tools for transforming, e.g. bacteria can be found, for example, in Sambrook et al (2001) Molecular Cloning: A Laboratory Manual, 3$^{rd}$ ed., Cold Spring Harbor Laboratory Press, New York. In some embodiments, introduction of the DNA construct or vector of the present invention into a host cell is accomplished by calcium phosphate transfection, DEAE-dextran mediated transfection, electroporation or other common techniques (See Davis et al., 1986, Basic Methods in Molecular Biology, which is incorporated herein by reference). In one embodiment, a preferred method used to transform *E. coli* strains is electroporation and reference is made to Dower et al., (1988) NAR 16: 6127-6145. Indeed, any suitable method for transforming host cells finds use in the present invention. It is not intended that the present invention be limited to any particular method for introducing nucleic acids such as constructs into host cells.

5. Thioesterase:

According to one embodiment of the invention, a microbial host cell is engineered to express a heterologous FAR; a FabH, and a recombinant thioesterase ("TE"). The thioesterase may be one that preferentially uses C12, C14 or C16 ACPs. Depending on the TE used essentially a homogenous population of fatty alcohols may be produced. For example, if the TE is one that predominantly uses C12 ACPs then the fatty alcohol composition produced by a recombinant microbial cell according to the invention will predominantly comprise fatty alcohols having a carbon chain length of C12.

In some embodiments the expressed TE is one that is classified as TE from the Family TE14 in the ThYme database. These sequences may be downloaded from GenBank and UniProt databases (Nucleic Acid Res 201038: D142-D148).

Some nonlimiting examples of TEs that may be used include the "class I" and "class II" acyl-ACP TE fat genes (e.g. fatA or fatB genes and reference is made to A. Jones et al., 1995, Plant Cell 7:359-371). In particular, FatB are preferred TEs (e.g. plant acyl-ACP TEs) useful in the invention. In some embodiments, the TE may be a bacterial acyl-ACP TE. FatB may be obtained for example from *Umbellularia california* having UniProtKB Accession number Q41635; and NCBI Accession number AAA34215; *Ulmus Americana* having NCBI Accession number AAB71731, *Cuphea hookeriana* NCBI Accession number Q39513: UniProtKB Accession numbers AAC49269; AAC49269; and AAC72881; *Cinnamonum camphorum* having NCBI Accession number Q39473 and UniProtKB AAC49151; and acyl-ACP thioesterases from *Cuphea palustris* (AAC49179; and U.S. Pat. No. 5,955,329). Other TEs include without limitation CnFatB (*Cocos nucifera*, e.g. JF338903; JF338904 and JF338905); ccFAT (*Cinnamomum camphora*); pdFat (*Parabacleroides distasonis*, ATCC 8503); gsFat (*Geobacillus* sp. Y412MC10); pvFAT (*Paenibacillus vortex* V453); pm FAT (*Parabacteroides merdae* ATCC 43184); cvFatB (*Cuphea viscosissima*. JF338906; JF338907; and JF338908); eoFat (*Elaeis oleifera*) AAD42220 (*Elaeis guineensis*) and mlFat (*Madhuca longofolia* var. *latifolia*).

In some embodiments, homologous or analogous TE genes will be used for the heterologous expression of a TE enzyme.

It is known that different acyl-ACP TE have different degrees of chain length specificity. In some embodiments, the TE useful in the invention is a TE having a preference for cleaving chain lengths of any one of C12, C14 and/or C16 fatty acids from ACP. In some embodiments, having a preference for cleaving chain lengths of any one of C12, C14 and/or C16 fatty acids from ACP means that the thioester hydrolysis will produce fatty acids having at least 85%. (such as at least 88%, 90%, 93%, 95%, 96%, 97%, 98% or more) of any one of C12, C14 and/or C16 carbon chain lengths.

In one embodiment, the TE is encoded by a gene comprising the polynucleotide sequence having at least 70%, (at least 75%, 80%, 85%, 90%, 93%, 95%, 97%, 99%, and even 100%) sequence identity to the polynucleotide sequence of SEQ ID NO: 11 or SEQ ID NO: 62. In some embodiments, the TE enzyme will comprise at least 70%, (at least 75%, 80%, 85%, 90%, 93%, 95%, 97%, 99%, and even 100%) sequence identity to the polypeptide sequence of SEQ ID NO: 12 or SEQ ID NO: 63. In some embodiments, the TE gene will comprise at least 85% (at least 88%, 90%, 93%, 95%, 96%, 97%, 98%, 99% and even 100%) sequence identity to the polynucleotide sequence of SEQ ID NO: 11 or SEQ ID NO: 62. In some embodiments, the TE enzyme will comprise at least 85% (at least 88%, 90%, 93%, 95%, 96%, 97%, 98%, 99% and even 100%) sequence identity to the polypeptide sequence of SEQ ID NO: 12 or SEQ ID NO: 63. In some embodiments the gene encoding the TE enzyme is derived from *Umbelluria californica* (California Bay), and in other embodiments the gene encoding the TE enzyme is derived from *Cinnamomum camphorum*.

In some embodiments, the TE enzyme will be a functional fragment of a native TE, such as a TE having deletions at the N-terminal amino acid positions. In certain embodiments, the functional fragment will comprise at least 95% of the reference enzyme. In certain embodiments, the functional fragment will include a deletion of at least 1, 2, 3, 4, 5, 6, 7, 8, 9, 10 or more amino acid residues. In some embodiments, the TE is a variant enzyme having at least 1, at least 5, at least 10, at least 15 or more amino acid modifications, such as substitutions. Non-limiting examples include the TE FatB genes from California Bay. *Cinnamomun camphora* and from various *Cuphea* species such as those disclosed in WO 2011/008565 and reference is made to SEQ ID NOs. 21, 48, 52, 56, 60, 64, 66, 70, 72, 76, 80, 82, 86, 90, 92, 94, 96 and 100 described therein.

Further acyl-ACP TEs that are useful according to the invention are described in the following references: U.S. Pat. No. 5,344,771; U.S. Pat. No. 5,512,482; U.S. Pat. No. 6,150,512; U.S. Pat. No. 5,723,761; U.S. Pat. No. 5,910,631 and WO2010/075483.

In some embodiments, a bacterial host cell encompassed by the invention will be transformed with a vector comprising a first nucleic acid coding for a FAR; a second nucleic acid coding for a FabH enzyme and a third nucleic acid coding for a TE enzyme. In some embodiments, all three nucleic acid sequences are found on the same vector and in other embodiments each nucleic acid encoding any one of FAR, FabH or TE are found on different vectors. In some embodiments each nucleic acid sequence may include the same or different promoters which are operably linked to the nucleic acid coding for the FAR, FabH or TE. In various embodiments the nucleic acid sequence encoding the FAR, FabH and TE are optionally linked to other control sequences.

In some embodiments, the engineered prokaryotic cell (such as *E. coli*) will comprise three recombinant polynucleotides, the first polynucleotide encoding a FAR variant comprising at least 95% sequence identity to SEQ ID NO:2, SEQ ID NO: 4; SEQ ID NO: 6, and/or SEQ ID NO: 8; the second polynucleotide encoding a FabH comprising at least 90% (at least 95%) sequence identity to SEQ ID NO: 10; and a third polynucleotide encoding a TE comprising at least 90% or 95% sequence identity to SEQ ID NO: 12 or SEQ ID NO: 63 and optionally the engineered prokaryotic cell will comprise a fourth introduced polynucleotide encoding a FadD comprising at least 95% sequence identity to SEQ ID NO: 16, wherein the engineered cells produce a fatty alcohol composition comprising C12 and C14 fatty alcohols.

Various assays are known which can be used to test for TE activity in a recombinant microorganism transformed with a vector comprising a polynucleotide encoding a TE according to the invention (See, Voelker and Davies. 1994, J. Bacteriol. 76:7320).

As described above, the term "acyl-CoA synthetase" is used synonymously with "ACS" or "acyl-CoA synthetase" or "FadD". These enzymes mediate the formation of acyl-CoA esters (See, FIG. 1). According to an embodiment of the invention, a microbial host cell is engineered to express a recombinant ACS. ACS that can be expressed to produce acyl-CoA includes the *E. coli* fadD gene comprising the polynucleotide sequence of SEQ ID NO: 15 which codes for the ACS comprising the polypeptide sequence of SEQ ID NO: 16. In some embodiments, the fadD gene will comprise at least 70%, (at least 75%, 80%, 85%, 90%, 93%, 95%, 97%, 99%, and even 100%) sequence identity to the polynucleotide sequence of SEQ ID NO: 15. In some embodiments, the ACS enzyme encoded by a ACS polynucleotide will comprise at least 70%, (at least 75%, 80%, 85%, 90%, 93%, 95%, 97%, 99%, and even 100%) sequence identity to the polypeptide sequence of SEQ ID NO: 16. In some embodiments, fadD encodes an ACS variant enzyme having at least 1, at least 5, at least 10, at least 15 or more amino acid modifications, such as substitutions. Non-limiting examples include modifications to the gene encoding the ACS of SEQ ID NO: 16.

In some embodiments, homologous fadD genes will be used for the heterologous expression of an ACS enzyme to produce acyl-CoAs. These fadD genes include without limitation, fadD from *Acinetobacter* sp. NCBI ID YP_045024; fadD from *Haemophilus influenza* NCBI ID NP_438551; fadD from *Pseudomonas aeruginosa* NCBI ID_251989 and 251990; BH3101 from *Bacillus halodurans* NP_243969; yhfL from *Bacillus subtilis* NP_388908: and fadD from *Rhizobium etli* CFN NCBI ID_533919; fadD from *Marinobacter algicola* ZP_01892995; fadD from *Marinobacter aquaeolei* YP_958864; fadD from *Mycobacterium tuberculosis* NP_215722; fadD 15 from *Mycobacterium tuberculosis* NP_216703; fadD 19 from *Mycobacterium tuberculosis* YP_177983; fadD from *Rhodopseudomonas palustris* YP_00993712; fadD from *Pseudomonas fluorscens* PfO-1 YP_350081; fadD from *Pseudomonas putida* ACC77300; fadK from *E. coli* strain W ZP_07590374; putative fadK from *Salmonella typhimurium* LT2 NP_460316; and putative fadK from *Thermomonospora fusca* YP_290214.

In some embodiments, an engineered host cell according to the invention (e.g. a bacterial host cell) will comprise a first introduced nucleic acid sequence encoding a FAR having an amino acid sequence that is at least about 70% identical, (e.g., at least about 75%, at least about 80%, at least about 85%, at least about 90%, at least about 93%, at least about 95%, at least about 97%, at least about 98% and/or at least about 99%) identical to SEQ ID NOs:2, 4, 6 or 8 and/or a functional fragment thereof; a second introduced nucleic acid sequence encoding a FabH having an amino acid sequence that is at least about 70% identical, (e.g. at least about 75%, at least about 80%, at least about 85%, at least about 90%, at least about 93%, at least about 95%, at least about 97%, at least about 98%, at least about 99% and even 100%) identical to SEQ ID NO: 10 and/or a functional fragment thereof; a third introduced nucleic acid sequence encoding a TE having at least about 85% (e.g., at least about 88%, at least about 90%, at least about 93%, at least about 95%, at least about 96%, at least about 97%, at least about 98%, at least about 99% and even 100%) sequence identity to the polypeptide sequence of SEQ ID NO:12 or SEQ ID NO: 63 and optionally a fourth introduced nucleic acid sequence encoding a FadD having an amino acid sequence that is at least about 80%, (e.g., at least about 85%, at least about 88%, at least about 90%, at least about 93%, at least about 95%, at least about 96%, at least about 97%, at least about 98%, at least about 99% and even 100%) identical to SEQ ID NO: 16 or a functional fragment thereof. In some embodiments, the engineered microorganism comprising the at least three nucleic acid sequences encoding a FAR, a FabH and a TE will produce a fatty alcohol composition comprising at least 50% (at least 55%, at least 60%, at least 65%, at least 70%, at least 75%, at least 80%, and at least 85%) C12 and/or C14 saturated and/or unsaturated fatty alcohols. In some embodiments, the engineered microorganism comprising the at least four nucleic acid sequences encoding a FAR, a FabH, a TE and a FadD will produce a fatty alcohol composition comprising at least 50% (at least 55%, at least 60%, at least 65%, at least 70%, at least 75%, at least 80%, and at least 85%) C12 and/or C14 saturated and/or unsaturated fatty alcohols.

6. Endogenous Gene Inactivations:

In some embodiments, endogenous genes of the engineered microorganism of the present invention have been inactivated. For example, the genes have been genetically modified to at least partially delete a gene encoding the endogenous enzyme (e.g., FadE, FabF or FadR). Typically, these modifications of the gene reduce or eliminate the total amount of endogenous enzyme produced by the host cell. In some embodiments, complete or near-complete deletion of the gene sequence is contemplated. However, a deletion mutation need not completely remove the entire gene sequence encoding the enzyme, in order to reduce the amount of endogenous enzyme produced by the engineered cell. For example, in some embodiments, there is a partial deletion that removes one or more nucleotides encoding a portion of an enzyme (e.g., FadE) that plays a role in endogenous enzyme activity by the host cell (See, U.S. Pat. No. 8,110,670).

A deletion in a gene encoding an enzyme (e.g., FadE, FabF and/or FadR) in accordance with the embodiments provided herein includes a deletion of one or more nucleotides in the gene encoding the target enzyme (e.g., FadE, FabF and/or FadR). In some embodiments, there is a deletion of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100%, of the gene (e.g. a gene encoding for example FadE, FabF and/or FadR), wherein the amount of enzyme produced by the cell is reduced.

Thus, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the enzyme activity produced by the cell, relative to the enzyme activity of a corresponding enzyme produced by an unmodified organism grown or cultured under essentially the same culture conditions and including the gene coding for the corresponding enzyme which had not be inactivated or deleted. In some embodiments, deletion is of a fadF gene, a fadE gene, a fadD gene or a fadR gene.

Deletion of a gene of interest can be detected and confirmed by any of a variety of methods known in the art for detection of gene deletions, including the methods provided herein. For example, gene deletion can be confirmed using PCR amplification of the modified genomic region. It will be appreciated that additional suitable techniques for confirming deletion can be used and are well known, including but not limited to Southern blot techniques, DNA sequencing of the modified genomic region, and screening for positive or negative markers incorporated during recombination events.

Some additional methods for complete and/or partial deletion of a gene are well-known. The genetically modified cells described herein can be generated using any of a variety of deletion methods known in the art that result in the complete inactivation or at least a reduction in the amount of at least one endogenous gene expressed by the cells.

There are numerous approaches to create genetic modifications in bacteria (See e.g., Court et al., (2002) Annual Rev. Genet 36:361-388; and Datsenko and Wanner (2000) PNAS 97:6640-6645).

In some embodiments, the engineered microorganism will comprise an inactivated gene which codes for a FabF enzyme wherein the FabF comprises an amino acid sequence that is at least about 80% identical, at least about 85% identical, at least about 90% identical, at least about 93% identical, at least about 95% identical, at least about 97% identical, at least about 98% identical, at least about 99% identical and even 100% identical to SEQ ID NO:30. In some embodiments, the FabF is encoded by a nucleic acid sequence comprising at least 90%, at least 93%, at least 95%, at least 96%, at least 97%, at least 98%, at least 99% and even 100% sequence identity to the polynucleotide sequence of SEQ ID NO: 29. In some embodiments, the FabF is encoded by a nucleic acid sequence that can selectively hybridize to SEQ ID NO:29 under moderately stringent or highly stringent conditions, as described hereinabove. To determine if FabF activity has been inactivated one of skill in the art may use a number of different assays. These assays include but are not limited to the measurement of thermal sensitivity, the measurement of reduction of cis-vaccenate (oleic acid) portion of cells as described for example in Mendoza et al., (1983) JBC 258:4(25) 2098-2101; and verification of gene deletion by PCR or sequencing.

In certain embodiments the inactivation is of a fadR gene sequence encoding a FadR enzyme. For example, in one embodiment, the polynucleotide sequence encoding a FadR enzyme is set forth herein as SEQ ID NO:23, and the encoded amino acid sequence is set forth as SEQ ID NO:24. In some embodiments, the FadR is encoded by a nucleic acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% identical to SEQ ID NO:23. In some embodiments, the FadR is encoded by a nucleic acid sequence that can selectively hybridize to SEQ ID NO:23 under moderately stringent or highly stringent conditions, as described hereinabove. In some embodiments, the FadR enzyme has an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% identical to SEQ ID NO:24.

In certain embodiments the inactivation is of a fadE gene sequence encoding a FadE enzyme. For example, in one embodiment, the polynucleotide sequence encoding a FadE enzyme is set forth herein as SEQ ID NO: 13, and the encoded amino acid sequence is set forth as SEQ ID NO: 14. In some embodiments, the FadE is encoded by a nucleic acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% identical to SEQ ID NO:13. In some embodiments, the FadE is encoded by a nucleic acid sequence that can selectively hybridize to SEQ ID NO: 13 under moderately stringent or highly stringent conditions, as described hereinabove.

In some embodiments, the FadE has an amino acid sequence that is at least about 709%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or even 100% identical to SEQ ID NO: 14. FadE sequences can be identified by any of a variety of methods known in the art. For example, a sequence alignment can be conducted against a database, for example against the NCBI database, and sequences with the lowest HMM E-value can be selected (Cho et al. 1995 J. Biol. Chem. 270:4216-4219).

In certain embodiments, in addition to a polynucleotide encoding a FabH being introduced into a microbial cell according to the invention, the engineered microbial cell may further comprise an inactivated endogenous FabH. For example, in one embodiment, the polynucleotide sequence encoding a FabH enzyme is set forth herein as SEQ ID NO:9, and the encoded amino acid sequence is set forth as SEQ ID NO: 10. In some embodiments, the FabH is encoded by a nucleic acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or even 100% identical to SEQ ID NO: 10. In some embodiments, the FabH is encoded by a nucleic acid sequence that can selectively hybridize to SEQ ID NO:9 under moderately stringent or highly stringent conditions, as described hereinabove.

In some embodiments, the FabH has an amino acid sequence that is at least about 709%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:10.

In certain embodiments the inactivation is of a fadD polynucleotide sequence encoding a FadD enzyme. For example, in one embodiment, the polynucleotide sequence encoding a FadD enzyme is set forth herein as SEQ ID NO:15, and the encoded amino acid sequence is set forth as SEQ ID NO: 16. In some embodiments, the FadD is encoded by a nucleic acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or even 100% identical to SEQ ID NO: 16. In some embodiments, the FadD is encoded by a nucleic acid sequence that can selectively hybridize to SEQ ID NO: 15 under moderately stringent or highly stringent conditions, as described hereinabove.

In some embodiments, the FadD has an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or even 100% identical to SEQ ID NO: 16. FadD sequences can be identified by any of a variety of methods known in the art. For example, a sequence alignment can be conducted against a database, for example against the NCBI database, and sequences with the lowest HMM E-value can be selected (Black, P. N. et al., 1992, J. Biol. Chem., 267:25513-25520).

In some embodiments, a recombinant or engineered microbial host cell encompassed by the invention will comprise: a first introduced polynucleotide encoding a FAR enzyme (for example a polynucleotide encoding a FAR enzyme having at least 90% (also at least 93%, 95%, 96%, 97%, 98%, 99% and even 100%) sequence identity to SEQ ID NOs: 2, 4, 6, or 8: a second introduced polynucleotide encoding a FabH having at least 90% (also at least 93%, 95%, 96%, 97%, 98%, 99% and even 100%) sequence identity to SEQ ID NO: 10; and optionally one or more introduced polynucleotides encoding a FabD having at least 90% (also at least 93%, 95%, 96%, 97%, 98%, 99% and even 100%) sequence identity to SEQ ID NO: 26; a FabG having at least 90% (also at least 93%, 95%, 96%, 97%, 98%, 99% and even 100%) sequence identity to SEQ ID NO: 17; a FabI having at least 90% (also at least 93%, 95%, 96%, 97%, 98%, 99% and even 100%) sequence identity to SEQ ID NO: 19; a FabZ having at least 90% (at least 93%, 95%, 96%, 97%, 98%, 99% and even 100%) sequence identity to SEQ ID NO: 21 and a FabB having at least 90% (at least 93%, 95%, 96%, 97%, 98% 99% and even 100%) sequence identity to SEQ ID NO: 27 and optionally one or more attenuated endogenous fad or fab genes selected from a gene encoding a FadE comprising at least 90% (at least 91%, 92%, 93%, 94%, 95%, 96%, 97%, 98% 99% and even 100%) sequence identity to SEQ ID NO: 14; a gene encoding a FadD comprising at least 90% (at least 91%, 92%, 93%, 94%, 95%, 96%, 97%, 98% 99% and even 100%) sequence identity to SEQ ID NO: 16; a gene encoding a FabF having at least 90% (also at least 93%, 95%, 96%, 97%, 98%, 99%) sequence identity to SEQ ID NO: 29; and/or a gene encoding a FadR comprising at least 90% (at least 91%, 92%, 93%, 94%, 95%, 96%, 97%, 98% 99% and even 100%) sequence identity to SEQ ID NO: 24. In some embodiments the polynucleotide encoding the FadE comprises a polynucleotide sequence comprising at least 95% sequence identity to SEQ ID NO: 13; the polynucleotide encoding the FadD comprises a polynucleotide sequence comprising at least 95% sequence identity to SEQ ID NO: 15: the polynucleotide encoding FabF comprises a polynucleotide sequence comprising at least 95% sequence identity to SEQ ID NO: 29 and the polynucleotide encoding the FadR comprises a polynucleotide sequence comprising at least 95% sequence identity to SEQ ID NO: 23.

7. Host Cells:

In some embodiments, the recombinant bacterial microorganism according to the invention is a Gram-positive, Gram negative and Gram-variable bacterial cell. In certain embodiments, host cells include, but are not limited to, species of a genus selected from the group consisting of *Agrobacterium, Arthrobacter, Bacillus. Clostridium, Corynebacterium, Escherichia, Erwinia, Geobacillus, Klebsiella, Lactobacillus, Mycobacterium, Pantoea, Rhodococcus, Rhotobacter, Streptomyces* and *Zymomonas*. In certain embodiments, the recombinant host cell is an industrial bacterial strain. Numerous bacterial industrial strains are known and suitable for use in the methods disclosed herein. In some embodiments, the bacterial host cell is a species of the genus *Bacillus*, e.g., *B. thuringiensis, B. anthracis, B. megalerium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans, B. subtilis. B. pumilus,* and *B. amyloliquefaciens*. In some embodiments, the bacterial host cell is a species of the genus *Erwinia*, e.g., *E. uredovora, E. carotovora, E. ananas, E. herbicola, E. punctata* and *E. terreus*. In other embodiments the bacterial host cell is a species of the genus *Pantoea*, e.g., *P. citrea* or *P. agglomerans*. In still other embodiments, the bacterial host cell is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans*. In further embodiments, the bacterial host cell is a species of the genus *Zymomonas*, e.g., *Z. mobilis* or *Z. lipolytica*. In further embodiments, the bacterial host cell is a species of the genus *Rhodococcus*, e.g. *R. opacus*.

In some embodiments, the bacterial host cell is a species of the genus *Escherichia*, e.g., *E. coli*. In various embodiments, the engineered *E. coli* bacterial strains useful in the processes described herein are derived from strain W3110, strain MG1655, strain B766 (*E. coli* W) and strain BW25113. In some further embodiments, the W3110 strain finds use in the present invention; the genome of this strain has been fully sequenced and annotated See e.g. Hayashi et al., (2005) Mol. Syst. Biol. 2:2006.0007). For industrial applications, phage-resistant strains are particularly useful. In this sense, deletion of the fhuA gene (also known as tonA) confers resistance to phages T1, T5 and phi80 (Link et al., 1997. J. Bact. 179: 6228-8237). Another useful strain is *E. coli* W (Archer et al. 2011, BMC Genomics. 12:9.doi: 10.1186/1471-2164-12-9). Also reference is made to Elben et al. (2005) J. of Food Protection 68(2):282-291.

Other examples of useful *E. coli* strains include, but are not limited to, *E. coli* strains found in the *E. coli* Stock Center from Yale University; the Keio Collection, available from the National BioResource Project at NBRP *E. coli*, Microbial Genetics Laboratory, National Institute of Genetics 1111 Yata, Mishima, Shizuoka, 411-8540 Japan; or strains deposited at the American Type Culture Collection (ATCC).

In some embodiments, the host cell is an *E. coli* cell that has been transformed with a polynucleotide sequence encoding a FAR, a FabH and optionally a FabD, FabF, FabG, FabI, FabZ and/or FabB as described herein. The polynucleotides encoding each of these enzymes may be located on the same vector or they may be located on different vectors. In some embodiments, the introduced genes are chromosomally integrated into the host genome. In some embodiments, the recombinant *E. coli* comprises a heterologous TE as described above. In some of the embodiments, the recombinant *E. coli* produces a fatty alcohol composition having at least 60% (e.g., at least 65%, at least 70%, at least 75%, at least 80%, at least 85%, at least 90% and at least 95%) of any one of C12, C14, C16 fatty alcohols or combinations thereof.

8. Fermentation/Culturing:

Any suitable means for culturing the recombinant host cells finds use in the present invention. Indeed, any suitable fermentation protocol finds use in the production of the fatty alcohols provided herein. In some embodiments, fermentation of the recombinant host cells as described hereinabove for example comprises fermenting bacterial host cells such as E. coli comprising: a heterologous polynucleotide encoding a FAR enzyme, a heterologous polynucleotide encoding an FabH enzyme; optionally a heterologous (introduced) polynucleotide encoding a Fab enzyme selected from a FabD, FabG, FabI, FabZ and/or FabB and variants and functional fragments thereof as described above; and optionally further comprising an inactivated fadE, an inactivated fadD, an inactivated fabF, and/or an inactivated fadR gene, under suitable conditions and for a time sufficient for production of fatty alcohols, as desired.

Conditions for the culture and production of cells, including bacterial, fungal and yeast cells, are readily available and well-known in the art. The engineered host cells can be cultured in conventional nutrient media modified as appropriate. Culture conditions, such as temperature, pH and the like, are those previously used with the host cell selected for expression, and will be apparent to those skilled in the art.

Cell culture media in general are set forth in Atlas and Parks (eds.) The Handbook of Microbiological Media (1993) CRC Press, Boca Raton, Fla. which is incorporated herein by reference. Additional information for cell culture is found in available commercial literature such as the Life Science Research Cell Culture Catalogue (1998) from Sigma-Aldrich, Inc (St Louis. MO) ("Sigma-LSRCCC") and, for example, The Plant Culture Catalogue and supplement (1997) also from Sigma-Aldrich, Inc (St Louis, Mo.) ("Sigma-PCCS"), all of which are incorporated herein by reference. Reference is also made to the Manual of Industrial Microbiology and Biotechnology. A. Demain and J. Davies Eds. ASM Press. 1999.

In some embodiments, the recombinant cells encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out at a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. Indeed, it is intended that any suitable fermentation temperature will be used in the present invention.

In some other embodiments, the fermentation is carried out for a period of time within the range of from about 8 hours to 240 hours, from about 8 hours to about 168 hours, from about 16 hours to about 144 hours, from about 16 hours to about 120 hours, or from about 24 hours to about 72 hours. Indeed, it is intended that any suitable fermentation time will find use in the present invention.

In some other embodiments, the fermentation will be carried out at a pH in the range of about 4 to about 8, in the range of about 4.5 to about 7.5, in the range of about 5 to about 7, or in the range of about 5.5 to about 6.5. Indeed, it is intended that any suitable pH range will find use in the present invention.

Carbon sources useful in the fermentation medium (e.g., broth) in which the recombinant microorganisms are grown are those that can be assimilated by the recombinant host strain. Such carbon sources are available in many forms and include renewable carbon sources, including but not limited to cellulosic and starch feedstock substrates obtained there from. Such examples include for example fermentable sugars such as monosaccharides, disaccharides, and short chain oligosaccharides (e.g., glucose, fructose, xylose, galactose, arabinose, maltose, mannose, and sucrose, fructo-oligosaccharide, galacto-oligosaccharide as well as numerous other sugars; it is not intended that the present invention be limited to any particular fermentable sugar). Other carbon sources include, but are not limited to saturated and unsaturated fatty acids, alcohols, glycerol, lactose, succinate, ketones, amino acids, acetate, gases (e.g., $CO_2$), and mixtures thereof.

In some embodiments, the assimilable carbon source is derived from biomass. The term "biomass" is broadly used herein to encompasses any living or dead biological material that contains a polysaccharide substrate, including but not limited to cellulose, starch, other forms of long-chain carbohydrate polymers, and mixtures of such sources. Examples of biomass include, but are not limited to, wood, wood pulp, paper pulp, corn fiber, grain, corn grain, corn cobs, sugar cane, sugar beet, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in alternative embodiments, the biomass comprises a mixture of fibers that originate from different biomasses. In some embodiments, the biomass may also comprise transgenic plants that express ligninase and/or cellulase enzymes (See e.g., US 2008/0104724 A1).

In some embodiments, the cellulosic feedstock useful as an assimilable carbon source has been derived from a biomass substrate that has been pretreated. Various pretreatment methods are known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof. The pretreatment increases the susceptibility of cellulose to hydrolysis. In some embodiments, the substrate is slurried prior to pretreatment. The following references described various means of pretreatment. Steam explosion performing acid pretreatment of biomass substrates is described in U.S. Pat. No. 4,461,648. Also reference is made to WO2010/112129; WO2012/042545 and WO2012/0425544. Continuous pretreatment using a slurry is described U.S. Pat. No. 7,754,457. Methods of alkali pretreatment is such as Ammonia Freeze Explosion, Ammonia Fiber Explosion or Ammonia Fiber Expansion ("AFEX") are described in U.S. Pat. Nos. 5,171,592; 5,037,663; 4,600,590; 6,106,888; 4,356,196; 5,939,544; 6,176.176; 5,037,663 and 5,171,592. Alternative methods to AFEX utilizing a dilute ammonia pretreatments are described in WO2009/045651 and US 2007/0031953. Chemical pretreatments with organic solvents are disclosed in U.S. Pat. No. 4,556,430. Other pretreatments methods are disclosed in U.S. Pat. No. 7,465,791; PCT publication WO2011/028554, and Weil et al. (1997) Appl. Biochem. Biotechnol., 68(1-2): 21-40 [1997].

9. Production of Fatty Alcohols:

In some embodiments, the invention is directed to a method of producing fatty alcohols from the engineered cells, wherein the engineered cells comprise a recombinant FAR polynucleotide, an introduced polynucleotide encoding a FabH, and optionally a polynucleotide encoding one or more of i) a heterologous TE, ii) an introduced FadD, iii) an introduced FabI, iv) an introduced FabA, and v) an introduced FabZ as described more specifically herein.

In various embodiments, fatty alcohols produced by the methods of the invention are further recovered or isolated (for example from the cell culture). Recovery or isolation of the produced fatty alcohols refers to substantially separating the fatty alcohols from other components of the culture medium or fermentation process. Recovery or isolation may be accomplished by solvent extraction of the aqueous nutrient medium with a suitable water immiscible solvent. Extraction may occur simultaneously with fatty alcohol production and in some embodiments, extraction is continuous. Phase separation followed by solvent removal provides the fatty alcohol which may then be further purified and fractionated using methods and equipment known in the art. In some other aspects of the invention, the secreted fatty alcohols coalesce to form a water immiscible phase that can be directly separated from the aqueous nutrient medium either during the fermentation process or after its completion.

In certain embodiments of the invention, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the fatty alcohols produced by the methods described herein are secreted into the culture medium by the recombinant host cells.

In certain embodiments, fatty alcohols are isolated by separating the host cells from the aqueous nutrient medium, for example by centrifugation, resuspension and extraction of the fatty alcohols from the recombinant host cells using an organic solvent or solvent mixture. Suitable protocols for recovering fatty alcohols from recombinant host cells and/or culture medium are known to the skilled artisan. In some embodiments, fatty alcohols may be recovered by first lysing the cells to release the fatty alcohols and then extracting the fatty alcohol from the lysate using conventional means. Reference is also made to Yeast Protocols Handbook, (2009) Clontech Laboratories, Inc. A Takara Bio Company, Mt. View Calif. 94043; PNAS 2003 Vol. 100, 16:9156-9161: and Doan et al., (2009) J. Plant Physiol. 166: 787-796 which discloses methods to isolate and measure fatty alcohols produced in E. coli using FARs from Arabidopsis. Indeed, it is intended that any suitable method will find use in the present invention and it is not intended that the present invention be limited to any particular method(s) for separating host cells from the nutrient medium.

In various embodiments, the compositions produced by the methods and microorganisms described herein comprise both saturated and unsaturated fatty alcohols. In certain embodiments, the unsaturated fatty alcohols are mono-unsaturated fatty alcohols. In some embodiments, the fatty alcohol compositions comprise both saturated and unsaturated fatty alcohols, and the amount of unsaturated fatty alcohols compared to saturated fatty alcohols in the total fatty alcohol composition is less than about 40%, less than about 35%, less than about 30%, less than about 20%, less than about 15%, less than about 10%, less than about 5%, or less than about 1% of the fatty alcohols present in the composition.

In some embodiments, the fatty alcohol compositions comprise both saturated and unsaturated fatty alcohols. In some embodiments, the percentage of saturated fatty alcohols in the fatty alcohol compositions produced by the engineered bacterial cells encompassed by the invention is greater than about 50%, greater than about 55%, greater than about 60%, greater than about 65%, greater than about 70%, greater than about 75%, greater than about 80%, greater than about 85%, greater than about 90%, greater than about 95%, or greater than about 97%.

In some embodiments, the fatty alcohol compositions produced by the methods and engineered microorganisms described herein comprise one or more alcohols selected from 1-decanol (C10:0). 1-dodecanol (C12:0), 1-tetradecanol (C14:0), 1-hexadecanol (C16:0), and 1-octadecanol (C18:0).

In some typical embodiments, C10 to C18 fatty alcohols comprise at least about 90%, at least about 95%, at least about 96%, at least about 97%, at least about 98%, or at least about 99% by weight of the total fatty alcohols produced by the recombinant host cells. In some embodiments, C12 to C16 fatty alcohols comprise at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, or at least about 98% by weight of the total fatty alcohols produced by the recombinant host cells. It is understood that a reference to a "Cx fatty alcohol" (e.g., C12) includes both saturated and unsaturated fatty alcohols having "x" carbon atoms unless indicated otherwise.

In certain embodiments, C14 to C16 fatty alcohols comprise at least about 60%, at least about 65%, at least about 70%, at least about 75%, at least about 80%, at least about 85%, at least about 90%, at least about 92%, at least about 95%, at least about 97%, or at least about 99% by weight of the total produced fatty alcohols.

In certain embodiments, C12 to C14 fatty alcohols comprise at least about 50%, at least 55%, at least 60%, at least about 65%, at least about 70%, at least about 75%, at least about 80%, at least about 85%, at least about 90%, at least about 92%, at least about 95%, at least about 97%, or at least about 99% by weight of the total produced fatty alcohols.

In some typical embodiments, C10:0 to C18:0 fatty alcohols comprise at least about 80%, at least about 85%, at least about 90%, at least about 95%, at least about 96%, at least about 97%, at least about 98%, or at least about 99% by weight of the total produced fatty alcohols. In some embodiments, C12:0 to C16:0 fatty alcohols comprise at least about 75%, at least about 80% at least about 85%, at least about 90%, at least about 92%, at least about 93%, at least about 94%, at least about 95%, or at least about 98% by weight of the total produced fatty alcohols. In certain embodiments. C14:0 to C16:0 fatty alcohols comprise at least about 70%, at least about 75%, at least about 80%, at least about 85%, at least about 90%, at least about 92%, at least about 95%, at least about 97%, or at least about 99% by weight of the total produced fatty alcohols.

In certain embodiments, C12:0 to C14:0 fatty alcohols comprise at least about 60%, at least about 65%, at least about 70%, at least about 75%, at least about 80%, at least about 85%, at least about 90%, at least about 92%, at least about 95%, at least about 97%, or at least about 99% by weight of the total produced fatty alcohols.

The proportions of saturated and unsaturated fatty alcohols produced by the strains may be calculated after quantifying all the fatty alcohol species using any suitable method known in the art (e.g. GC-FID as described in US 2011/0000125SA1). The saturated fraction represents the sum of all C12:0-OH; C14:0-OH; C16:0-OH and C18:0-OH. While the unsaturated fraction is composed of the sum of C12:1-OH: C14:1-OH: C16:1-OH and C18:1-OH.

In some embodiments, the fatty alcohol compositions produced by the recombinant cells comprise a % of saturated fatty alcohols that is greater than about 55%; greater than about 60%; greater than about 65%; greater than about 70%; greater than about 75%; greater than about 80%; greater than about 85%; greater than about 90%; greater than about 95%; or greater than about 97%. In some additional embodiments, the fatty alcohol compositions further comprise at least about 85%, at least about 88%, at least about 90%, at least about 91%, at least about 92%, at least about 93%, at least about 94%, at least about 95%, at least about 96%, at least about 97%, or at least about 98% C12 to C16 fatty alcohols. In some additional embodiments, the fatty alcohol compositions further comprise at least about 85%, at least about 88%, at least about 90%, at least about 91%, at least about 92%, at least about 93%, at least about 94%, at least about 95%, at least about 96%, at least about 97%, or at least about 98% C12 to C14 fatty alcohols.

In some embodiments, the methods encompassed by the invention produce fatty alcohol compositions having a carbon chain length profile that has shifted from the carbon chain length profile of a corresponding host cell. In some embodiments, the composition of C12 fatty alcohols has been increased by greater than 25%, greater than 30%, greater than 35%, greater than 40%, greater than 50%, greater than 60% and even greater than 70%, and at the same time the composition of C16 fatty alcohols produced from the same engineered cells has been decreased by at least 10%, by at least 15%, by at least 20%, by at least 25% and by at least 30%. In some embodiments, the composition of C16 fatty alcohols produced from the same engineered cells has been decreased by at least 10%, by at least 15%, by at least 20%, by at least 25% and by at least 30% as compared to a corresponding host cell. In some embodiments, the engineered cells producing fatty alcohol compositions comprising a shift in the percent of C12 and C16 fatty alcohols comprise an engineered cell comprising a polynucleotide encoding a FAR comprising at least 90% (at least 95%, 96%, 97%, 98% or 99%) sequence identity to SEQ ID NO:2, SEQ ID NO: 4, SEQ ID NO: 6 or SEQ ID NO: 8 and comprise an introduced polynucleotide encoding a FabH comprising at least 80% (at least 85%, at least 88%, at least 90%, at least 92%, at least 95%, at least 97%, at least 98%, at least 99% and even 100% sequence identity to SEQ ID NO: 10 as compared to a corresponding engineered cell transformed to include only the polynucleotide encoding the FAR comprising at least 90% (at least 95%, 96%, 97%, 98% or 99%) sequence identity to SEQ ID NO:2, SEQ ID NO: 4, SEQ ID NO: 6 or SEQ ID NO: 8.

In certain preferred embodiments, the methods encompassed by the invention produce fatty alcohol compositions having a carbon chain length profile that has shifted from the carbon chain length profile of a corresponding host cell wherein the composition of C12 fatty alcohols has increased by greater than 30%, by greater than 40%, greater than 50%, greater than 60% and even greater than 70%, and at the same time the composition of C16 fatty alcohols produced from the same engineered cells has been decreased by at least 20% and the engineered cells producing the fatty alcohol compositions comprising a shift in the percent of C12 and C16 comprise a polynucleotide encoding a FAR comprising at least 95% sequence identity to SEQ ID NO:2, SEQ ID NO: 4, SEQ ID NO: 6 or SEQ ID NO: 8 and comprise an introduced polynucleotide encoding a FabH comprising at least 90%, sequence identity to SEQ ID NO: 10 and optionally include a) a polynucleotide encoding an introduced TE (e.g., a TE having at least 90% sequence identity to SEQ ID NO: 12 or SEQ ID NO: 63 and a polynucleotide encoding an introduce FadD (e.g., a FadD having at least 90% sequence identity to SEQ ID NO: 16 or b) a polynucleotide encoding an introduced FabI (e.g., a FabI having at least 90% sequence identity to SEQ ID NO: 20; c) a polynucleotide encoding an introduced FabZ (e.g., having at least 90% (at least 95%, at least 98% and even 100%) sequence identity to SEQ ID NO: 22), d) a polynucleotide encoding an introduced FabD (e.g., having at least 90% (at least 95%, at least 98% and even 100%) sequence identity to SEQ ID NO: 26); and/or a e) polynucleotide encoding an introduced FabG (e.g. having at least 90%, at least 95%, at least 98% and even 100%) sequence identity to SEQ ID NO: 18) as compared to a corresponding engineered cell transformed to include only the polynucleotide encoding the FAR comprising at least 95% sequence identity to SEQ ID NO:2, SEQ ID NO: 4. SEQ ID NO: 6 or SEQ ID NO: 8.

In certain embodiments, the amount of fatty alcohols produced by the recombinant bacterial cells according to the methods described herein comprise saturated and/or unsaturated C8 to C18 alcohols in a range of about 10 mg/L to about 150 g/L of aqueous nutrient medium, such as in a range of about 10 mg/L to about 125 g/L, about 10 mg/L to about 100 g/L, about 10 mg/L to about 75 g/L, about 10 mg/L to about 50 g/L, about 10 mg/L to about 25 g/L, about 10 mg/L to about 5 g/L or in a range of about 10 mg/L to about 2 g/L of medium, using routine modification of culturing conditions. In some embodiments, the amount of fatty alcohols produced by the methods described herein is at least about 0.5 g/L, at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, or at least about 10 g/L of medium. In various embodiments, the amount of fatty alcohols produced by the methods described herein is at least about 20 g/L, at least about 30 g/L, at least about 40 g/L, or at least about 50 g/L of medium. In some embodiments, a recombinant bacteria (e.g., E. coli) encompassed by the invention produces C12 to C16 fatty alcohols in an amount of at least about 1.0 g/L, at least about 5.0 g/L, at least about 10 g/L, at least about 15 g/L, at least about 20 g/L, at least about 25 g/L, or at least about 30 g/L of medium. One method to extract and quantify fatty alcohols is provided in US Patent Application 2011/0000125. However, it is not intended that the present invention be limited to any particular method(s) for extracting and/or quantifying the fatty alcohols produced using the present invention, as any suitable methods find use.

In some embodiments, the amount of fatty alcohols produced by the methods described herein are in at least about 100 mg/g, at least 500 mg/g, at least 1 g/g, at least 2 g/g, at least 5 g/g/at least 6 g/g, at least 7 g/g, at least 8 g/g/at least 9 g/g/at least 10 g/g/at least 12 g/g at least 15 g/g of dry cell weight. In some embodiments the amount of fatty alcohols produced by the methods described herein are in the range of about 100 mg/g to about 15 g/g of dry cell weight and also in the range of about 100 mg/g to about 10 g/g of dry cell weight. In other embodiments, the amount of fatty alcohols produced by the methods described herein is in the range of about 1 g/g to about 12 g/g; about 1 g/g to about 10 g/g; about 1 g/g/to about 5 g/g of dry cell weight, and about 5 g/g to about 10 g/g of dry cell weight.

In certain embodiments, the amount of fatty alcohols produced by the methods described herein is in the range of about 10% to about 20% of dry cell weight, about 20% to about 30% of dry cell weight, about 30% to about 40% of dry cell weight, about 40% to about 50% of dry cell weight, about 50% to about 60% of dry cell weight, about 60% to about 70% of dry cell weight, or about 70% to about 80% of dry cell weight.

In some embodiments, the fatty alcohol compositions produced by the engineered cells and methods described herein may also comprise fatty acid-derived components. Fatty acid derivative compounds include compounds such as but not limited to esters (e.g. acetyl, methyl or ethyl esters and waxes) and fatty acids.

10. Compositions:

In yet another aspect, the present invention relates to the use of the engineered microorganisms as described herein for the production of various compositions, including but not limited to, fuel compositions (e.g., biodiesels and petrodiesels), cleaning compositions including detergent compositions (e.g., laundry detergents in liquid gel, spray, and powder form, hard surface cleaners, dishwashing detergents, and the like); industrial compositions (e.g., lubricants, solvents, and industrial cleaners); and personal care compositions (e.g., soaps, cosmetics, shampoos, gels, etc.).

Detergent Compositions

In some embodiments, the fatty alcohol compositions described herein, and compounds derived there from, can be used as components of detergent compositions. Detergent compositions comprising fatty alcohols and fatty alcohol derivatives produced by the methods of the present invention include compositions used in cleaning applications, including, but not limited to, laundry detergents, hand-washing agents, dishwashing detergents, rinse-aid detergents, household detergents, and household cleaners, in liquid, gel, granular, powder, or tablet form. In some embodiments, the fatty alcohols produced by the methods described above are used directly in detergent compositions. In some embodiments, the fatty alcohols and fatty alcohol derivatives are reacted with a sulfonic acid group to produce sulfate derivatives that can be used as components of detergent compositions. In some embodiments, the fatty alcohols and fatty alcohol derivatives are reacted with an ethylene oxide to produce ethoxylated derivatives that can be used as components of detergent alcohols. Detergent compositions that can be generated using the fatty alcohols and fatty alcohol derivatives produced by the methods of the present invention include, but are not limited to, hair shampoos, rinses, and conditioners for humans and other animals, carpet shampoos, hard surface cleaners, light-duty household cleaners, light-duty household detergents, heavy-duty household cleaners, and heavy-duty household detergents. Detergent compositions generally include, in addition to fatty alcohols and derivative thereof, one or more builders (e.g., sodium carbonate, complexation agents, soap, and zeolites), enzymes (e.g., proteases, lipases, cellulases, and/or amylases); carboxymethyl cellulose, optical brighteners, fabric softeners, colourants and perfumes (e.g. cyclohexyl salicylate). Indeed, it is not intended that the present invention be limited to any particular detergent, detergent formulation, nor detergent use.

In some embodiments, sulfate derivatives and/or ethoxylated derivatives (e.g., C12-15) derived from fatty alcohols are used in products such as hair shampoos, carpet shampoos, light-duty household cleaners, and light-duty household detergents. In some embodiments, sulfate derivatives and/or ethoxylated derivatives (e.g., C16-C18) derived from fatty alcohols are used in products such as hair shampoos and conditioners. In some embodiments, sulfate derivatives and/or ethoxylated derivatives (e.g. C16-18) derived from fatty alcohols are used in products such as heavy-duty household cleaners and heavy-duty household detergents. Indeed, it is not intended that the present invention be limited to any particular detergent, detergent formulation, nor detergent use.

Personal Care Compositions

In some embodiments, fatty alcohol compositions as described herein, and compounds derived there from, are used as components in personal care compositions. In some embodiments, the fatty alcohols produced by the methods described above are used directly in personal care compositions. Personal care compositions containing fatty alcohols or fatty alcohol derivatives produced by the methods of the present invention include compositions used for application to the body (e.g., for application to the skin, hair, nails, or oral cavity) for the purposes of grooming, cleaning, beautifying, or caring for the body, including but not limited to lotions, balms, creams, gels, serums, cleansers, toners, masks, sunscreens, soaps, shampoos, conditioners, body washes, styling aids, and cosmetic compositions (e.g., makeup in liquid, cream, solid, anhydrous, or pencil form).

In some embodiments, the fatty alcohols or fatty alcohol derivatives can be reacted with a sulfonic acid group to produce sulfate derivatives that can be used as components of said compositions. In some embodiments, the fatty alcohols and fatty alcohol derivatives are reacted with an ethylene oxide to produce ethoxylated derivatives that can be used as components of said compositions. In some embodiments, sulfate derivatives (e.g., C12 to 14) derived from the fatty alcohol compositions produced by the methods described herein are used in products such as toothpastes. Indeed, it is not intended that the present invention be limited to any particular formulation, nor use.

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. Indeed, it is not intended that the present invention be limited to any particular formulation, nor use.

Other Compositions:

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. In some embodiments, sulfate derivatives (e.g., C12 to C14) derived from the fatty alcohol compositions produced by the methods described herein are used in products such as toothpastes.

In some instances, fatty alcohols (especially cetyl alcohol, stearyl alcohol and myristyl alcohol) may be used as food additives (e.g., adjuvants and production aids).

Alkane and/or Alkene Compositions

In some embodiments, fatty alcohols produced according to the methods described herein can be reduced to yield alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein.

Any suitable method known in the art can be used to reduce the fatty alcohols. In some embodiments, reduction of fatty alcohols is carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See Li et al., 2007, *Modern Organic Synthesis in the Laboratory*, p. 81-83. In another embodiment, alkanes are produced by hydrogenation of fatty alcohols.

The alkanes can be isolated from the reaction mixture (which may contain unreduced fatty alcohols) to yield a composition comprising substantially all alkanes Alternatively, the alkanes and un-reduced fatty alcohols can be isolated from the reaction mixture to yield a composition comprising alkanes and fatty alcohols. In some embodiments, the fatty alcohol compositions comprise at least about 10%, at least about 20%, at least about 30%, at least about 40%, at least about 50%, at least about 60%, at least about 70%, at least about 80%, at least about 85%, at least about 90%, at least about 92%, at least about 95%, at least about 96%, at least about 97%, at least about 98%, or at least about 99% alkanes by weight of the composition after reduction. In some embodiments, the alkane is octane, decane, dodecane, tetradecane, hexadecane, octadecane, icosane, docosane, tetracosane, or mixtures thereof.

Ester Compositions:

In other embodiments, fatty alcohols are reacted with a carboxylic acid to form acid esters. Esterification reactions of fatty alcohols are well-known in the art. In certain embodiments, the transesterification reaction is carried out in the presence of a strong catalyst, e.g., a strong alkaline such as sodium hydroxide. In other embodiments, the esterification reaction is carried out enzymatically, using an enzyme that catalyzes the conversion of fatty alcohols to acid esters, such as lipoprotein lipase. See, e.g., Tsujita et al., 1999, "Fatty Acid Alcohol Ester-Synthesizing Activity of Lipoprotein Lipase" *J. Biochem.* 126:1074-1079.

The following examples are offered to illustrate, but not to limit, the claimed invention.

EXAMPLES

The present invention is described in further detail in the following Examples, which are not in any way intended to limit the scope of the invention as claimed. In the experimental disclosure below, the following abbreviations apply: ppm (parts per million); M (molar); mM (millimolar), uM and μM (micromolar); nM (nanomolar); mol (moles): gm and g (gram); mg (milligrams): ug and μg (micrograms); L and l (liter): ml and mL (milliliter); cm (centimeters); mm (millimeters); um and μm (micrometers); sec. (seconds); min(s) (minute(s)); h(s) (hour(s)); U (units); LB (Luria-Bertani); MW (molecular weight); rpm (rotations per minute); ° C. (degrees Centigrade); wt % (weight percent); w.r.t. (with regard to); Δ (deletion); DNA (deoxyribonucleic acid); PCR (polymerase chain reaction); _F (forward primer); _R (reverse primer); (RNA (ribonucleic acid); gDNA (genomic DNA): cDNA (complementary DNA); PCR (polymerase chain reaction): rbs (ribosome binding sequence); Sigma (Sigma Aldrich, St. Louis, Mo.); Qiagen (Qiagen, Inc., Valencia, Calif.); Invitrogen (Invitrogen, Corp., Carlsbad, Calif.); and Promega (Promega. Corp., Madison, Wis.).

Example 1

Construction of Plasmid pLS8379

To overproduce the FAR enzyme having SEQ ID NO: 6 or 8 in *E. coli*, a low copy vector carrying the Trc promoter was constructed. A DNA fragment containing the lacIq gene, the Trc promoter, and the multiple cloning sites present in pTrcHis2-B (Invitrogen, Carlsbad, Calif.) was PCR amplified using the primers:

1920TrcM_F (SEQ ID NO: 31)
5'-GACCTTAAAACCCTAAAGGCTTAAGGGCATCCGCTTA

CAGACA
and

1920TrcM_R (SEQ ID NO: 32)
5'-GGAGAAAATACCGCATCAGGCGCCTCAGGAGAGCGTT

CACCGAC.

The PCR reaction was carried out using the enzyme Phusion (New England BioLabs, Ipswich, Mass.) with an initial denaturation step at 98° C. for 30 sec, followed by 25 cycles of the steps: 98° C. for 10 sec; 65° C. for 15 sec and 72° C. for 15 sec. This was followed by a final elongation step at 72° C. for 5 min. The primers used for this PCR reaction carry regions of homology to plasmid pCL1920, and therefore the PCR product described above can be used as a megaprimer to amplify a defined region of pCL1920 (Lerner and Inouye (1990) NAR 18: 4631) which contains the pSC101 origin of replication and confers resistance to Spectinomycin (GenBank: AB236930). This PCR reaction was carried out using the Pfu Ultra enzyme (Agilent Technologies, Santa Clara, Calif.) with an initial denaturation step at 95° C. for 2 min, followed by 16 cycles of the steps: 95° C. for 30 sec; 55° C. for 30 sec and 68° C. for 7 min. This was followed by a final elongation step at 68° C. for 7 min. The outcome of the second PCR reaction was sequence-verified and the resulting plasmid was named pLS8379 (SEQ ID NO: 59).

Example 2

Construction of pCDX11

The $P_{TRC}$ promoter present in pLS8379 was replaced with a synthetic DNA fragment containing a $P_{TRC}$ variant where a symmetrical Lac operator (Sadler et al., 1983. PNAS. 80:6785-6789) was introduced upstream of the −35 region of $P_{TRC}$. This promoter was synthesized as an EcoRV-NcoI DNA fragment (GeneScript, Piscataway, N.J.) having the sequence (SEQ ID NO: 64)
GATATCTCGGTAGTGGGATACGACGATACCGAAGACAGCTCATGTTAT

ATCCCGCCGTTAACCACCATCAAACAGGATTTTCGCCTGCTGGGGCAA

ACCAGCGTGGACCGCTTGCTGCAACTCTCTCAGGGCCAGGCGGTGAAG

GGCAATCAGCTGTTGCCCGTCTCACTGGTGAAAAGAAAAACCACCCTG

GCGCCCAATACGCAAACCGCCTCTCCCCGCGCGTTGGCCGATTCATTA

ATGCAGCTGGCACGACAGGTTTCCCGACTGGAAAGCGGGCAGTAATAA

TTTAAATTGGTTTGACAGCTTATCATCGACTGCACGGTGCACCAATGC

TTCTGGCGTCAGGCAGCCATCGGAAGCTGTGGTATGGCTGTGCAGGTC

GTAAATCACTGCATAATTCGTGTCGCTCAAGGCGCACTCCCGTTCTGG

ATAATGTTTTTTGCGCCGACATAATTGTGAGCGCTCACAATTTCTGAA

ATGAGCTGTTGACAATTAATCATCCGGCTCGTATAATGTGTGGAATTG

TGAGCGGATAACAATTTCACACAGGAAACAGCGCCGCTGAGAAAAAGC

GAAGCGGCACTGCTCTTTAACAATTTATCAGACAATCTGTGTGGGCAC

TCGACCGGAATTATCGATTAACTTTATTATTAAAAATTAAAGGAGGAA

TAAACCATGG and used to replace the EcoRV-NcoI region from pLS8379 previously cut with the same restriction enzymes. A ligation reaction containing the two DNA fragments was incubated overnight at 16° C. and then transformed into E. coli Top 10 electrocompetent cells (Invitrogen, Carlsbad, Calif.) following the manufacturer's protocols. Cells were plated on LB agar plates containing 100 micrograms/ml of Spectinomycin. Plates were incubated overnight at 37° C. Obtained clones were sequence verified.

Example 3

Construction of pCDX11-7076 Plasmid

The plasmid pCDX11-FAR comprising the FAR-V2 polynucleotide of SEQ ID NO:5 encoding the FAR-V2 enzyme having the amino acid sequence of SEQ ID NO:6 is designated pCDX11-7076 and was constructed as described below. A DNA fragment containing the FAR-V2 gene was PCR amplified using the primers:

(SEQ ID NO: 33)
7076_NcoI_F
5' TAAACCATGGCGACTCAACAACAGAACA
and (SEQ ID NO: 34)
7076_SalI_R
5' CTATGTCGACTTAGGCGGTTTTATCGTCAGTATCA.

The restriction enzyme sites NcoI and SalI were incorporated into 7076_NcoI_F and 7076_SalI_R respectively, allowing ligation into pCDX 11 digested with NcoI and SalI. Ligation reactions were incubated overnight at 16° C. and then transformed into E. coli TOP 10 chemically competent cells (Invitrogen, Carlsbad, Calif.) using standard techniques. Cells were plated on LB agar plates containing 100 ug/ml of Spectinomycin and incubated overnight at 37° C. Obtained clones were sequence verified. The cycling conditions and reactions were applied according to the manufacturers' instructions.

Example 4

Construction of pCDX11-7076-FabH Plasmid

Two different plasmids were assembled comprising the polynucleotides encoding FAR-V2 and FabH; pCDX11-7076-rbsH-FabH and pCDX11-7076-rbsA-FabH. The plasmid pCDX11-7076 was digested with enzymes SalI and PmeI (New England BioLabs, Ipswich, Mass.) following manufacturer recommendations and a synthetic linker containing a multicloning site ("MCS") was ligated into this vector to facilitate further cloning.

pCLlinker_F (SEQ ID NO: 35)
5' TCGACATAGATCTAGAACTTACTCGGAAGCTTCTTA

ATTAAGAGGATCCATTGACGTCTATGAATTCGTTT-3'
and

```
pCLlinker_R
                                          (SEQ ID NO: 36)
5' AAACGAATTCATAGACGTCAATGGATCCTCTT

AATTAAGAAGCTTCCGAGTAAGTTCTAGATCTATG-3'.
```

After ligation the obtained plasmid pCDX11-7076 was sequence verified.

The *E. coli* fabH gene was PCR amplified from genomic DNA isolated from *E. coli* strain W3110 using primers SalI-rbsH-fabH_F and BamHI-fabH_R.

```
SalI-rbsH-fabH_F
                                          (SEQ ID NO: 37)
5'-AAAAGTCGACAACCGAAAAGTGACTGAG CGTACATGTATACGA AGATTATTGGTACTGGC-3'
and BamHI-fabH_R
                                          (SEQ ID NO: 38)
5'-AAAAGGATCCTTAGAAACGAACCAGCGCGG-3'.
```

Primer SalI-rbsH-fabH_F was designed to add the 23 base pair RBS region from the fabH gene ("rbsH") and primer BamHI-fabH_R was designed to replace the normal TAG stop codon of fabH with the TAA stop codon. Additionally, the *E. coli* fabH gene was PCR amplified from genomic DNA isolated from *E. coli* strain W3110 using primers SalI-rbsA-fabH_F and BamHI-fabH_R.

```
SalI-rbsA-fabH_F
                                          (SEQ ID NO: 39)
5' AAAA GTCGACATAAAATAAGGC TTACAGAGAACATGTATACGAA GATTATTGGTACTGGC-3'
and BamHI-fabH_R
                                          (SEQ ID NO: 40)
5'AAAAGGATCCTTAGAAACGAACCAGCGCGG-3'.
```

Primer SalI-rbsA-fabH_F was designed to add the 23 base pair RBS region from the fabA gene ("rbsA") and primer BamHI-fabH_R was designed to replace the normal TAG stop codon of fabH with the TAA stop codon.

The PCR reactions were carried out using the enzyme Phusion (New England BioLabs, Ipswich, Mass.) with an initial denaturation step at 98° C. for 30 sec, followed by 30 cycles of the steps: 98° C. for 5 sec; 63° C. for 20 sec and 72° C. for 30 sec. This was followed by a final elongation step at 72° C. for 5 min. After the PCR reaction, the PCR products were purified through a purification column and eluted with water.

Both PCR products (SalI-rbsH-fabH-BamHI and SalI-rbsA-fabH-BamHI) and the plasmid (pCDX11-7076) were digested with the restriction enzymes SalI and BamHI (New England BioLabs, Ipswich, Mass.) following manufacturer recommendations. The plasmid and inserts were ligated using Quick Ligase (New England BioLabs, Ipswich, Mass.) following manufacturer recommendations and the resulting products were transformed into *E. coli* TOP 10 electrocompetent cells (Invitrogen, Carlsbad, Calif.) using standard techniques. Cells were plated on LB agar plates containing 100 ug/ml of Spectinomycin and incubated overnight at 37° C. Obtained clones were sequence verified.

Example 5

Construction of pCK900-FadD-TE Plasmid

The plasmid pCK900-FadD-TE comprising a polynucleotide (SEQ ID NO: 11) encoding an acyl-ACP thioesterase from *Umbellularia californica* having the amino acid sequence of SEQ ID NO: 12 and a polynucleotide (SEQ ID NO: 15) encoding a FadD enzyme having the amino acid sequence of SEQ ID NO: 16 was constructed by cloning fadD and TE into pCK110900-i-bla plasmid (denoted pCK900-I. The native *E. coli* fadD gene (SEQ ID NO: 15) was PCR amplified using the primers:

```
oKC221 fadD_SfiI_F
                                          (SEQ ID NO: 41)
TAGAGGCCAGCCTGGCCATAAGGAGATATACATATGA AGAAGGTTTG GCTTAACCGTTAT
and oKC222 fadD_BTE1_R
                                          (SEQ ID NO: 42)
CGGTTTTGGTTTCCACTCTAACATGGTTTATTCCTCCTTTCATTAGGC

TTTATTGTCCACTTTG.
```

The polynucleotide sequence of TE (SEQ ID NO:11) was synthesized by GenScript (Piscataway, N.J.) and the synthesized gene was PCR amplified using the primers:

```
oKC223 fadD_TE1_F
                                          (SEQ ID NO: 43)
CAAAGTGGACAATAAAGCCTAATGAAAGGAGGAATAAA CCATGTTAGAGTGGAAACCAAAACCG
and oKC224 TE_SfiI_R
                                          (SEQ ID NO: 44)
TGGTGGCCAGTTTGGCCTTATACCCGCGGCTCGGCCGG

AAT.
```

SfiI restriction sites were incorporated into the design of oKC221 and oKC224. Primers oKC222 and oKC223 provided a region of overlap between the two PCR products that allowed for their combination into a single larger product housing both genes in a subsequent PCR reaction. The final PCR product and pCK900-1 were digested with SfiI restriction enzyme (New England Biolabs, Ipswich, Mass.) and ligated together using T4 DNA Ligase (New England Biolabs) followed by transformation into *E. coli* TOP 10 chemically competent cells (Life Technologies, Carlsbad, Calif.) following the manufacturer's instructions. Tranformants were selected on LB agar plates supplemented with 100 ug/ml spectinomycin and incubated overnight at 37° C. Clones were sequence verified.

Example 6

Construction of pCDX11-8087 Plasmid

The plasmid pCDX11-FAR comprising the FAR-V3 polynucleotide of SEQ ID NO:7 encoding the FAR-V3 enzyme having the amino acid sequence of SEQ ID NO:8 is designated pCDX11-8087 and was constructed as described below. A DNA fragment containing the FAR-V3 gene was PCR amplified using the primers:

```
8087_NcoI_F
                                          (SEQ ID NO: 45)
5'-TAAACCATGGCGACTCAACAACAGAACA
and 8087_SalI_R
                                          (SEQ ID NO: 46)
5'-CTATGTCGACTTAGGCGGTTTTATCGTCAGTATCA.
```

The restriction enzyme sites NcoI and SalI were incorporated into 8087_NcoI_F and 8087_SalI_R respectively, allowing ligation into pCDX11 (See, example 3) digested with NcoI and SalI. Ligation reactions were incubated overnight at 16° C. and then transformed into *E. coli* TOP 10 chemically competent cells (Invitrogen, Carlsbad, Calif.) using standard techniques. Cells were plated on LB agar plates containing 100 ug/ml of Spectinomycin and incubated overnight at 37° C. Obtained clones were sequence verified. The cycling conditions and reactions were applied according to the manufacturers' instructions, unless otherwise specified.

Example 7

Construction of pCDX11-8087-rbsA-FabH Plasmid

The plasmid pCDX11-8087-rbsA-FabH was constructed as described below. The FAR-V3 gene was amplified from pCDX11-8087 using the primers 8379_Fwd and 8379 Rev:

```
8379_F
                                          (SEQ ID NO: 47)
5'-TGTGGAATTGTGAGCGGATA-3'
and 8379_R
                                          (SEQ ID NO: 48)
5'-CGCTTCTGCGTTCTGATTT-3'.
```

The PCR reactions were carried out using the enzyme Phusion (New England BioLabs, Ipswich, Mass.) with an initial denaturation step at 98° C. for 30 sec, followed by 30 cycles of the steps: 98° C. for 5 sec; 63° C. for 20 sec and 72° C. for 30 sec. This was followed by a final elongation step at 72° C. for 5 min. After the PCR reaction, the PCR product was purified through a PCR purification column and eluted with water.

The FAR-8087 PCR product from above and the plasmid pCDX11-7076-rbsA-fabH were digested with the restriction enzymes ClaI and SalI (New England BioLabs, Ipswich, Mass.) following manufacturer recommendations. The plasmid and inserts were ligated using Quick Ligase (New England BioLabs, Ipswich, Mass.) following manufacturer recommendations and the resulting products were transformed into *E. coli* TOP 10 electrocompetent cells (Invitrogen, Carlsbad, Calif.) using standard techniques. Cells were plated on LB agar plates containing 100 ug/ml of Spectinomycin and incubated overnight at 37° C. Obtained clones were sequence verified.

Example 8

Construction of pCDX11-8087-rbsA-FabH-D-G Plasmid

The plasmid pCDX1-8087-rbsA-FabH-FabD-FabG was constructed as described below. The *E. coli* fabH-fabD-JabG operon was PCR amplified from genomic DNA isolated from *E. coli* strain W3110 with primers fabH-mid_F and BamHI-fabG_R:

```
fabH-mid_F:
                                          (SEQ ID NO: 49)
5'-GTCGTCGGTTCCGATGTACT-3'
and BamHI-fabG_R:
                                          (SEQ ID NO: 50)
5'-AAAAGGATCCTTAGACCATGTACATCCCGCC-3'.
```

Primer BamHI-fabG_R was designed to replace the normal TGA stop codon of fabG with the TAA stop codon.

The PCR reactions were carried out using the using the enzyme Phusion (New England BioLabs, Ipswich, Mass.) with an initial denaturation step at 98° C. for 30 sec, followed by 30 cycles of the steps: 98° C. for 5 sec; 63° C. for 20 sec and 72° C. for 30 sec. This was followed by a final elongation step at 72° C. for 5 min. After the PCR reaction, the PCR product was purified through a PCR purification column and eluted with water.

The PCR product and the pCDX11-8087-rbsA-fabH plasmid were digested with the restriction enzymes SapI and BamHI (New England BioLabs, Ipswich, Mass.) following manufacturer recommendations. The plasmid and inserts were ligated using Quick Ligase (New England BioLabs, Ipswich, Mass.) following manufacturer recommendations and the resulting products were transformed into *E. coli* TOP 10 electrocompetent cells (Invitrogen, Carlsbad, Calif.) using standard techniques. Cells were plated on LB agar plates containing 100 ug/ml of Spectinomycin and incubated overnight at 37° C. Obtained clones were sequence verified.

Example 9

Construction of pCK-900-FabI-1-FabZ Plasmid

Plasmid pCK900-FabI-1-FabZ was constructed as follows:
(a) To clone FabI, the protein sequence of FabI-1 from *Rhodobacter sphaeroides* SB103 (SEQ ID NO: 20) (GenBank: ADE86080) was utilized to design an *E. coli* codon-optimized gene (SEQ ID NO: 19). The gene was synthesized and cloned in pUC57 by GenScript (Piscataway, N.J.). The gene was PCR amplified from plasmid pUC57-FabI-1, using Phusion polymerase, with primers containing a SalI site and RBS/spacing in front of fabI-1: and a HindIII site on the 3' end primer. Primers sequences:

```
FabI-1_F
                                          (SEQ ID NO: 53)
ACTAAGTCGACATAAGGAGATATACATATGACC
and FabI-1_R
                                          (SEQ ID NO: 54)
AGGTCAAGCTTATTAGTCTTTACG.
```

The PCR reaction was carried out using the enzyme Phusion (New England BioLabs, Ipswich, Mass.) with an initial denaturation step at 98° C. for 10 sec, followed by 25 cycles of the steps: 98° C. for 20 sec; 56° C. for 20 sec and 72° C. for 30 sec. This was followed by a final elongation step at 72° C. for 5 min. After the PCR reaction, the product was purified through a PCR purification column and eluted with water. The DNA was digested with the restriction enzymes SalI and HindIII (New England BioLabs, Ipswich, Mass.) following manufacturer recommendations.

(b) The *E. coli* fabZ gene (SEQ ID NO: 21) including its natural RBS/spacing sequence was PCR amplified from genomic DNA isolated from *E. coli* strain W3110, using primers:

```
FabZ-Fwd
                                    (SEQ ID NO: 51)
5'-ACAGGAAGAGTATCATGACTACTAAC-3'

FabZ-Rev
                                    (SEQ ID NO: 52)
5'-TTAGGCCTCCCGGCTACGAGCAC-3'.
```

The PCR reaction was carried out as described above in the previous section, except that 30 cycles were used for the amplification step. These primers were also used to replace the original TTG start and TGA stop codons present in fabZ, with ATG and TAA codons respectively.

The PCR product obtained was cloned using the TOPO kit from Invitrogen (Carlsbad, Calif.) following manufacturer instructions. Topo cloning reaction was transformed into commercial electrocompetent TOP 10 *E. coli* cells and cells were plated on LB agar plates containing 100 micrograms/ml of Carbenicillin. Plates were incubated overnight at 37° C. The sequence of fabZ gene was verified.

(c) Construction of pCL5019: A gene (SEQ ID NO:3) encoding the FAR-V1 polypeptide was ligated as NcoI-SalI fragments to pLS8379 digested with the same restriction enzymes. Ligation reactions were incubated overnight at 16° C. and then transformed into *E. coli* DH10B-T1 electrocompetent cells (Invitrogen, Carlsbad, Calif.) following the manufacturer's protocols. Cells were plated on LB agar plates containing 100 µg/ml of Spectinomycin. Plates were incubated overnight at 370 C. Obtained clones were sequence verified and the resulting plasmid was named pCL5019.

(d) Construction of pCL5019linker: pCL5019 plasmid was digested with restriction enzymes SalI-PmeI (New England BioLabs, Ipswich, Mass.) following manufacturer recommendations and a synthetic linker containing a multicloning site (MCS) was ligated into this vector to facilitate further cloning.

```
pCLlinker_F
                                    (SEQ ID NO: 35)
TCGACATAGATCTAGAACTTACTCGGAAGGTTCTTAATTA AGAGGATCCATTGACGTCTATGAATTCGTTT
and pCLlinker_R
                                    (SEQ ID NO: 36)
AAACGAATTCATAGACGTCAATGGATCCTCTTAATTAAGA

AGCTTCCGAGTAAGTTCTAGATCTATG.
```

After ligation, the obtained plasmid pCL5019linker was sequence verified.

(e) Construction of pCL5019-FabI-1-FabZ: The pCL5019linker was linearized by digestion with the SalI and AatII restriction enzymes. (New England BioLabs, Ipswich, Mass.) following manufacturer recommendations. The fabI-1 gene was amplified from plasmid pUC57-FabI-1, using Phusion polymerase, with primers containing a SalI site and a HindIII site on the 3' end primer. Primers sequences:

```
FabI-1_F
                                    (SEQ ID NO: 53)
ACTAAGTCGACATAAGGAGATATACATATGACC
and 5019-FabI-1_R
                                    (SEQ ID NO: 54)
AGGTCAAGCTTATTAGTCTTTACG.
```

The PCR reaction was carried out using the enzyme Phusion (New England BioLabs, Ipswich, Mass.) with an initial denaturation step at 98° C. for 10 sec, followed by 25 cycles of the steps: 98° C. for 20 sec; 56° C. for 20 sec and 72° C. for 30 sec. This was followed by a final elongation step at 72° C. for 5 min. After the PCR reaction, the PCR product was purified through a PCR purification column and eluted with water. This DNA was digested with the restriction enzymes SalI and HindIII (New England BioLabs, Ipswich, Mass.) following manufacturer recommendations. The fabZ gene was PCR amplified from TOPO-fabZ plasmid described above section (b), with primers containing HindIII site on 5' end primer and AatII site on 3' end primer.

```
FabZ_F
                                    (SEQ ID NO: 55)
AGTAAGCTTGAGTTTAGGAAGAGTATCATG
and FabZ_R
                                    (SEQ ID NO: 56)
AAGCTGACGTCTTAGGCCTCCCGGCTACG.
```

The resulting PCR product was purified through a PCR purification column; eluted with water. The DNA was digested with the restriction enzymes HindIII and AatII (New England BioLabs, Ipswich, Mass.) following manufacturer recommendations.

The final plasmid pCL5019-FabI-1-fabZ was obtained by a three way ligation between FabI-1/SalI-HindIII, FabZ/HindIII-AatII fragments and pCL5019linker vector digested with SalI-AatII. Ligation reaction was performed overnight at 16° C.

(f) Construction of pCK900-FabI-1-FabZ: FabI-1_fabZ genes were PCR amplified from pCL-5019-fabI-1-fabZ plasmid described above (e) with the following primers:

```
488
                                    (SEQ ID NO: 57)
5'-GATACGACCCGTAAACTTGCAACCATTTTTGGC-3'
and 8379_R
                                    (SEQ ID NO: 58)
5'-CGCTTCTGCGTTCTGATTT-3'.
```

The PCR reaction was carried out using the enzyme Phusion (New England BioLabs, Ipswich, Mass.) with an initial denaturation step at 98° C. for 30 sec, followed by 25 cycles of the steps: 98° C. for 10 sec; 56° C. for 20 sec and 72° C. for 40 sec. This was followed by a final elongation step at 72° C. for 5 min. Obtained PCR product was purified using PCR clean-up Gel extraction Kit (Macherey-Nagel Inc.), digested with NdeI and EcoRI enzymes, gel purified and ligated with pCK900-BlaI vector digested with the same restriction endonucleases. The ligation reaction was incubated ON at 16° C. and then transformed into *E. coli* DH10B-T1 strain. 1 ml of SOC (Super Optimal Media with Catabolite Repression) media was added to transformed cells and cells were left to recover for 1 h at 37° C. with shaking at 250 rpm. Cells were plated on LB agar/with 30 microgram ml$^{-1}$ of chloramphenicol Petri dish plates incubated overnight at 37° C. The presence of the insert was verified by colony PCR with GoTag GreenMix (Promega) and the obtained clone was sequence verified.

Example 10

Generating W3110 ΔFhua Strain Harboring Plasmids

Electrocompetent cells of *E. coli* W3110 ΔfhuA were prepared as follows. The culture was grown in LB media to an OD$_{600}$ of ~0.6 and concentrated 100-fold by centrifugation. The cells were washed three times with ice-cold sterile water, and then washed once with ice-cold 10% glycerol. The various plasmids as described above were introduced into the electrocompetent *E. coli* W3110 ΔfhuA using standard methods (Dower et al., 1988 NAR 16:6127-6145).

Example 11

Fatty Alcohol Production

Recombinant *E. coli* host strains comprising a plasmid including heterologous genes as specified above were grown in M9 (Sambrook et al., (2001) Molecular Cloning: A Laboratory Manual 3$^{rd}$ Ed Cold Spring Harbor, N.Y.) medium supplemented with 1% glucose, 2 g/l yeast extract and the specified antibiotic selection, for approximately 16-18 hours (overnight) at 30° C., 200 rpm. A 5% inoculum was used to initiate fresh M9 media, 5% glucose and 2 g/l yeast extract containing spectinimycin at 100 micrograms ml$^{-1}$ when the pCDX11 vector was used and chloramphoenicol at 30 micrograms ml$^{-1}$ when pCK900-I-bla was used. The culture was incubated in a shaker for 2.5 hours at 30° C. and at 250 rpm to an OD$_{600}$ of about 0.6 to about 0.8. The expression of the heterologous FAR was then induced with isopropyl-β-D-thiogalactoside (IPTG) (1 mM final concentration). Incubation was continued for about 48 hours under the same conditions. Fatty acid species including fatty alcohols were extracted using 1 mL of methyl isobutyl ketone (MIBK) into 500 μl of cell culture, sealed tightly and shaken for ≥2.5 h. The extract was centrifuged and analyzed directly by GC-FID. A 1 μL sample was analyzed by GC-FID with the split ratio 1:10 using the following conditions: GC-6890N from Agilent Technologies equipped with FID detector and HP-5 column (length 30 m, I.D. 0.32 mm, film 0.25 μm). GC method: start at 100° C., with an increase in temperature at a rate of 25° C./min to 246° C. which was held for 1.96 min. Total run time was 7.8 min. Under the above GC conditions, the approximate retention times (min) of produced fatty alcohols and acids were as follows: 1.81, C10:0-OH; 2.47, C12:0-OH: 5.08, C14:0-OH; 5.40, C14:0-OOH; 5.74, C16:1-OH; 5.93, C6:0-OH; 6.11, C16:0-OOMe (internal standard); 6.16, C16:1-OOH; 6.29, C16:0-OOH; 6.80, C18:1-OH; 6.90, C18:0-OH; and 7.3, C18:0- and C18:1-OOH. Results of fatty alcohol production under these conditions are depicted in Tables 2-5. Identification of individual fatty alcohols was determined by comparison to commercial standards (Sigma Chemical Company, 6050 Spruce St. Louis, Mo. 63103). ("Sat."="saturation".)

TABLE 2

Fatty Alcohol (FOH) Production in a W3110 ΔfhuA Strain

| Plasmids | % Sat. | % C12 | % C14 | % C16 | % C18 | Total FOH (g/L) |
|---|---|---|---|---|---|---|
| pCDX11-7076 pCK900-I | 65 | 12 | 57 | 30 | 2 | +++ |
| pCDX11-7076-rbsH-FabH pCK900-I | 67 | 15 | 59 | 24 | 1 | +++ |
| pCDX11-7076-rbsA-FabH pCK900-I | 71 | 21 | 60 | 19 | 0 | +++ |
| pCDX11-7076 pCK900-FadD-TE | 68 | 41 | 26 | 24 | 4 | +++ |
| pCDX11-7076-rbsH-FabH pCK900-FadD-TE | 69 | 40 | 32 | 23 | 2 | ++ |
| pCDX11-7076-rbsA-FabH pCK900-FadD-TE | 81 | 59 | 32 | 10 | 0 | + |

% as measured by calculating the individual fatty alcohols as part of the sum of all fatty alcohol measured.
All values are rounded to the closest unit.
CX (wherein X = 12, 14, 16 or 18) denotes both saturated and unsaturated species.
Total FOH g/L wherein + is <1.0; ++ is 1.0 to <3.0 and +++ is 3.0 or greater.

TABLE 3

Fatty Alcohol (FOH) Production in a W3110K ΔfhuA::FRT Strain

| Plasmids | % Sat. | % C12 | % C14 | % C16 | % C18 | Total FOH (g/L) |
|---|---|---|---|---|---|---|
| pCDX11-8087 | 57 | 12 | 52 | 30 | 3 | ++ |
| pCDX11-8087-rbsA-FabH | 65 | 20 | 56 | 20 | 0 | ++ |
| pCDX11-8087-rbsA-FabH-FabD-FabG | 70 | 28 | 51 | 18 | 0 | + |

% as measured by calculating the individual fatty alcohols as part of the sum of all fatty alcohol measured.
CX (wherein X = 12, 14, 16, or 18) denotes both saturated and unsaturated species.
All values are rounded to the closest unit.
Total FOH g/L wherein + is <1.0; ++ is 1.0 to <3.0 and +++ is 3.0 or greater.

TABLE 4

Fatty Alcohol (FOH) Production in a W3110 ΔfhuA strain

| Plasmids | % Sat. | % C12 | % C14 | % C16 | Total FOH (g/L) |
|---|---|---|---|---|---|
| pCDX11-8087-rbsA-FabH pCK900-FabI-1-FabZ | 92 | 15 | 71 | 13 | ++ |
| pCDX11-8087-rbsA-FabH-FabD-FabG pCK900-FabI-1-FabZ | 93 | 19 | 69 | 12 | ++ |
| pCDX11-8087-rbsA-FabH pCK900-FabI-1-FabZ in a ΔfadR strain | 97 | 32 | 62 | 6 | ++ |
| pCDX11-8087-rbsA-FabH-FabD-FabG pCK900-FabI-1-FabZ in a ΔfadR strain | 97 | 43 | 52 | 5 | + |

% as measured by calculating the individual fatty alcohols as part of the sum of all fatty alcohol measured.
% C18-OH measured approximately 0 in all cases.
CX (wherein X = 12, 14 or 16) denotes saturated and unsaturated species.
All values are rounded to the closest unit.
Total FOH g/L wherein + is <1.0; ++ is 1.0 to <3.0 and +++ is 3.0 or greater.

TABLE 5

Fatty Alcohol (FOH) Production in a W3110K Strain

| Plasmids | % Sat. | % C12 | % C14 | % C16 | % C18 | Total FOH (g/L) |
|---|---|---|---|---|---|---|
| pCDX11-8087 | 56 | 13 | 52 | 30 | 2 | ++ |
| pCDX11-8087-FabI-1-FabZ | 82 | 8 | 53 | 35 | 2 | ++ |
| pCDX11-8087-rbsA-FabH pCK900-FabI-1-FabZ | 91 | 22 | 63 | 15 | 0 | ++ |

% as measured by calculating the individual fatty alcohols as part of the sum of all fatty alcohol measured.
CX (wherein X = 12, 14, 16 or 18 denotes saturated and unsaturated species.
All values are rounded to the closest unit.
Total FOH g/L wherein + is <1.0; ++ is 1.0 to <3.0 and +++ is 3.0 or greater.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

The invention claimed is:

1. An engineered prokaryotic cell comprising two recombinant polynucleotides, the first polynucleotide encodes a heterologous fatty alcohol forming reductase (FAR) comprising the amino acid sequence of SEQ ID NO: 8, and the second polynucleotide encodes a β-ketoacyl acyl carrier protein synthase III (FabH).

2. The engineered prokaryotic cell of claim 1, wherein the engineered prokaryotic cell is a bacterial cell.

3. The engineered prokaryotic cell of claim 2, wherein the bacterial cell is an *E. coli* cell.

4. The engineered prokaryotic cell of claim 1, further comprising a recombinant polynucleotide encoding a thioesterase (TE), wherein the TE comprises an amino acid sequence at least 90% sequence identity to SEQ ID NO: 63.

5. The engineered prokaryotic cell of claim 1, wherein the TE comprises an amino acid sequence at least 90% sequence identity to SEQ ID NO: 12.

6. The engineered prokaryotic cell of claim 1, wherein the TE comprises an amino acid sequence at least 95% sequence identity to SEQ ID NO: 12 or SEQ ID NO: 63.

7. The engineered prokaryotic cell of claim 1, further comprising one or more introduced polynucleotide encoding a FabD and/or FabG enzyme.

8. The engineered prokaryotic cell of claim 7, wherein said introduced polynucleotide encodes the FabD enzyme.

9. The engineered prokaryotic cell of claim 7, wherein the FabD enzyme comprises an amino acid sequence at least 90% sequence identity to SEQ ID NO: 26.

10. The engineered prokaryotic cell of claim 7, wherein said introduced polynucleotide sequence encodes the FabG enzyme.

11. The engineered prokaryotic cell of claim 7, wherein the FabG enzyme comprises an amino acid sequence at least 90% sequence identity to SEQ ID NO: 18.

12. The engineered prokaryotic cell of claim 7, wherein the introduced polynucleotide encode the FabD and FabG enzymes, wherein the FabD enzyme has an amino acid sequence at least 90% sequence identity to SEQ ID NO: 26, and wherein the FabG enzyme has an amino acid sequence at least 90% sequence identity to SEQ ID NO: 18.

13. The engineered prokaryotic cell of claim 1, further comprising an introduced polynucleotide encoding a Fab enzyme selected from a FabI and a FabZ enzyme.

14. The engineered prokaryotic cell of claim 13, wherein the FabI enzyme has an amino acid sequence at least 90% sequence identity to SEQ ID NO: 20.

15. The engineered prokaryotic cell of claim 13, wherein the FabZ enzyme has an amino acid sequence at least 90% sequence identity to SEQ ID NO: 22.

16. The engineered prokaryotic cell of claim 13, wherein the introduced polynucleotide encodes the FabI enzyme and the FabZ enzyme.

17. The engineered prokaryotic cell of claim 1, further comprising the expression of at least one endogenous genes selected from fadE, fadR, fadD, fabB, fabH and fabF, is attenuated.

18. The engineered prokaryotic cell of claim 1, further comprising a recombinant acyl-CoA synthase (FadD).

19. A cell culture comprising the engineered prokaryotic cell of claim 1.

20. A method of producing a fatty alcohol composition comprising
  a) providing the engineered prokaryotic cell of claim 1;
  b) culturing the engineered prokaryotic cell of claim 1 under suitable culture conditions in the presence of a carbon source;
  c) producing fatty alcohols; and
  d) optionally recovering the fatty alcohols from the engineered cell of claim 1 or from a culture medium thereof.

21. The method of claim 20, wherein the carbon source comprises a fermentable sugar.

22. The method of claim 21, wherein the fermentable sugar comprises glucose.

23. The method of claim 21, wherein the fermentable sugar is obtained from a cellulosic feedstock.

24. The method of claim 23, wherein the cellulosic feedstock is derived from a biomass selected from grain (e.g. corn), corn stover, corn cobs, wheat straw, bagasse and beet pulp.

25. The method of claim 24, wherein the biomass has been pretreated.

26. The method of claim 20, wherein at least 1 g/L of fatty alcohols are produced by the engineered prokaryotic cell.

27. The method of claim 20, wherein the total fatty alcohol composition produced comprises at least 60% C12 to C14 fatty alcohols.

28. The method of claim 27, wherein the total fatty alcohol composition produced comprises at least 70% C12 to C14 fatty alcohols.

29. A vector comprising a first polynucleotide encoding a FAR comprising the amino acid sequence of SEQ ID NO: 8, and a second polynucleotide encoding a FabH, wherein the first and second polynucleotides are operably linked to a promoter that is functional in a prokaryotic host cell.

30. A recombinant bacterial culture that produces a composition of fatty alcohols comprising at least 60% C12, C14 and C16 fatty alcohols, wherein the recombinant bacterial culture comprises an engineered bacterial microorganism comprising a gene encoding a heterologous FAR comprising the amino acid sequence of SEQ ID NO: 8 and a gene encoding a heterologous FabH comprising an amino acid sequence at least 90% sequence identity to SEQ ID NO: 10.

31. The recombinant bacterial culture of claim 30, wherein the engineered bacterial microorganism is an *E. coli* strain.

32. The recombinant bacterial culture of claim 30, wherein the fatty alcohol composition produced comprises at least 80% of C12, C14 and C16 fatty alcohols, or comprises at least 60% of the combination of C12 and C14 fatty alcohols.

33. A method of shifting the C12, and C16 fatty alcohols carbon chain length profile in a fatty alcohol composition produced by an engineered bacterial cell comprising a polynucleotide encoding a heterologous FAR having the amino acid sequence of SEQ ID NO: 8, said method comprises introducing a polynucleotide encoding a FabH having at least 90% sequence identity to SEQ ID NO: 10 into the engineered bacterial cell to produce newly engineered bacterial cell, wherein the composition of C12 fatty alcohols produced by the newly engineered bacterial cell has been increased by 25% and the composition of C16 fatty alcohols has been decreased by at least 10% as compared to the engineered bacterial cell.

* * * * *

UNITED STATES PATENT AND TRADEMARK OFFICE
CERTIFICATE OF CORRECTION

PATENT NO.       : 9,650,655 B2                          Page 1 of 1
APPLICATION NO.  : 14/415665
DATED            : May 16, 2017
INVENTOR(S)      : Vroom et al.

It is certified that error appears in the above-identified patent and that said Letters Patent is hereby corrected as shown below:

In the Claims

In Claim 26, Column 130, Line 58, please delete "by the engineered prokaryotic cell".

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*